United States Patent
Seale et al.

(10) Patent No.: US 9,074,012 B2
(45) Date of Patent: Jul. 7, 2015

(54) MOLECULAR CONTROL OF BROWN FAT DIFFERENTIATION AND ENERGY EXPENDITURE

(75) Inventors: Patrick Seale, Media, PA (US); Bruce M. Spiegelman, Waban, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1471 days.

(21) Appl. No.: 12/446,110

(22) PCT Filed: Oct. 17, 2007

(86) PCT No.: PCT/US2007/022162
§ 371 (c)(1),
(2), (4) Date: Nov. 11, 2010

(87) PCT Pub. No.: WO2008/063330
PCT Pub. Date: May 29, 2008

(65) Prior Publication Data
US 2011/0059051 A1    Mar. 10, 2011

Related U.S. Application Data

(60) Provisional application No. 60/852,564, filed on Oct. 18, 2006.

(51) Int. Cl.
| | | |
|---|---|---|
| *A61K 48/00* | (2006.01) | |
| *C12N 15/63* | (2006.01) | |
| *C12N 15/85* | (2006.01) | |
| *C07K 14/00* | (2006.01) | |
| *C07H 21/04* | (2006.01) | |
| *C07K 14/47* | (2006.01) | |
| *C12N 5/077* | (2010.01) | |

(52) U.S. Cl.
CPC .............. *C07K 14/4702* (2013.01); *A61K 48/00* (2013.01); *C12N 15/63* (2013.01); *C07H 21/04* (2013.01); *C12N 5/0653* (2013.01); *C12N 2501/60* (2013.01); *C12N 2506/1307* (2013.01)

(58) Field of Classification Search
CPC ...... A61K 48/00; C12N 15/63; C12N 5/0653; C12N 2501/60; C12N 2506/1307; C07H 21/04; C07K 14/4702
USPC .............. 514/44 R; 435/320.1, 455; 530/350; 536/23.5
See application file for complete search history.

(56) References Cited

U.S. PATENT DOCUMENTS

2004/0014192 A1   1/2004  Huang

OTHER PUBLICATIONS

Kalle et al., 2009, US 20090028836 A1, effective filed, Jun. 1, 2005.*
Gorecki, D., 2001, Expert Opin. Emerging Drugs, 6(2): 187-198.*
Bennett, J., 2003, Gene Therapy, vol. 10, p. 977-982.*
Thomas et al., 2003, Nature Reviews/ Genetics, vol. 4, p. 346-358.*
Lebedeva et al., 2003, Seminars in Cancer Biology, vol. 12, p. 169-178.*
Kodama et al., 2006, Current Medicinal Chemistry, vol. 13, p. 2155-2161.*
Hamman et al., 2005, Biodrugs, vol. 19, No. 3, p. 165-177.*
Torchilin et al., 2003, DDT, vol. 8, No. 6, p. 259-266.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002,, Virology, vol. 304, p. 135-145.*
Chattopadhyay et al., 2004, Virus Research, vol. 99, p. 139-145.*
Barjesteh van Waalwijk van Doorn-Khosrovani et al., "Low expression of MDS1-EVI1-like-1 (MEL1) and EVI1-like-1 (EL1) genes in favorable-risk acute myeloid leukemia," Exp. Hematol., 31(11):1066-1072 (2003).
Database GenBank Oct. 31, 2003, "*Mus musculus* mell mRNA for transcription factor MEL1, complete cds," XP002487404, Database accession No. AB078338.
Lahortiga et al., "Molecular characterization of a t(1;3)(p36;q21) in a patient with MDS. MEL1 is widely expressed in normal tissues, including bone marrow, and it is not overexpressed in the t(1;3) cells," Oncogene, 23(1):311-316 (2004).
Mochizuki et al., "A novel gene, MEL1, mapped to lp36.3 is highly homologous to the MDS1/EVI1 gene and is transcriptionally activated in t(1;3)(p36;q21)-positive leukemia cells," Blood, 96(9):3209-3214 (2000).
Nishikata et al., "A novel EVI1 gene family, MEL1, lacking a PR domain (MEL1S) is expressed mainly in t(1;3)(p36;q21)-positive AML and blocks G-CSF-induced myeloid differentiation," Blood, 102(9):3323-3332 (2003).
Seale et al., "Transcriptional Control of Brown Fat Determination by PRDM16," Cell Metabolism, 6:38-54 (2007).
Spiegelman et al., "The adipocyte: a multifunctional cell," Cell Metabolism, 4(6):425-427 (2006).

* cited by examiner

*Primary Examiner* — Shin Lin Chen
(74) *Attorney, Agent, or Firm* — Foley Hoag LLP

(57) ABSTRACT

The invention provides methods and compositions for inducing brown fat cell differentiation through modulation of Prdm 16 activity or expression. Also provided are methods for preventing or treating obesity or an obesity related disorder in a subject through stimulation of Prdm 16 expression or activity. Further provided are methods for identifying compounds that are capable of modulating Prdm 16 expression or activity.

8 Claims, 36 Drawing Sheets

```
   1 gacaatgctg gggagatgaa gatagtgtgt ggctgcttct ggactcaagg aggaggagag
  61 agattccgcg agccgacacc atgcgatcca aggcgagggc gaggaagcta gccaaaagtg
 121 acggtgacgt tgtaaataat atgtatgagc ccaaccggga cctgctggcc agccacagcg
 181 cggaggacga ggccgaggac agtgccatgt cgcccatccc cgtggggcca ccgtcccct
 241 tccccaccag cgaggacttc accccaagg agggctcgcc gtacgaggcc cctgtctaca
 301 ttcctgaaga cattccgatc ccagcagact tcgagctccg agagtcctcc atcccagggg
 361 ctggcctggg ggtctgggcc aagaggaaga tggaagccgg ggagaggctg ggcccctgcg
 421 tggtggtgcc ccggcggcg gcaaaggaga cagacttcgg atgggagcaa atactgacgg
 481 acgtggaagt gtcgccccag gaaggctgca tcacaaagat ctccgaagac ctgggcagtg
 541 agaagttctg cgtggatgca atcaggcgg gggctggcag ctggctcaag tacatccgtg
 601 tggcgtgctc ctgcgatgac cagaacctca ccatgtgtca gatcagtgag cagatttact
 661 ataaagtcat taaggacatt gagccaggtg aggagctgct ggtgcacgtg aaggaaggcg
 721 tctacccccct gggcacagtg ccgcccggcc tggacgagga gcccacgttc cgctgtgacg
 781 agtgtgacga actcttccag tccaagctgg acctgcggcg ccataagaag tacacgtgtg
 841 gctcagtggg ggctgcgctc tacgagggcc tggctgagga gctcaagccc gagggccttg
 901 gcggtggcag cggccaagcc cacgagtgca aggactgcga gcggatgttc cccaacaagt
 961 acagcctgga gcagcacatg gtcatccaca cggaggagcg cgagtacaaa tgcgaccagt
1021 gtcccaaggc cttcaactgg aagtccaacc tcatccgcca ccagatgtcc cacgacagcg
1081 gcaaacgctt cgaatgtgaa actgcgtga aggtgttcac ggaccccagc aaccttcagc
1141 ggcacatccg ctcgcagcac gtgggcgctc gggcccacgc ctgccccgac tgcggaaga
1201 ccttcgccac gtcctccggc ctcaagcagc acaagcatat ccacagcacg gtgaagcctt
1261 tcatatgtga ggtctgccac aagtcctaca cgcagttctc caacctgtgc cggcacaagc
1321 ggatgcacgc cgactgccgc acgcagatca agtgcaagga ctgtggccag atgttcagca
1381 ctacctcctc cctcaacaag caccggcgct ctgcgaggg caagaaccat tacacgccgg
1441 gcggcatctt tgccccgggc ctgcccttga ccccagccc catgatggac aaggcaaaac
1501 cctcccccag cctcaatcac gccagcctgg gcttcaacga gtactttccc tccaggccgc
1561 acccggggag cctgccctc tccacggcgc ctcccacgtt ccccgcactc accccggct
1621 tcccgggcat cttccctcca tccttgtacc cccggccgcc tctgctacct cccacatcgc
1681 tgctcaagag ccccctgaac cacacccagg acgccaagct ccccagtccc ctggggaacc
1741 cagccctgcc cctggtctcc gccgtcagca cagcagcca gggcacgacg cagctgcgg
1801 ggcccgagga gaagttcgag agccgcctgg aggactcctg tgtggagaag ctgaagacca
1861 ggagcagcga catgtcggac ggcagtgact tgaggacgt caacaccacc acggggaccg
1921 acctggacac gaccacgggg acgggctcgg acctggacag cgacgtggac agcgaccctg
1981 acaaggacaa gggcaagggc aagtccgccg agggccagcc caagtttggg ggcggcttgg
2041 cgcccccggg ggccccgaac agcgtggccg aggtgcctgt cttctattcc cagcactcat
2101 tcttcccgcc acccgacgag cagctgctga ctgcaacggg cgccgccggg gactccatca
2161 aggccatcgc atccattgcc gagaagtact ttggccccgg cttcatgggg atgcaggaga
```

Figure 1 (Cont.)

```
2221 agaagctggg ctcgctcccc taccactcgg cgttcccctt ccagttcctg cccaacttcc
2281 cccactccct ttacccttc acggaccgag ccctcgccca caacttgctg gtcaaggccg
2341 agccaaagtc accccgggac gccctcaagg tgggcggccc cagtgccgag tgcccctttg
2401 atctcaccac caagcccaaa gacgtgaagc ccatcctgcc catgcccaag ggcccctcgg
2461 cccccgcatc cggcgaggag cagccgctgg acctgagcat cggcagccgg gcccgtgcca
2521 gccaaaacgg cggcgggcgg gagccccgca gaaccacgt ctatggggaa cgcaagctgg
2581 gcgccggcga ggggctgccc caggtgtgcc cggcgcggat gccccagcag ccccgctcc
2641 actacgccaa gccctcgccc ttcttcatgg accccatcta cagggtagaa aagcggaagg
2701 tcacagaccc cgtgggagcc ctgaaggaga agtacctgcg gccgtccccg ctgctcttcc
2761 accccagat gtcagccata gagaccatga cagagaagct ggagagcttt gcagccatga
2821 aggcggactc gggcagctcc ctgcagcccc tccccacca cccccttcaac ttccggtccc
2881 cacccccaac gctctccgac cccatcctca ggaagggcaa ggagcgatac acgtgcaggt
2941 actgtgggaa gatcttcccc agatcagcca atctcaccag acacctgagg acgcacactg
3001 gggagcagcc gtacaggtgt aagtactgcg accgctcctt cagcatctct tcgaacctcc
3061 agcggcacgt ccggaacatc cacaacaagg agaagccttt caagtgccac ctgtgcaacc
3121 gctgcttcgg gcagcagacc aacctggacc ggcacctcaa gaagcacgag cacgagaacg
3181 caccagtgag ccagcacccc ggggtcctca cgaaccacct ggggaccagc gcgtcctctc
3241 ccacctcaga gtcggacaac cacgcacttt tagacgagaa agaagactct tatttctcgg
3301 aaatcagaaa ctttattgcc aatagtgaga tgaaccaagc atcaacgcga acagagaaac
3361 gggcggacat gcagatcgtg gacggcagtg cccagtgtcc aggcctagcc agtgagaagc
3421 aggaggacgt ggaggaggag gacgacgatg acctggagga ggacgatgag gacagcctgg
3481 ccgggaagtc gcaggatgac accgtgtccc cgcacccga gccccaggcc gcctacgagg
3541 atgaggagga tgaggagcca gccgcctccc tggccgtggg ctttgaccac acccgaaggt
3601 gtgctgagga ccacgaaggc ggtctgttag ctttggagcc gatgccgact tttgggaagg
3661 ggctggacct ccgcagagca gctgaggaag catttgaagt taaagatgtg cttaattcca
3721 ccttagattc tgaggcttta aaacatacac tgtgcaggca ggctaagaac caggcatatg
3781 caatgatgct gtccctttcc gaagacactc ctctccacac cccctcccag ggttctctgg
3841 acgcttggtt gaaggtcact ggagccacgt cggagtctgg agcatttcac cccatcaacc
3901 acctctgacg ggctgggcag ccggggccg gtggccagag cgagggcacc agccacgaag
3961 gacggaggcg ggcggggccc cggagaaccc tgtccctgcg tgtggccact cctcagcatc
4021 ctccccaccc accatggttc attccgactt ttccaatgga aactcagatc ccaaaagtcc
4081 ctaaagcagt cgtagagtct caccatctcc aaggattggt cttgagaaca ctgttcagtg
4141 acggccatgc aggtggccgt ccaaagacag ccaacggagc tgcctcgcag aatcagccag
4201 tgggcaggtg gacgctctgc tgagacagaa gctggtggcc actgccgggt gcccgcgtgg
4261 ggtcgcggaa gggaatggat agactggtgt gctcaaaaga gagagatcac tcaaatgatt
4321 tttataatga aatgacaaga ataacccttt tggtaaccgt attgactgca gagtctattt
4381 aagcatgtgg ttttaaaaat agacagtatt ttttaaaaat caaaaaatga cttgcaaatt
4441 gttttttaaa agtaattttg cattgctttg aaatttgagc tcatttgcaa acccgagtct
4501 gcctgggaac ccgcactgtg cctgggtgta ttctttatac tgtagataat ggagaaattt
```

Figure 1 (Cont.)

```
4561 tctatctctg tccctatttg tataagccaa ggtgatgctg ggtgccccga ggcagaacaa
4621 gaggcgcggg gccacacccg tgaaccatgc agacggccga agaagtctta ggcagggcgc
4681 cctgggctgc aggcctgccc gaggctggga tgggaagtgt gcctgccctc gtgtgacatg
4741 gaattggtgt caggaccgcc acgtggcctt cagaggaatc cacaggtccc cacccaagat
4801 ccctcaatta tatgggaaag tcgagggcct gtggcttgga tccgccatgc agagatgtgg
4861 ccgggcaccc atcttccttc cctcctctgt ccctgcctcg gccaccccac gcgggaaccc
4921 agcgccgtcc tctgaaggca gggccttggc cacgtcctgg gtctcccacc tcccacctga
4981 ccccagcggc tccggtgtcc tccacgtggc tgccctgggg agcaatccca gcggatcgct
5041 ccgggccacc aagccgcacc tgtgcctgag actccggatg gacgacacag tcgtcacgtc
5101 gctcttcctg cgggttcttg gcgagacaca gcttgagaac agaagggcgt cgggggaacc
5161 tgccgcaagg agcagagaca gcacagcccc ccgggcccag ccgcctccct ctcttgggac
5221 gcaacttctt ccccactcgg atgggcttta aattattccc ataggggcca atttcaaata
5281 ataatttttt tccctgatgg aatttacctt aatctgtata taacttgtaa ttttttctaa
5341 ttcatttctt ttcttatttt atttcctcct taacagtatt tttggcatta gacattctta
5401 ttgtgaagaa ataatgttaa tataagtatc tggtgaagga ccaaaaccgt gtgataaggt
5461 tgtgtgtcgt gtgggagtgg ggcgattttt tatgtgccaa ataccccgt cccccccatg
5521 aatcctgctg tccctgctgc cgtttaccag acaatcatat gttttgtta aatttgcgtt
5581 tcagttacat ttgcatttaa gacaagtgtt ctatttattt cttgtattgt ttggaagaaa
5641 aaatgatgat agagtcccaa aaagaagaga aaaaaatgc ccaagttgcc ctttaaaaaa
5701 aaagagcgta aatacaaaca ggagtggtgc aagccgcctt ggtgtgggtt tgtgtcacgt
5761 gtggacatct cctcaggctt tgtgtcacgc gtggacatct cctcaggctg tccccagcgg
5821 tgacgggagg tgtcctggct gctccaggac aaaagacaat cgtctctgtg ggtgccgggt
5881 ggtccaggct tgcactgaag acgtgccacg gggaggctcc tgcaggaggc tcaacccgac
5941 ggatcacagt gaaagggatt cctcccacgc cagatctgca caacgaggca agacaggacc
6001 cacctgtgcg tgcgctgggg ccatggggtg gccccgccgg ggcagcgggg gagctgcctg
6061 cagaagagcc agctggcgtg tcgggaagga tccaggatct gcaaacacaa ctgctcaggc
6121 cttctcacgc gtttccacaa catccctgg gtcagaccca ccaggtaccc cgtaggaatt
6181 tccagttttcc cttgatctag atgggattct tataaaaatt caacctcaga cataaacacc
6241 ccatttctgt aaacccaaat tatatggttt cttctgcgaa agagtaaggt gtgtgctttt
6301 ttttttttgc aatatgaccc cgtctctctg aagtgggaca ttcggacgga tggagccctc
6361 agcgtgtctt ttcagcagga gcagaaccga tgagagccgc ccttaccgtt ggtctccgga
6421 tccccagtc ccatcccgcc gttttcggct gtcttcctaa ccgtcctgtc ttctcttggc
6481 gctctttcct tccacctttc ccaagagtcc tggttgcacg ttttaagtca tatattttcg
6541 tcccctgaa aatgatggca agcccagttt ctcctgagca ttcagacccc caggccccag
6601 cacttggcgt tttcaggagg ccctgttctt agagccctg acaaaggcag cacttatttc
6661 ctgggctggt gcgccccaaa acacggcccc gacacttagt gtggccccag gcccagcga
6721 gcctcgccct cccagttttg ctctgcccag cagtgttggt gcccagagat gacaagggcc
6781 agggagcctg gcccgggtgt gagaattcag agattctggc ctccagctgt caccacaccg
6841 taacggggcc atgtaactgt gcagcatgga cagggatgcg acggggcagc tggctgtgtc
```

Figure 1 (Cont.)

```
6901 catggccagg tggccagggt cagggctgca agccaggggt ccagggccct tccgttcagc
6961 ccaaatgctg ccccaatgct aactccttgg attgtcaacc cccatccccc aaatggaaat
7021 tccgaaggag gcctcctcgc acctgccctc cgctgctcct cagacccag cccccagcga
7081 gccgacgtcc cacccgttc ctgctctcat ccccaggttg ggcacgtggg gttcctcctc
7141 tgtgggcctg gcagacctt catgagtggg acccaagata tcactgactt caacccagag
7201 gatcgagccc ctgcaccctg cctggggccc tggggtgtgg agcagtggct ggggtgggcg
7261 tggtgtggcc tgagagactg cccagctgga gaggccttcc tttacaaggc cacgcgtgca
7321 gctgtcccat ccagaccccg actggccaag acctccacgt cccagagtc cagccctgga
7381 aattccaagg gccctggcgt cctctgcctt ccccgcttcc ccatgagcgt ctgcaaaaca
7441 cttgcctgaa tacatatcac gtattttaga ctcgaagcct caaagcactg gattgtggtc
7501 ccctgccccc tctgtcccgt ccccctgccc aagtgactga aacctactga gctatattca
7561 ctgtgctgtc ctaggggag ggagagcaga gctcgcccct gcactgcagc cttgtggggg
7621 agggcaaggc tctcctccca gccaggacg ccaggacata gctgctcctg gtcagtggag
7681 gtcagccggg tatcaaaagc catgaaactg tgtctctgta gcaatgagtg atactgtgac
7741 aaaaccatcc ttgcattctt cctagaagag ttcctctgct ccttccattc cattttgtg
7801 tttgtttgt tcttttctgt cactgatccg tattaccact tttggaaaaa aataaataaa
7861 taaataaata aaaggcagct tgagtttcca aacgtgtgat tcacttgtga acaaaagtca
7921 ttctaacaat tgccttcagc gtcacgtgca ttgccactgc gctttcggca cgagggatgc
7981 tgagccctgg tgtcagagtc gtaatttaaa gcgtgtgtgt atatggactt tgtcccttaa
8041 ggtcgatata aagaatcctc gcagaatcac agacctgtgc cgcccgccac cttctgccat
8101 tgttacatta cagatttggt ttagtttgt tttgttttgt tttttctttt agaactgtat
8161 agtattgaaa aagaaatcaa atgtaaatgt ctggttttca tataatgttt aaaaagacca
8221 ttgagaagga ggctggcgct cgccccatgt ccccttgat tgtaaattgc ttctgttctg
8281 tttataagta aactgtgcat gactcctgct tagcggtcat tatcgtgtct gttggtgaaa
8341 tttttattaa aaggaaaatt ctgtagatgc acttattgaa tatgtgatta ggatctacgt
8401 ctgagactag gagtcctgaa ctgctgacgc gaaagaggcg cagttcccaa ttaatacgga
8461 aatcgctgtg ggagaagaat gaaataagac gtgaagtgta ggaaatcatg aaaagaacaa
8521 ttttgcaaat tgcattctga tgcttgtgat gaacacaaat gtacttgtgt agagacattt
8581 ccttaagaga aagcctagga gaagccgatt tggaggttaa tgctgtagaa taggactgta
8641 taccaaatgt aatctttcca atgctccaat gaatttatac atgagattga tatgcaataa
8701 atctgtgtgc ttttctaaaa aaaaaa
```
(SEQ ID NO:1)

(B)
```
  1 mrskararkl aksdgdvvnn myepnrdlla shsaedeaed samspipvgp pspfptsedf
 61 tpkegspyea pvyipedipi padfelress ipgaglgvwa krkmeagerl gpcvvvpraa
121 aketdfgweq iltdvevspq egcitkised lgsekfcvda nqagagswlk yirvacscdd
181 qnltmcqise qiyykvikdi epgeellvhv kegvyplgtv ppgldeeptf rcdecdelfq
```

Figure 1 (Cont.)

```
 241 skldlrrhkk ytcgsvgaal yeglaeelkp eglgggsgqa heckdcermf pnkysleqhm
 301 vihteereyk cdqcpkafnw ksnlirhqms hdsgkrfece ncvkvftdps nlqrhirsqh
 361 vgarahacpd cgktfatssg lkqhkhihst vkpficevch ksytqfsnlc rhkrmhadcr
 421 tqikckdcgq mfsttsslnk hrrfcegknh ytpggifapg lpltpspmmd kakpspslnh
 481 aslgfneyfp srphpgslpf stapptfpal tpgfpgifpp slyprppllp ptsllkspln
 541 htqdaklpsp lgnpalplvs avsnssqgtt aaagpeekfe srledscvek lktrssdmsd
 601 gsdfedvntt tgtdldtttg tgsdldsdvd sdpdkdkgkg ksaegqpkfg gglappgapn
 661 svaevpvfys qhsffpppde qlltatgaag dsikaiasia ekyfgpgfmg mqekklgslp
 721 yhsafpfqfl pnfphslypf tdralahnll vkaepksprd alkvggpsae cpfdlttkpk
 781 dvkpilpmpk gpsapasgee qpldlsigsr arasqnggqr eprknhvyge rklgageglp
 841 qvcparmpqq pplhyakpsp ffmdpiyrve krkvtdpvga lkekylrpsp llfhpqmsai
 901 etmteklesf aamkadsgss lqplphhpfn frsppptlsd pilrkgkery tcrycgkifp
 961 rsanltrhlr thtgeqpyrc kycdrsfsis snlqrhvrni hnkekpfkch lcnrcfgqqt
1021 nldrhlkkhe henapvsqhp gvltnhlgts assptsesdn halldekeds yfseirnfia
1081 nsemnqastr tekradmqiv dgsaqcpgla sekqedveee ddddleedde dslagksqdd
1141 tvspapepqa ayedeedeep aaslavgfdh trrcaedheg gllalepmpt fgkgldlrra
1201 aeeafevkdv lnstldseal khtlcrqakn qayammlsls edtplhtpsq gsldawlkvt
1261 gatsesgafh pinhl
```

(SEQ ID NO:2)

```
   1 gacaatgctg gggagatgaa gatagtgtgt ggctgcttct ggactcaagg aggaggagag
  61 agattccgcg agccgacacc atgcgatcca aggcgagggc gaggaagcta gccaaaagtg
 121 acggtgacgt tgtaaataat atgtatgagc ccaaccggga cctgctggcc agccacagcg
 181 cggaggacga ggccgaggac agtgccatgt cgcccatccc cgtggggcca ccgtcccct
 241 tccccaccag cgaggacttc accccaagg agggctcgcc gtacgaggcc cctgtctaca
 301 ttcctgaaga cattccgatc ccagcagact tcgagctccg agagtcctcc atcccagggg
 361 ctggcctggg ggtctggcc aagaggaaga tggaagccgg ggagaggctg ggccctgcg
 421 tggtggtgcc ccgggcggcg gcaaaggaga cagacttcgg atgggagcaa atactgacgg
 481 acgtggaagt gtcgccccag gaaggctgca tcacaaagat ctccgaagac ctgggcagtg
 541 agaagttctg cgtggatgca aatcaggcgg gggctggcag ctggctcaag tacatccgtg
 601 tggcgtgctc ctgcgatgac cagaacctca ccatgtgtca gatcagtgag cagatttact
 661 ataaagtcat taaggacatt gagccaggtg aggagctgct ggtgcacgtg aaggaaggcg
 721 tctaccccct gggcacagtg ccgcccggcc tggacgagga gcccacgttc cgctgtgacg
 781 agtgtgacga actcttccag tccaagctgg acctgcggcg ccataagaag tacacgtgtg
 841 gctcagtggg ggctgcgctc tacgagggcc tggctgagga gctcaagccc gagggccttg
 901 gcggtggcag cggccaagcc cacgagtgca aggactgcga gcggatgttc cccaacaagt
 961 acagcctgga gcagcacatg gtcatccaca cggaggagcg cgagtacaaa tgcgaccagt
1021 gtcccaaggc cttcaactgg aagtccaacc tcatccgcca ccagatgtcc cacgacagcg
1081 gcaaacgctt cgaatgtgaa aactgcgtga aggtgttcac ggaccccagc aaccttcagc
1141 ggcacatccg ctcgcagcac gtgggcgctc gggcccacgc ctgccccgac tgcgggaaga
1201 ccttcgccac gtcctccggc ctcaagcagc acaagcatat ccacagcacg gtgaagcctt
1261 tcatatgtga ggtctgccac aagtcctaca cgcagttctc caacctgtgc cggcacaagc
1321 ggatgcacgc cgactgccgc acgcagatca agtgcaagga ctgtggccag atgttcagca
1381 ctacctcctc cctcaacaag caccggcgct ctgcgaggg caagaaccat tacacgccgg
1441 gcggcatctt gcccgggc ctgcccttga cccccagccc catgatggac aaggcaaaac
1501 cctcccccag cctcaatcac gccagcctgg gcttcaacga gtactttccc tccaggccgc
1561 acccggggag cctgcccttc tccacggcgc ctcccacgtt ccccgcactc accccggct
1621 tcccgggcat cttccctcca tccttgtacc cggccgcc tctgctacct cccacatcgc
1681 tgctcaagag cccctgaac cacacccagg acgccaagct ccccagtccc ctggggaacc
1741 cagccctgcc cctggtctcc gccgtcagca cagcagcca gggcacgacg gcagctgcgg
1801 ggcccgagga gaagttcgag agccgcctgg aggactcctg tgtggagaag ctgaagacca
1861 ggagcagcga catgtcggac ggcagtgact ttgaggacgt caacaccacc acggggaccg
1921 acctggacac gaccacgggg acgggctcgg acctggacag cgacgtggac agcgaccctg
1981 acaaggacaa gggcaagggc aagtccgccg agggccagcc caagtttggg gcggcttgg
2041 cgccccgggg ggccccgaac agcgtggccg aggtgcctgt cttctattcc cagcactcat
2101 tcttcccgcc acccgacgag cagctgctga ctgcaacggg cgccgccggg gactccatca
2161 aggccatcgc atccattgcc gagaagtact ttggccccgg cttcatgggg atgcaggaga
```

Figure 2 (Cont.)

```
2221 agaagctggg ctcgctcccc taccactcgg cgttcccctt ccagttcctg cccaacttcc
2281 cccactccct ttaccccttc acggaccgag ccctcgccca caacttgctg gtcaaggccg
2341 agccaaagtc accccgggac gccctcaagg tgggcggccc cagtgccgag tgcccctttg
2401 atctcaccac caagcccaaa gacgtgaagc ccatcctgcc catgcccaag ggcccctcgg
2461 cccccgcatc cggcgaggag cagccgctgg acctgagcat cggcagccgg gcccgtgcca
2521 gccaaaacgg cggcgggcgg gagccccgca agaaccacgt ctatgggaa cgcaagctgg
2581 gcgccggcga ggggctgccc caggtgtgcc cggcgcggat gccccagcag ccccgctcc
2641 actacgccaa gccctcgccc ttcttcatgg accccatcta cagggtagaa aagcggaagg
2701 tcacagaccc cgtgggagcc ctgaaggaga agtacctgcg gccgtccccg ctgctcttcc
2761 accccagat gtcagccata gagaccatga cagagaagct ggagagcttt gcagccatga
2821 aggcggactc gggcagctcc ctgcagcccc tcccccacca cccccttcaac ttccggtccc
2881 cacccccaac gctctccgac ccatcctca ggaagggcaa ggagcgatac acgtgcaggt
2941 actgtgggaa gatcttcccc agatcagcca atctcaccag acacctgagg acgcacactg
3001 gggagcagcc gtacaggtgt aagtactgcg accgctcctt cagcatctct tcgaacctcc
3061 agcggcacgt ccggaacatc cacaacaagg agaagccttt caagtgccac ctgtgcaacc
3121 gctgcttcgg gcagcagacc aacctggacc ggcacctcaa gaagcacgag cacgagaacg
3181 caccagtgag ccagcacccc ggggtcctca cgaaccacct ggggaccagc gcgtcctctc
3241 ccacctcaga gtcggacaac cacgcacttt tagacgagaa agaagactct tatttctcgg
3301 aaatcagaaa ctttattgcc aatagtgaga tgaaccaagc atcaacgcga acagagaaac
3361 gggcggacat gcagatcgtg gacggcagtg cccagtgtcc aggcctagcc agtgagaagc
3421 aggaggacgt ggaggaggag gacgacgatg acctggagga ggacgatgag gacagcctgg
3481 ccgggaagtc gcaggatgac accgtgtccc ccgcacccga gccccaggcc gcctacgagg
3541 atgaggagga tgaggagcca gccgcctccc tggccgtggg ctttgaccac acccgaaggt
3601 gtgctgagga ccacgaaggc ggtctgttag ctttggagcc gatgccgact tttgggaagg
3661 ggctggacct ccgcagagca gctgaggaag catttgaagt taaagatgtg cttaattcca
3721 ccttagattc tgaggcttta aaacatacac tgtgcaggca ggctaagaac cagggttctc
3781 tggacgcttg gttgaaggtc actggagcca cgtcggagtc tggagcattt cacccccatca
3841 accacctctg acgggctggg cagccggggg ccggtggcca gagcgagggc accagccacg
3901 aaggacggag gcgggcgggg ccccggagaa ccctgtccct gcgtgtggcc actcctcagc
3961 atcctcccca ccaccatgg ttcattccga cttttccaat ggaaactcag atcccaaaag
4021 tccctaaagc agtcgtagag tctcaccatc tccaaggatt ggtcttgaga acactgttca
4081 gtgacggcca tgcaggtggc cgtccaaaga cagccaacgg agctgcctcg cagaatcagc
4141 cagtgggcag gtggacgctc tgctgagaca gaagctggtg ccactgccg ggtgcccgcg
4201 tggggtcgcg gaagggaatg gatagactgg tgtgctcaaa agagagagat cactcaaatg
4261 atttttataa tgaaatgaca agaataaccc ttttggtaac cgtattgact gcagagtcta
4321 ttaagcatg tggttttaaa aatagacagt attttttaaa aatcaaaaaa tgacttgcaa
4381 attgtttttt aaaagtaatt ttgcattgct ttgaaatttg agctcatttg caacccgag
4441 tctgcctggg aacccgcact gtgcctggt gtattcttta tactgtagat aatggagaaa
4501 ttttctatct ctgtccctat ttgtataagc caaggtgatg ctgggtgccc cgaggcagaa
```

Figure 2 (Cont.)

```
4561 caagaggcgc ggggccacac ccgtgaacca tgcagacggc cgaagaagtc ttaggcaggg
4621 cgccctgggc tgcaggcctg cccgaggctg ggatgggaag tgtgcctgcc ctcgtgtgac
4681 atggaattgg tgtcaggacc gccacgtggc cttcagagga atccacaggt ccccacccaa
4741 gatccctcaa ttatatgggg aagtcgaggg cctgtggctt ggatccgcca tgcagagatg
4801 tggccgggca cccatcttcc ttccctcctc tgtccctgcc tcggccaccc cacgcgggaa
4861 cccagcgccg tcctctgaag gcagggcctt ggccacgtcc tgggtctccc acctcccacc
4921 tgaccccagc ggctccggtg tcctccacgt ggctgccctg gggagcaatc ccagcggatc
4981 gctccgggcc accaagccgc acctgtgcct gagactccgg atggacgaca cagtcgtcac
5041 gtcgctcttc ctgcgggttc ttggcgagac acagcttgag aacagaaggg cgtcggggga
5101 acctgccgca aggagcagag acagcacagc ccccgggcc agccgcctc cctctcttgg
5161 gacgcaactt cttccccact cggatgggct ttaaattatt cccatagggg ccaatttcaa
5221 ataataattt ttttccctga tggaatttac cttaatctgt ataaacttg taatttttc
5281 taattcattt cttttcttat tttatttcct ccttaacagt attttggca ttagacattc
5341 ttattgtgaa gaaataatgt taatataagt atctggtgaa ggaccaaaac cgtgtgataa
5401 ggttgtgtgt cgtgtgggag tggggcgatt ttttatgtgc caaataccccc cgtccccccc
5461 atgaatcctg ctgtccctgc tgccgtttac cagacaatca tatgttttg ttaaatttgc
5521 gtttcagtta catttgcatt taagacaagt gttctattta tttcttgtat tgtttggaag
5581 aaaaaatgat gatagagtcc caaaagaag agaaaaaaaa tgcccaagtt gcccttaaa
5641 aaaaagagc gtaaatacaa acaggagtgg tgcaagccgc cttggtgtgg gtttgtgtca
5701 cgtgtggaca tctcctcagg ctttgtgtca cgcgtggaca tctcctcagg ctgtccccag
5761 cggtgacggg aggtgtcctg gctgctccag gacaaaagac aatcgtctct gtgggtgccg
5821 ggtggtccag gcttgcactg aagacgtgcc acggggaggc tcctgcagga ggctcaaccc
5881 gacggatcac agtgaaaggg attcctccca cgccagatct gcacaacgag gcaagacagg
5941 acccacctgt gcgtgcgctg gggccatggg gtggcccgc cggggcagcg ggggagctgc
6001 ctgcagaaga gccagctggc gtgtcgggaa ggatccagga tctgcaaaca caactgctca
6061 ggccttctca cgcgtttcca caacatcccc tgggtcagac ccaccaggta ccccgtagga
6121 atttccagtt tcccttgatc tagatgggat tcttataaaa attcaacctc agacataaac
6181 accccatttc tgtaaaccca aattatatgg tttcttctgc gaaagagtaa ggtgtgtgct
6241 ttttttttt tgcaatatga ccccgtctct ctgaagtggg acattcggac ggatggagcc
6301 ctcagcgtgt cttttcagca ggagcagaac cgatgagagc cgccttacc gttggtctcc
6361 ggatccccca gtcccatccc gccgttttcg gctgtcttcc taaccgtcct gtcttctctt
6421 ggcgctcttt ccttccacct ttcccaagag tcctggttgc acgttttaag tcatatattt
6481 tcgtcccct gaaaatgatg gcaagcccag tttctcctga gcattcagac ccccaggccc
6541 cagcacttgg cgttttcagg aggccctgtt cttagagccc ctgacaaagg cagcacttat
6601 ttcctgggct ggtgcgcccc aaaacacggc cccgacactt agtgtggccc caggccccag
6661 cgagcctcgc cctcccagtt ttgctctgcc cagcagtgtt ggtgcccaga tgacaagg
6721 gccagggagc ctggcccggg tgtgagaatt cagagattct ggcctccagc tgtcaccaca
6781 ccgtaacggg gccatgtaac tgtgcagcat ggacagggat gcgacgggc agctggctgt
6841 gtccatggcc aggtggccag ggtcagggct gcaagccagg ggtccagggc ccttccgttc
```

Figure 2 (Cont.)

```
6901 agcccaaatg ctgccccaat gctaactcct tggattgtca accccatcc cccaaatgga
6961 aattccgaag gaggcctcct cgcacctgcc ctccgctgct cctcagaccc cagcccccag
7021 cgagccgacg tccccacccg ttcctgctct catcccagg ttgggcacgt ggggttcctc
7081 ctctgtgggc ctggcagacc cttcatgagt gggacccaag atatcactga cttcaaccca
7141 gaggatcgag ccctgcacc ctgcctgggg ccctggggtg tggagcagtg gctggggtgg
7201 gcgtggtgtg gcctgagaga ctgcccagct ggagaggcct tcctttacaa ggccacgcgt
7261 gcagctgtcc catccagacc ccgactggcc aagacctcca cgtccccaga gtccagccct
7321 ggaaattcca agggccctgg cgtcctctgc cttccccgct tccccatgag cgtctgcaaa
7381 acacttgcct gaatacatat cacgtatttt agactcgaag cctcaaagca ctggattgtg
7441 gtccctgcc ccctctgtcc cgtcccctg cccaagtgac tgaaacctac tgagctatat
7501 tcactgtgct gtcctagggg gagggagagc agagctcgcc cctgcactgc agccttgtgg
7561 gggagggcaa ggctctcctc ccagccaggg acgccaggac atagctgctc ctggtcagtg
7621 gaggtcagcc gggtatcaaa agccatgaaa ctgtgtctct gtagcaatga gtgatactgt
7681 gacaaaacca tccttgcatt cttcctagaa gagttcctct gctccttcca ttccattttt
7741 gtgtttgttt tgttcttttc tgtcactgat ccgtattacc acttttggaa aaaaataaat
7801 aaataaataa ataaaaggca gcttgagttt ccaaacgtgt gattcacttg tgaacaaaag
7861 tcattctaac aattgccttc agcgtcacgt gcattgccac tgcgctttcg gcacgaggga
7921 tgctgagccc tggtgtcaga gtcgtaattt aaagcgtgtg tgtatatgga ctttgtccct
7981 taaggtcgat ataagaatc ctcgcagaat cacagacctg tgccgcccgc caccttctgc
8041 cattgttaca ttacagattt ggtttagttt tgttttgttt tgtttttct tttagaactg
8101 tatagtattg aaaagaaat caaatgtaaa tgtctggttt tcatataatg tttaaaaaga
8161 ccattgagaa ggaggctggc gctcgcccca tgtcccctt gattgtaaat gcttctgtt
8221 ctgtttataa gtaaactgtg catgactcct gcttagcggt cattatcgtg tctgttggtg
8281 aaattttat taaaaggaaa attctgtaga tgcacttatt gaatatgtga ttaggatcta
8341 cgtctgagac taggagtcct gaactgctga cgcgaaagag gcgcagttcc caattaatac
8401 ggaaatcgct gtgggagaag aatgaaataa gacgtgaagt gtaggaaatc atgaaaagaa
8461 caattttgca aattgcattc tgatgcttgt gatgaacaca aatgtacttg tgtagagaca
8521 tttccttaag agaaagccta ggagaagccg atttggaggt taatgctgta gaataggact
8581 gtataccaaa tgtaatcttt ccaatgctcc aatgaattta tacatgagat tgatatgcaa
8641 taaatctgtg tgcttttcta aaaaaaaa
```

(SEQ ID NO:3)

(B)

```
  1 mrskararkl aksdgdvvnn myepnrdlla shsaedeaed samspipvgp pspfptsedf
 61 tpkegspyea pvyipedipi padfelress ipgaglgvwa krkmeagerl gpcvvvpraa
121 aketdfgweq iltdvevspq egcitkised lgsekfcvda nqagagswlk yirvacscdd
181 qnltmcqise qiyykvikdi epgeellvhv kegvyplgtv ppgldeeptf rcdecdelfq
241 skldlrrhkk ytcgsvgaal yeglaeelkp eglgggsgqa heckdcermf pnkysleqhm
```

Figure 2 (Cont.)

```
 301 vihteereyk cdqcpkafnw ksnlirhqms hdsgkrfece ncvkvftdps nlqrhirsqh
 361 vgarahacpd cgktfatssg lkqhkhihst vkpficevch ksytqfsnlc rhkrmhadcr
 421 tqikckdcgq mfsttsslnk hrrfcegknh ytpggifapg lpltpspmmd kakpspslnh
 481 aslgfneyfp srphpgslpf stapptfpal tpgfpgifpp slyprppllp ptsllkspln
 541 htqdaklpsp lgnpalplvs avsnssqgtt aaagpeekfe srledscvek lktrssdmsd
 601 gsdfedvntt tgtdldtttg tgsdldsdvd sdpdkdkgkg ksaegqpkfg gglappgapn
 661 svaevpvfys qhsffpppde qlltatgaag dsikaiasia ekyfgpgfmg mqekklgslp
 721 yhsafpfqfl pnfphslypf tdralahnll vkaepksprd alkvgqpsae cpfdlttkpk
 781 dvkpilpmpk gpsapasgee qpldlsigsr arasqnggr eprknhvyge rklgageglp
 841 qvcparmpqq pplhyakpsp ffmdpiyrve krkvtdpvga lkekylrpsp llfhpqmsai
 901 etmteklesf aamkadsgss lqplphhpfn frsppptlsd pilrkgkery tcrycgkifp
 961 rsanltrhlr thtgeqpyrc kycdrsfsis snlqrhvrni hnkekpfkch lcnrcfgqqt
1021 nldrhlkkhe henapvsqhp gvltnhlgts assptsesdn halldekeds yfseirnfia
1081 nsemnqastr tekradmqiv dgsaqcpgla sekqedveee ddddleedde dslagksqdd
1141 tvspapepqa ayedeedeep aaslavgfdh trrcaedheg gllalepmpt fgkgldlrra
1201 aeeafevkdv lnstldseal khtlcrqakn qgsldawlkv tgatsesgaf hpinhl
```

(SEQ ID NO:4)

```
   1 gaattcatgc gatccaaggc aagggcgaag aagctagcca aaagtgacgg tgacgttgta
  61 aataatatgt atgaacctga cccggacctg ctggccggcc agagtgccga ggaggagacc
 121 gaagacggca tcctgtcccc catccccatg gggccaccgt cccccttccc caccagcgag
 181 gacttcactc ccaaggaggg ctcgccctat gaggctcctg tctacattcc tgaagacatt
 241 ccaatcccac cagacttcga gctacgagag tcctccatac caggagctgg cctggggatc
 301 tgggccaagc ggaagatgga aatcggggag aggtttggcc cctacgtggt gacgcccgg
 361 gccgcactga aggaggccga ctttggatgg gagatgctga cggatacaga ggtgtcatcc
 421 caggagagct gcatcaaaaa gcagatctct gaagacttgg gtagcgagaa gttctgcgtg
 481 gatgccaatc aggcgggtc tggcagctgg ctcaagtaca tccgtgtagc gtgttcctgt
 541 gatgaccaaa acctcgccat gtgtcagatc aacgaacaga tttactataa agtcattaag
 601 gacatcgagc ctggagagga actgttggtg catgtgaaag aaggtgccta ctccttggt
 661 gtcatggccc ccagcttgga tgaggacccc acattccgct gtgatgagtg tgatgagctc
 721 ttccagtgca ggctggacct gaggcgccac aagaagtacg cgtgcagctc tgcaggagcc
 781 cagctctacg agggcctagg ggaggaactc aagcccgagg ccttggcgt gggcagcgac
 841 gggcaagcgc atgagtgcaa ggattgcgag cggatgttcc ccaacaagta cagcttggag
 901 caacacatga tcgtccacac ggaagagcgt gagtacaaat gtgaccagtg tcccaaggcc
 961 ttcaactgga agtccaacct catccgccac cagatgtctc acgacagtgg caagcgcttc
1021 gaatgtgaaa actgtgtcaa ggtgttcacg gaccccagca acctccagcg tcacatccgc
1081 tcacagcatg tcggtgcccg ggcccatgcc tgccctgact gtggcaagac cttcgccaca
1141 tcctctggcc tcaaacagca caagcatatc cacagcacgg tgaagccatt catatgcgag
1201 gtctgccaca agtcctacac gcagttctcc aacctgtgcc ggcacaagcg gatgcacgcc
1261 gactgcagga cgcagatcaa gtgcaaggac tgtgggcaga tgttcagcac tacctcctcc
1321 ctcaacaagc atcggagatt ctgcgagggc aagaaccatt acacgcctgg cagcatcttc
1381 accccaggcc tgcccttgac ccccagcccc atgatggaca agacaaaacc ctccccgacc
1441 ctcaaccacg ggggcctagg cttcagcgag tacttcccct ccagacctca tcctgggagc
1501 ctgcccttct cggctgctcc tcggccttc cccacactca ctccgggctt cccgggcatc
1561 tttcctccat ccctgtaccc acgaccacct ctgctacctc ccacgccgct gctcaagagc
1621 cccctgaacc acgcgcagga cgccaagcta cccagcccgc tgggaaaccc agccctgccc
1681 cttgtctccg cggtcagcaa tagcagccag ggtgccacag cggccaccgg gtcagaggag
1741 aaatttgatg gccgcttgga agacgcatat gcggagaagg tcaaaaatag gagccctgac
1801 atgtcggacg gcagtgactt tgaggatatc aacaccacga ccgggacaga cttggacact
1861 accacgggca cggggtcaga cctggacagc gacctggaca gtgacagaga caaaggcaag
1921 gacaagggga agccagtgga gagcaaacct gagtttgggg gtgcatctgt gcccctggg
1981 gccatgaaca gtgtggccga ggtaccggcc ttctactcac agcattcctt cttcccgcca
2041 cccgaggaac agctgctgac ggcctcggga gctgccggcg actccatcaa ggccatcgcg
2101 tccatcgcgg agaaatactt cgatcctggc ttcatgagca tgcaggagaa gaagctgggc
2161 tcactaccct accactccgt gttccccttc agttcctgc ttaactttcc ccactccctc
```

Figure 3 (Cont.)

```
2221 tacccctttta cggaccgagc cctcgcccac aacttgctgg tcaaggctga gccaaagtca
2281 ccccaggatg ccctcaaggt gggcggcccc agtgcggagt gccccttcga cctcaccacc
2341 aaaccaaaag aggccaaacc cgccctgctc gcacccaagg tcccctcat cccctcatct
2401 ggcgaggaac agccactgga cctgagcatc ggcagcaggg ccagggcaag ccagaacgga
2461 ggtggccgtg agccgcggaa gaaccacgtc tacggtgaac ggaagccggg ggtcagcgag
2521 gggctgccta aggtgtgccc agcacagctg ccccagcagc cctccttgca ttatgctaag
2581 ccttcaccgt tcttcatgga tcccatctac agggtagaaa agcggaaggt ggcagaccct
2641 gtgggagtcc tgaaagagaa gtacctgcgg ccgtccccac ttctgttcca cccccagatg
2701 tcagccatag aaaccatgac ggagaagctg gagagctttg cagccatgaa ggccgactca
2761 ggcagctccc tgcagccccct gcctcaccac ccgttcaact tccgctcccc accccaacg
2821 ctctcggatc ccatcctcag gaaggggaag gagagataca cgtgcaggta ctgtggcaag
2881 atcttcccca gatctgcaaa tctcacaaga catctgagga cacacacagg ggagcagcca
2941 tacaggtgca agtactgtga ccggtcattc agcatctcct ccaacctcca gcggcacgtg
3001 aggaacatcc acaacaaaga gaagccgttc aagtgccatc tgtgcaaccg ctgcttcggg
3061 cagcagacca acctagaccg gcacctgaag aagcacgaac acgagggcgc accagtgagc
3121 cagcactccg gggtgctcac gaaccacctg ggcaccagcg cctcctcccc cacctccgag
3181 tcggacaacc atgcactttt agatgagaag gaagattctt acttctccga gatccgaaac
3241 ttcatcgcca acagcgagat gaaccaggca tccactcgaa tggacaaacg gcctgagatc
3301 caagacctgg acagcaaccc accgtgtcca ggctcagcca gtgcaaagcc agaggacgta
3361 gaggaggagg aagaggagga gctggaggaa gaggatgatg acagcttagc cgggaagtca
3421 caggaggaca cggtgtcccc cacacctgag ccccaaggag tctatgaaga tgaagaggat
3481 gaggaaccac ccagcctgac catgggcttt gaccataccc ggaggtgtgt tgaggagcga
3541 ggaggcggcc tgttagcttt ggagccgacg ccgacctttg ggaagggggct ggatctccgc
3601 agagcagctg aggaagcatt tgaagttaaa gatgtgctta attccacctt agattctgag
3661 gttttaaaac aaaccctgta caggcaggct aagaaccagg catatgcaat gatgctgtcc
3721 ctctctgaag acactcctct ccacgccccc tcccagagct cactggatgc ttggttgaac
3781 atcacaggac cctcgtcaga gtccggagcc tttaaccccca tcaaccacct ctgaggtcct
3841 ggaggcccca gggccagagt ccaaagccag ggtaccagct gcaggagatg gagaaggggc
3901 cagggagcag cccccccaccc tcaacacctc cactttgcaa agtccagctt ctccattgaa
3961 actcagaacc cgaaggtccc tcgagtagcc gctggccttc atcacctctc tgaactggcc
4021 tcaaggacac gatctgcagt gggtgcggtg cacgggccac ccaggagctg ctcacaggag
4081 ccgtggatca gaaaactcgt gggcaagggt ggggtctcta tcccagcagg agccagttgg
4141 ccacatccag gcaactgcat ggtatgaaag aggaaatcag aaagacgtgg gcaagtgcta
4201 tggagagaga cctcatcaat gattttata atgagaatca catgattaag ccttttggta
4261 atcttattga ctatagagtc tatttaagca tgtgggtttt aaaaaaaata gacggtattt
4321 tttaaaaatc
```

(SEQ ID NO:5)

```
   1 mrskarakkl aksdgdvvnn myepdpdlla gqsaeeeted gilspipmgp pspfptsedf
  61 tpkegspyea pvyipedipi ppdfelress ipgaglgiwa krkmeigerf gpyvvtpraa
 121 lkeadfgwem ltdtevssqe scikkqised lgsekfcvda nqagsgswlk yirvacscdd
 181 qnlamcqine qiyykvikdi epgeellvhv kegayslgvm apsldedptf rcdecdelfq
 241 crldlrrhkk yacssagaql yeglgeelkp eglgvgsdgq aheckdcerm fpnkysleqh
 301 mivhteerey kcdqcpkafn wksnlirhqm shdsgkrfec encvkvftdp snlqrhirsq
 361 hvgarahacp dcgktfatss glkqhkhihs tvkpficevc hksytqfsnl crhkrmhadc
 421 rtqikckdcg qmfsttssln khrrfcegkn hytpgsiftp glpltpspmm dktkpsptln
 481 hgglgfseyf psrphpgslp fsaappafpt ltpgfpgifp pslyprppll pptpllkspl
 541 nhaqdaklps plgnpalplv savsnssqga taatgseekf dgrledayae kvknrspdms
 601 dgsdfedint ttgtdldttt gtgsdldsdl dsdrdkgkdk gkpveskpef ggasvppgam
 661 nsvaevpafy sqhsffpppe eqlltasgaa gdsikaiasi aekyfdpgfm smqekklgsl
 721 pyhsvfpfqf llnfphslyp ftdralahnl lvkaepkspq dalkvggpsa ecpfdlttkp
 781 keakpallap kvplipssge eqpldlsigs rarasqnggg reprknhvyg erkpgvsegl
 841 pkvcpaqlpq qpslhyakps pffmdpiyrv ekrkvadpvg vlkekylrps pllfhpqmsa
 901 ietmtekles faamkadsgs slqplphhpf nfrsppptls dpilrkgker ytcrycgkif
 961 prsanltrhl rthtgeqpyr ckycdrsfsi ssnlqrhvrn ihnkekpfkc hlcnrcfgqq
1021 tnldrhlkkh ehegapvsqh sgvltnhlgt sassptsesd nhalldeked syfseirnfi
1081 ansemnqast rmdkrpeiqd ldsnppcpgs asakpedvee eeeeeleeed ddslagksqe
1141 dtvsptpepq gvyedeedee ppsltmgfdh trrcveergq qlllaleptpt fgkgldlrra
1201 aeeafevkdv lnstldsevl kqtlyrqakn qayammlsls edtplhapsq ssldawlnit
1261 gpssesgafn pinhl
```
(SEQ ID NO:6)

Figure 4
A 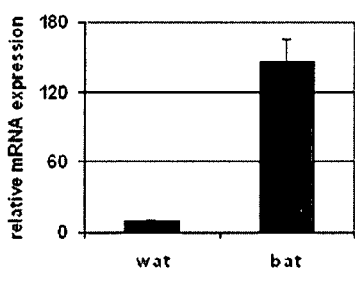 B 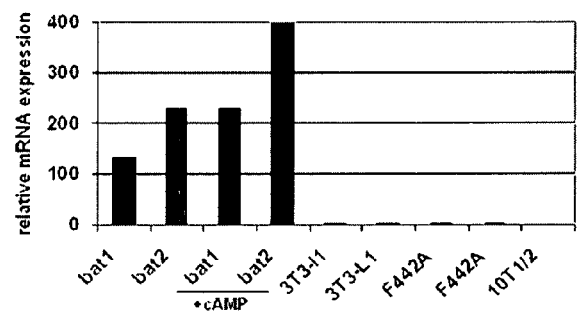
C 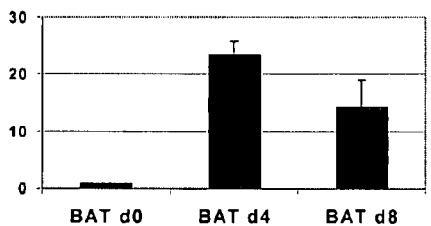 D 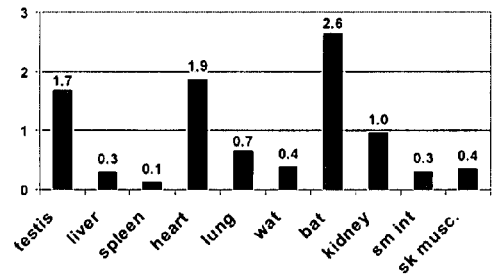

Figure 5
A
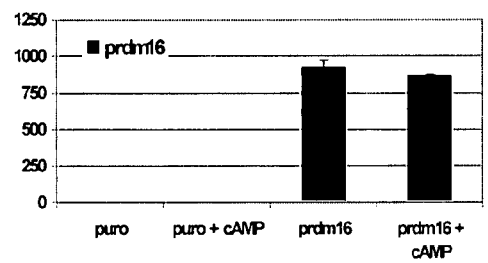
B
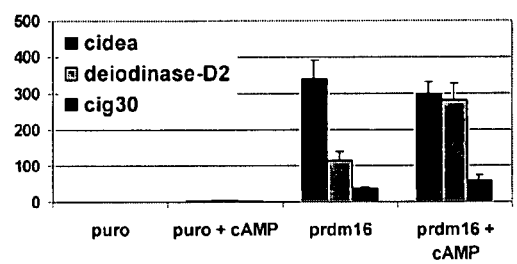
C
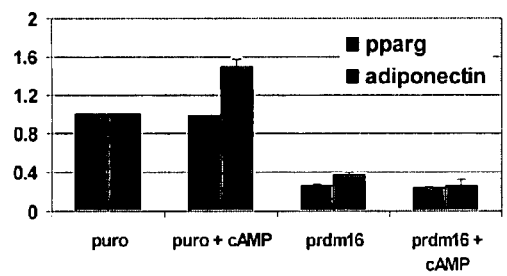
D
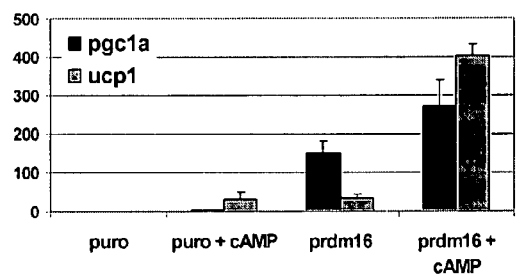

cAMP regulated brown fat cell genes are highly induced in prdm16-expressing fat cells Figure 10
A
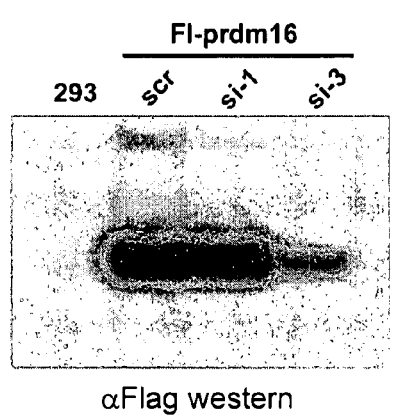
αFlag western
B
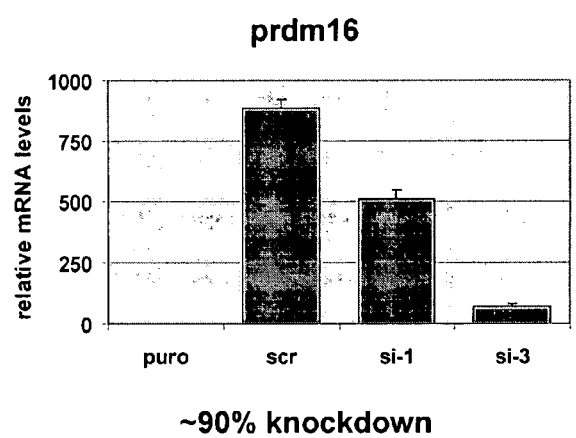
~90% knockdown

Reduced expression of brown fat cell markers in prdm16-depleted primary brown fat cultures

Prdm16 induces brown fat genes in mature white adipocytes

Ectopic subcutaneous fat pad formation from implanted fibroblasts

**Brown fat markers are expressed in fat pads derived from *prdm16*-expressing fibroblasts**

Increased expression of brown fat genes in fat pads derived from prdm16-expressing fibroblasts

SEQUENCE LISTING

<160> NUMBER OF SEQ ID NOS: 90

<210> SEQ ID NO 1
<211> LENGTH: 8726
<212> TYPE: DNA
<213> ORGANISM: Homo sapiens

<400> SEQUENCE: 1

```
gacaatgctg gggagatgaa gatagtgtgt ggctgcttct ggactcaagg aggaggagag      60
agattccgcg agccgacacc atgcgatcca aggcgagggc gaggaagcta gccaaaagtg     120
acggtgacgt tgtaaataat atgtatgagc ccaaccggga cctgctggcc agccacagcg     180
cggaggacga ggccgaggac agtgccatgt cgcccatccc cgtggggcca ccgtcccct      240
tccccaccag cgaggacttc acccccaagg agggctcgcc gtacgaggcc cctgtctaca     300
ttcctgaaga cattccgatc ccagcagact tcgagctccg agagtcctcc atcccagggg     360
ctggcctggg ggtctgggcc aagaggaaga tggaagccgg ggagaggctg gcccctgcg      420
tggtggtgcc ccgggcggcg gcaaaggaga cagacttcgg atgggagcaa atactgacgg     480
acgtggaagt gtcgccccag gaaggctgca tcacaaagat ctccgaagac ctgggcagtg     540
agaagttctg cgtggatgca aatcaggcgg gggctggcag ctggctcaag tacatccgtg     600
tggcgtgctc ctgcgatgac cagaacctca ccatgtgtca gatcagtgag cagatttact     660
ataaagtcat taaggacatt gagccaggtg aggagctgct ggtgcacgtg aaggaaggcg     720
tctacccct gggcacagtg ccgcccggcc tggacgagga gccacgttc cgctgtgacg      780
agtgtgacga actcttccag tccaagctgg acctgcggcg ccataagaag tacacgtgtg     840
gctcagtggg ggctgcgctc tacgagggcc tggctgagga gctcaagccc gagggccttg     900
gcggtggcag cggccaagcc cacgagtgca aggactgcga gcggatgttc cccaacaagt     960
acagcctgga gcagcacatg gtcatccaca cggaggagcg cgagtacaaa tgcgaccagt    1020
gtcccaaggc cttcaactgg aagtccaacc tcatccgcca ccagatgtcc cacgacagcg    1080
gcaaacgctt cgaatgtgaa actgcgtga aggtgttcac ggaccccagc aaccttcagc      1140
ggcacatccg ctcgcagcac gtgggcgctc gggccacgc ctgccccgac tgcgggaaga    1200
ccttcgccac gtcctccggc ctcaagcagc acaagcatat ccacagcacg gtgaagcctt    1260
tcatatgtga ggtctgccac aagtcctaca cgcagttctc caacctgtgc cggcacaagc    1320
ggatgcacgc cgactgccgc acgcagatca agtgcaagga ctgtggccag atgttcagca    1380
ctacctcctc cctcaacaag caccggcgct tctgcgaggg caagaaccat tacacgccgg    1440
gcggcatctt tgccccgggc ctgcccttga ccccagccc catgatggac aaggcaaaac    1500
cctccccag cctcaatcac gccagcctgg gcttcaacga gtactttccc tccaggccgc     1560
acccggggag cctgccctc tccacggcgc ctccacgtt cccgcactc accccggct      1620
tcccgggcat cttccctcca tccttgtacc ccgcgccgcc tctgctacct cccacatcgc    1680
```

```
tgctcaagag cccctgaac cacacccagg acgccaagct ccccagtccc ctggggaacc   1740
cagccctgcc cctggtctcc gccgtcagca cagcagcca gggcacgacg gcagctgcgg   1800
ggcccgagga gaagttcgag agccgcctgg aggactcctg tgtggagaag ctgaagacca   1860
ggagcagcga catgtcggac ggcagtgact ttgaggacgt caacaccacc acggggaccg   1920
acctggacac gaccacgggg acgggctcgg acctggacag cgacgtggac agcgaccctg   1980
acaaggacaa gggcaagggc aagtccgccg agggccagcc caagtttggg gcggcttgg    2040
cgcccccggg ggccccgaac agcgtggccg aggtgcctgt cttctattcc cagcactcat   2100
tcttcccgcc acccgacgag cagctgctga ctgcaacggg cgccgccggg gactccatca   2160
aggccatcgc atccattgcc gagaagtact ttggccccgg cttcatgggg atgcaggaga   2220
agaagctggg ctcgctcccc taccactcgg cgttcccctt ccagttcctg cccaacttcc   2280
cccactccct ttaccccttc acggaccgag ccctcgccca aacttgctg gtcaaggccg    2340
agccaaagtc accccgggac gccctcaagg tgggcggccc cagtgccgag tgcccctttg   2400
atctcaccac caagcccaaa gacgtgaagc ccatcctgcc catgcccaag ggcccctcgg   2460
cccccgcatc cggcgaggag cagccgctgg acctgagcat cggcagccgg gcccgtgcca   2520
gccaaaacgg cggcggcgg gagccccgca agaaccacgt ctatgggaa cgcaagctgg     2580
gcgccggcga gggctgccc caggtgtgcc cggcgcggat gccccagcag ccccgctcc     2640
actacgccaa gccctcgccc ttcttcatgg acccccatcta cagggtagaa aagcggaagg   2700
tcacagaccc cgtgggagcc ctgaaggaga agtacctgcg gccgtccccg ctgctcttcc   2760
acccccagat gtcagccata gagaccatga cagagaagct ggagagcttt gcagccatga   2820
aggcggactc gggcagctcc ctgcagcccc tcccccacca ccccttcaac ttccggtccc   2880
caccccaac gctctccgac cccatcctca ggaagggcaa ggagcgatac acgtgcaggt    2940
actgtgggaa gatcttcccc agatcagcca atctcaccag acacctgagg acgcacactg   3000
gggagcagcc gtacaggtgt aagtactgcg accgctcctt cagcatctct tcgaacctcc   3060
agcggcacgt ccggaacatc cacaacaagg agaagccttt caagtgccac ctgtgcaacc   3120
gctgcttcgg gcagcagacc aacctggacc ggcacctcaa gaagcacgag cacgagaacg   3180
caccagtgag ccagcacccc ggggtcctca cgaaccacct ggggaccagc gcgtcctctc   3240
ccacctcaga gtcggacaac cacgcacttt tagacgagaa agaagactct tatttctcgg   3300
aaatcagaaa ctttattgcc aatagtgaga tgaaccaagc atcaacgcga acagagaaac   3360
gggcggacat gcagatcgtg gacggcagtg cccagtgtcc aggcctagcc agtgagaagc   3420
aggaggacgt ggaggaggag gacgacgatg acctggagga ggacgatgag gacagcctgg   3480
ccgggaagtc gcaggatgac accgtgtccc ccgcacccga gccccaggcc gcctacgagg   3540
atgaggagga tgaggagcca gccgcctccc tggccgtggg ctttgaccac acccgaaggt   3600
gtgctgagga ccacgaaggc ggtctgttag ctttggagcc gatgccgact tttgggaagg   3660
ggctggacct ccgcagagca gctgaggaag catttgaagt taaagatgtg cttaattcca   3720
ccttagattc tgaggcttta aaacatacac tgtgcaggca ggctaagaac caggcatatg   3780
caatgatgct gtcccttttcc gaagacactc ctctccacac cccctcccag ggttctctgg   3840
acgcttggtt gaaggtcact ggagccacgt cggagtctgg agcatttcac cccatcaacc   3900
acctctgacg ggctgggcag ccgggggccg gtgccagag cgagggcacc agccacgaag   3960
gacgaggcg ggcggggccc cggagaaccc tgtccctgcg tgtggccact cctcagcatc    4020
ctccccaccc accatggttc attccgactt ttccaatgga aactcagatc ccaaaagtcc   4080
```

```
ctaaagcagt cgtagagtct caccatctcc aaggattggt cttgagaaca ctgttcagtg    4140
acggccatgc aggtggccgt ccaaagacag ccaacggagc tgcctcgcag aatcagccag    4200
tgggcaggtg gacgctctgc tgagacagaa gctggtggcc actgccgggt gcccgcgtgg    4260
ggtcgcggaa gggaatggat agactggtgt gctcaaaaga gagagatcac tcaaatgatt    4320
tttataatga aatgacaaga ataacccttt tggtaaccgt attgactgca gagtctattt    4380
aagcatgtgt tttaaaaat agacagtatt ttttaaaaat caaaaaatga cttgcaaatt      4440
gttttttaaa agtaattttg cattgctttg aaatttgagc tcatttgcaa acccgagtct    4500
gcctgggaac ccgcactgtg cctgggtgta ttctttatac tgtagataat ggagaaattt    4560
tctatctctg tccctatttg tataagccaa ggtgatgctg ggtgccccga ggcagaacaa    4620
gaggcgcggg gccacacccg tgaaccatgc agacggccga agaagtctta ggcagggcgc    4680
cctgggctgc aggcctgccc gaggctggga tgggaagtgt gcctgccctc gtgtgacatg    4740
gaattggtgt caggaccgcc acgtggcctt cagaggaatc cacaggtccc cacccaagat    4800
ccctcaatta tatggggaag tcgagggcct gtggcttgga tccgccatgc agagatgtgg    4860
ccgggcaccc atcttccttc cctcctctgt ccctgcctcg gccaccccac gcgggaaccc    4920
agcgccgtcc tctgaaggca gggccttggc cacgtcctgg gtctcccacc tcccacctga    4980 cccccagcggc tccggtgtcc tccacgtggc tgccctgggg agcaatccca gcggatcgct    5040
ccgggccacc aagccgcacc tgtgcctgag actccggatg gacgacacag tcgtcacgtc    5100
gctcttcctg cggttcttg gcgagacaca gcttgagaac agaagggcgt cggggggaacc    5160 tgccgcaagg agcagagaca gcacagcccc ccgggcccag ccgcctccct ctcttgggac    5220
gcaacttctt ccccactcgg atgggcttta aattattccc ataggggcca atttcaaata    5280
ataatttttt tccctgatgg aatttacctt aatctgtata taacttgtaa tttttttctaa    5340 ttcatttctt ttcttatttt atttcctcct taacagtatt tttggcatta gacattctta    5400
ttgtgaagaa ataatgttaa tataagtatc tggtgaagga ccaaaaccgt gtgataaggt    5460
tgtgtgtcgt gtgggagtgg ggcgattttt tatgtgccaa ataccccgt cccccccatg     5520 aatcctgctg tccctgctgc cgtttaccag acaatcatat gttttttgtta aatttgcgtt    5580 tcagttacat ttgcatttaa gacaagtgtt ctatttattt cttgtattgt ttggaagaaa    5640
aaatgatgat agagtcccaa aaagaagaga aaaaaaatgc ccaagttgcc cttttaaaaa    5700
aaagagcgta aatacaaaca ggagtggtgc aagccgcctt ggtgtgggtt tgtgtcacgt    5760
gtggacatct cctcaggctt tgtgtcacgc gtggacatct cctcaggctg tccccagcgg    5820
tgacgggagg tgtcctggct gctccaggac aaaagacaat cgtctctgtg ggtgccgggt    5880
ggtccaggct tgcactgaag acgtgccacg gggaggctcc tgcaggaggc tcaacccgac    5940
ggatcacagt gaaagggatt cctcccacgc cagatctgca caacgaggca agacaggacc    6000
cacctgtgcg tgcgctgggg ccatgggtg gccccgccgg ggcagcgggg gagctgcctg    6060
cagaagagcc agctggcgtg tcgggaagga tccaggatct gcaaacacaa ctgctcaggc    6120
cttctcacgc gtttccacaa catccccctgg gtcagaccca ccaggtaccc cgtaggaatt    6180
tccagtttcc cttgatctag atgggattct tataaaaatt caacctcaga cataaacacc    6240
ccatttctgt aaacccaaat tatatggttt cttctgcgaa agagtaaggt gtgtgctttt    6300
ttttttttgc aatatgaccc cgtctctctg aagtgggaca ttcggacgga tggagccctc    6360
agcgtgtctt ttcagcagga gcagaaccga tgagagccgc ccttaccgtt ggtctccgga    6420
```

```
tcccccagtc ccatcccgcc gttttcggct gtcttcctaa ccgtcctgtc ttctcttggc    6480
gctctttcct tccaccttc  ccaagagtcc tggttgcacg ttttaagtca tatattttcg    6540
tccccctgaa aatgatggca agcccagttt ctcctgagca ttcagacccc caggccccag    6600
cacttggcgt tttcaggagg ccctgttctt agagcccctg acaaaggcag cacttatttc    6660
ctgggctggt gcgccccaaa acacggcccc gacacttagt gtggcccag  gccccagcga    6720
gcctcgccct cccagttttg ctctgcccag cagtgttggt gcccagagat gacaagggcc    6780
agggagcctg gcccgggtgt gagaattcag agattctggc ctccagctgt caccacaccg    6840
taacggggcc atgtaactgt gcagcatgga cagggatgcg acggggcagc tggctgtgtc    6900
catggccagg tggccagggt cagggctgca agccaggggt ccagggccct tccgttcagc    6960
ccaaatgctg ccccaatgct aactccttgg attgtcaacc cccatccccc aaatggaaat    7020
tccgaaggag gcctcctcgc acctgccctc cgctgctcct cagaccccag cccccagcga    7080
gccgacgtcc ccaccgttc  ctgctctcat ccccaggttg ggcacgtggg gttcctcctc    7140
tgtgggcctg gcagacccct tcatgagtgg gacccaagata tcactgactt caacccagag    7200
gatcgagccc ctgcaccctg cctggggccc tggggtgtgg agcagtggct ggggtgggcg    7260
tggtgtggcc tgagagactg cccagctgga gaggccttcc tttacaaggc cacgcgtgca    7320
gctgtcccat ccagacccg  actggccaag acctccacgt ccccagagtc cagccctgga    7380
aattccaagg gccctggcgt cctctgcctt ccccgcttcc ccatgagcgt ctgcaaaaca    7440
cttgcctgaa tacatatcac gtattttaga ctcgaagcct caaagcactg gattgtggtc    7500
ccctgccccc tctgtcccgt cccctgccc  aagtgactga aacctactga gctatattca    7560
ctgtgctgtc ctaggggag  ggagagcaga gctcgcccct gcactgcagc cttgtggggg    7620
agggcaaggc tctcctccca gccagggacg ccaggacata gctgctcctg gtcagtggag    7680
gtcagccggg tatcaaaagc catgaaactg tgtctctgta gcaatgagtg atactgtgac    7740
aaaaccatcc ttgcattctt cctagaagag ttcctctgct ccttccattc cattttgtg     7800
tttgttttgt tcttttctgt cactgatccg tattaccact tttggaaaaa aataaataaa    7860
taaataaata aaaggcagct tgagtttcca aacgtgtgat tcacttgtga acaaaagtca    7920
ttctaacaat tgccttcagc gtcacgtgca ttgccactgc gctttcggca cgagggatgc    7980
tgagccctgg tgtcagagtc gtaatttaaa gcgtgtgtgt atatggactt tgtcccttaa    8040
ggtcgatata aagaatcctc gcagaatcac agacctgtgc cgcccgccac cttctgccat    8100
tgttacatta cagatttggt ttagttttgt tttgttttgt ttttctttt  agaactgtat    8160
agtattgaaa aagaaatcaa atgtaaatgt ctggttttca tataatgttt aaaaagacca    8220
ttgagaagga ggctggcgct cgccccatgt cccccttgat tgtaaattgc ttctgttctg    8280
tttataagta aactgtgcat gactcctgct tagcggtcat tatcgtgtct gttggtgaaa    8340
tttttattaa aaggaaaatt ctgtagatgc acttattgaa tatgtgatta ggatctacgt    8400
ctgagactag gagtcctgaa ctgctgacgc gaaagaggcg cagttcccaa ttaatacgga    8460
aatcgctgtg ggagaagaat gaaataagac gtgaagtgta ggaaatcatg aaaagaacaa    8520
ttttgcaaat tgcattctga tgcttgtgat gaacacaaat gtacttgtgt agagacattt    8580
ccttaagaga aagcctagga gaagccgatt tggaggttaa tgctgtagaa taggactgta    8640
taccaaatgt aatctttcca atgctccaat gaatttatac atgagattga tatgcaataa    8700
atctgtgtgc ttttctaaaa aaaaaa                                         8726
```

```
<210> SEQ ID NO 2
<211> LENGTH: 1275
<212> TYPE: PRT
<213> ORGANISM: Homo sapiens

<400> SEQUENCE: 2

Met Arg Ser Lys Ala Arg Ala Arg Lys Leu Ala Lys Ser Asp Gly Asp
 1               5                  10                  15

Val Val Asn Asn Met Tyr Glu Pro Asn Arg Asp Leu Leu Ala Ser His
             20                  25                  30

Ser Ala Glu Asp Glu Ala Glu Asp Ser Ala Met Ser Pro Ile Pro Val
         35                  40                  45

Gly Pro Pro Ser Pro Phe Pro Thr Ser Glu Asp Phe Thr Pro Lys Glu
     50                  55                  60

Gly Ser Pro Tyr Glu Ala Pro Val Tyr Ile Pro Glu Asp Ile Pro Ile
 65                  70                  75                  80

Pro Ala Asp Phe Glu Leu Arg Glu Ser Ile Pro Gly Ala Gly Leu
                 85                  90                  95

Gly Val Trp Ala Lys Arg Lys Met Glu Ala Gly Glu Arg Leu Gly Pro
            100                 105                 110

Cys Val Val Pro Arg Ala Ala Lys Glu Thr Asp Phe Gly Trp
            115                 120                 125

Glu Gln Ile Leu Thr Asp Val Glu Val Ser Pro Gln Glu Gly Cys Ile
            130                 135                 140

Thr Lys Ile Ser Glu Asp Leu Gly Ser Glu Lys Phe Cys Val Asp Ala
145                 150                 155                 160

Asn Gln Ala Gly Ala Gly Ser Trp Leu Lys Tyr Ile Arg Val Ala Cys
                165                 170                 175

Ser Cys Asp Asp Gln Asn Leu Thr Met Cys Gln Ile Ser Glu Gln Ile
            180                 185                 190

Tyr Tyr Lys Val Ile Lys Asp Ile Glu Pro Gly Glu Leu Leu Val
            195                 200                 205

His Val Lys Glu Gly Val Tyr Pro Leu Gly Thr Val Pro Pro Gly Leu
    210                 215                 220

Asp Glu Glu Pro Thr Phe Arg Cys Asp Glu Cys Asp Glu Leu Phe Gln
225                 230                 235                 240

Ser Lys Leu Asp Leu Arg Arg His Lys Lys Tyr Thr Cys Gly Ser Val
                245                 250                 255

Gly Ala Ala Leu Tyr Glu Gly Leu Ala Glu Glu Leu Lys Pro Glu Gly
            260                 265                 270

Leu Gly Gly Gly Ser Gly Gln Ala His Glu Cys Lys Asp Cys Glu Arg
        275                 280                 285

Met Phe Pro Asn Lys Tyr Ser Leu Glu Gln His Met Val Ile His Thr
    290                 295                 300

Glu Glu Arg Glu Tyr Lys Cys Asp Gln Cys Pro Lys Ala Phe Asn Trp
305                 310                 315                 320

Lys Ser Asn Leu Ile Arg His Gln Met Ser His Asp Ser Gly Lys Arg
                325                 330                 335

Phe Glu Cys Glu Asn Cys Val Lys Val Phe Thr Asp Pro Ser Asn Leu
            340                 345                 350

Gln Arg His Ile Arg Ser Gln His Val Gly Ala Arg Ala His Ala Cys
        355                 360                 365

Pro Asp Cys Gly Lys Thr Phe Ala Thr Ser Ser Gly Leu Lys Gln His
    370                 375                 380
```

```
Lys His Ile His Ser Thr Val Lys Pro Phe Ile Cys Glu Val Cys His
385                 390                 395                 400

Lys Ser Tyr Thr Gln Phe Ser Asn Leu Cys Arg His Lys Arg Met His
            405                 410                 415

Ala Asp Cys Arg Thr Gln Ile Lys Cys Lys Asp Cys Gly Gln Met Phe
            420                 425                 430

Ser Thr Thr Ser Ser Leu Asn Lys His Arg Arg Phe Cys Glu Gly Lys
            435                 440                 445

Asn His Tyr Thr Pro Gly Gly Ile Phe Ala Pro Gly Leu Pro Leu Thr
        450                 455                 460

Pro Ser Pro Met Met Asp Lys Ala Lys Pro Ser Pro Ser Leu Asn His
465                 470                 475                 480

Ala Ser Leu Gly Phe Asn Glu Tyr Phe Pro Ser Arg Pro His Pro Gly
                485                 490                 495

Ser Leu Pro Phe Ser Thr Ala Pro Pro Thr Phe Pro Ala Leu Thr Pro
                500                 505                 510

Gly Phe Pro Gly Ile Phe Pro Pro Ser Leu Tyr Pro Arg Pro Pro Leu
            515                 520                 525

Leu Pro Pro Thr Ser Leu Leu Lys Ser Pro Leu Asn His Thr Gln Asp
530                 535                 540

Ala Lys Leu Pro Ser Pro Leu Gly Asn Pro Ala Leu Pro Leu Val Ser
545                 550                 555                 560

Ala Val Ser Asn Ser Ser Gln Gly Thr Thr Ala Ala Ala Gly Pro Glu
                565                 570                 575

Glu Lys Phe Glu Ser Arg Leu Glu Asp Ser Cys Val Glu Lys Leu Lys
            580                 585                 590

Thr Arg Ser Ser Asp Met Ser Asp Gly Ser Asp Phe Glu Asp Val Asn
            595                 600                 605

Thr Thr Thr Gly Thr Asp Leu Asp Thr Thr Thr Gly Thr Gly Ser Asp
            610                 615                 620

Leu Asp Ser Asp Val Asp Ser Asp Pro Asp Lys Asp Lys Gly Lys Gly
625                 630                 635                 640

Lys Ser Ala Glu Gly Gln Pro Lys Phe Gly Gly Gly Leu Ala Pro Pro
            645                 650                 655

Gly Ala Pro Asn Ser Val Ala Glu Val Pro Val Phe Tyr Ser Gln His
            660                 665                 670

Ser Phe Phe Pro Pro Asp Glu Gln Leu Leu Thr Ala Thr Gly Ala
            675                 680                 685

Ala Gly Asp Ser Ile Lys Ala Ile Ala Ser Ile Ala Glu Lys Tyr Phe
        690                 695                 700

Gly Pro Gly Phe Met Gly Met Gln Glu Lys Lys Leu Gly Ser Leu Pro
705                 710                 715                 720

Tyr His Ser Ala Phe Pro Phe Gln Phe Leu Pro Asn Phe Pro His Ser
                725                 730                 735

Leu Tyr Pro Phe Thr Asp Arg Ala Leu Ala His Asn Leu Leu Val Lys
            740                 745                 750

Ala Glu Pro Lys Ser Pro Arg Asp Ala Leu Lys Val Gly Gly Pro Ser
            755                 760                 765

Ala Glu Cys Pro Phe Asp Leu Thr Thr Lys Pro Lys Asp Val Lys Pro
        770                 775                 780

Ile Leu Pro Met Pro Lys Gly Pro Ser Ala Pro Ala Ser Gly Glu Glu
785                 790                 795                 800

Gln Pro Leu Asp Leu Ser Ile Gly Ser Arg Ala Arg Ala Ser Gln Asn
```

```
                805                 810                 815
Gly Gly Gly Arg Glu Pro Arg Lys Asn His Val Tyr Gly Glu Arg Lys
            820                 825                 830

Leu Gly Ala Gly Glu Gly Leu Pro Gln Val Cys Pro Ala Arg Met Pro
        835                 840                 845

Gln Gln Pro Pro Leu His Tyr Ala Lys Pro Ser Pro Phe Phe Met Asp
    850                 855                 860

Pro Ile Tyr Arg Val Glu Lys Arg Lys Val Thr Asp Pro Val Gly Ala
865                 870                 875                 880

Leu Lys Glu Lys Tyr Leu Arg Pro Ser Pro Leu Leu Phe His Pro Gln
            885                 890                 895

Met Ser Ala Ile Glu Thr Met Thr Glu Lys Leu Glu Ser Phe Ala Ala
        900                 905                 910

Met Lys Ala Asp Ser Gly Ser Ser Leu Gln Pro Leu Pro His His Pro
    915                 920                 925

Phe Asn Phe Arg Ser Pro Pro Pro Thr Leu Ser Asp Pro Ile Leu Arg
930                 935                 940

Lys Gly Lys Glu Arg Tyr Thr Cys Arg Tyr Cys Gly Lys Ile Phe Pro
945                 950                 955                 960

Arg Ser Ala Asn Leu Thr Arg His Leu Arg Thr His Thr Gly Glu Gln
            965                 970                 975

Pro Tyr Arg Cys Lys Tyr Cys Asp Arg Ser Phe Ser Ile Ser Ser Asn
        980                 985                 990

Leu Gln Arg His Val Arg Asn Ile His Asn Lys Glu Lys Pro Phe Lys
    995                 1000                1005

Cys His Leu Cys Asn Arg Cys Phe Gly Gln Gln Thr Asn Leu Asp Arg
 1010                1015                1020

His Leu Lys Lys His Glu His Glu Asn Ala Pro Val Ser Gln His Pro
1025                1030                1035                1040

Gly Val Leu Thr Asn His Leu Gly Thr Ser Ala Ser Ser Pro Thr Ser
            1045                1050                1055

Glu Ser Asp Asn His Ala Leu Leu Asp Glu Lys Glu Asp Ser Tyr Phe
        1060                1065                1070

Ser Glu Ile Arg Asn Phe Ile Ala Asn Ser Glu Met Asn Gln Ala Ser
    1075                1080                1085

Thr Arg Thr Glu Lys Arg Ala Asp Met Gln Ile Val Asp Gly Ser Ala
1090                1095                1100

Gln Cys Pro Gly Leu Ala Ser Glu Lys Gln Glu Asp Val Glu Glu Glu
1105                1110                1115                1120

Asp Asp Asp Asp Leu Glu Glu Asp Asp Glu Asp Ser Leu Ala Gly Lys
            1125                1130                1135

Ser Gln Asp Asp Thr Val Ser Pro Ala Pro Glu Pro Gln Ala Ala Tyr
        1140                1145                1150

Glu Asp Glu Glu Asp Glu Glu Pro Ala Ala Ser Leu Ala Val Gly Phe
    1155                1160                1165

Asp His Thr Arg Arg Cys Ala Glu Asp His Glu Gly Gly Leu Leu Ala
    1170                1175                1180

Leu Glu Pro Met Pro Thr Phe Gly Lys Gly Leu Asp Leu Arg Arg Ala
1185                1190                1195                1200

Ala Glu Glu Ala Phe Glu Val Lys Asp Val Leu Asn Ser Thr Leu Asp
            1205                1210                1215

Ser Glu Ala Leu Lys His Thr Leu Cys Arg Gln Ala Lys Asn Gln Ala
        1220                1225                1230
```

```
Tyr Ala Met Met Leu Ser Leu Ser Glu Asp Thr Pro Leu His Thr Pro
    1235                1240                1245

Ser Gln Gly Ser Leu Asp Ala Trp Leu Lys Val Thr Gly Ala Thr Ser
1250                1255                1260

Glu Ser Gly Ala Phe His Pro Ile Asn His Leu
1265                1270                1275

<210> SEQ ID NO 3
<211> LENGTH: 8669
<212> TYPE: DNA
<213> ORGANISM: Homo sapiens

<400> SEQUENCE: 3
gacaatgctg gggagatgaa gatagtgtgt ggctgcttct ggactcaagg aggaggagag      60
agattccgcg agccgacacc atgcgatcca aggcgagggc gaggaagcta gccaaaagtg     120
acggtgacgt tgtaaataat atgtatgagc ccaaccggga cctgctggcc agccacagcg     180
cggaggacga ggccgaggac agtgccatgt cgcccatccc cgtggggcca ccgtccccct     240
tccccaccag cgaggacttc acccccaagg agggctcgcc gtacgaggcc cctgtctaca     300
ttcctgaaga cattccgatc ccagcagact tcgagtccga gagtcctcc atcccagggg      360
ctggcctggg ggtctgggcc aagaggaaga tggaagccgg ggagaggctg ggcccctgcg     420
tggtggtgcc ccgggcggcg gcaaaggaga cagacttcgg atgggagcaa atactgacgg     480
acgtggaagt gtcgccccag gaaggctgca tcacaaagat ctccgaagac ctgggcagtg     540
agaagttctg cgtggatgca aatcaggcgg ggctggcag ctggctcaag tacatccgtg      600
tggcgtgctc ctgcgatgac cagaacctca ccatgtgtca gatcagtgag cagatttact     660
ataaagtcat taaggacatt gagccaggtg aggagctgct ggtgcacgtg aaggaaggcg     720
tctaccccct gggcacagtg ccgcccggcc tggacgagga gccacgttc cgctgtgacg      780
agtgtgacga actcttccag tccaagctgg acctgcggcg ccataagaag tacacgtgtg     840
gctcagtggg ggctgcgctc tacgagggcc tggctgagga gctcaagccc gagggccttg     900
gcggtggcag cggccaagcc cacgagtgca aggactgcga gcggatgttc cccaacaagt     960
acagcctgga gcagcacatg gtcatccaca cggaggagcg cgagtacaaa tgcgaccagt    1020
gtcccaaggc cttcaactgg aagtccaacc tcatccgcca ccagatgtcc cacgacagcg    1080
gcaaacgctt cgaatgtgaa aactgcgtga aggtgttcac ggaccccagc aaccttcagc    1140
ggcacatccg ctcgcagcac gtgggcgctc gggccacgc ctgccccgac tgcgggaaga     1200
ccttcgccac gtcctccggc ctcaagcagc acaagcatat ccacagcacg gtgaagcctt    1260
tcatatgtga ggtctgccac aagtcctaca cgcagttctc caacctgtgc cggcacaagc    1320
ggatgcacgc cgactgccgc acgcagatca agtgcaagga ctgtggccag atgttcagca    1380
ctacctcctc cctcaacaag caccggcgct ctgcgagggg caagaaccat acacgccgg     1440
gcggcatctt tgccccgggc ctgccccttga ccccagccc catgatggac aaggcaaaac    1500
cctcccccag cctcaatcac gccagcctgg gcttcaacga gtactttccc tccaggccgc    1560
acccggggag cctgcccttc tccacggcgc ctcccacgtt cccgcactc acccccggct     1620
tcccgggcat cttccctcca tccttgtacc ccggccgcc tctgctacct cccacatcgc     1680
tgctcaagag cccctgaac cacacccagg acgccaagct cccagtccc ctggggaacc      1740
cagccctgcc cctggtctcc gccgtcagca acagcagcca gggcacgacg gcagctgcgg    1800
ggccgagga gaagttcgag agccgcctgg aggactcctg tgtggagaag ctgaagacca    1860
```

```
ggagcagcga catgtcggac ggcagtgact ttgaggacgt caacaccacc acggggaccg    1920
acctggacac gaccacgggg acgggctcgg acctggacag cgacgtggac agcgaccctg    1980
acaaggacaa gggcaagggc aagtccgccg agggccagcc caagtttggg ggcggcttgg    2040
cgcccccggg ggccccgaac agcgtggccg aggtgcctgt cttctattcc cagcactcat    2100
tcttcccgcc acccgacgag cagctgctga ctgcaacggg cgccgccggg gactccatca    2160
aggccatcgc atccattgcc gagaagtact ttggccccgg cttcatgggg atgcaggaga    2220
agaagctggg ctcgctcccc taccactcgg cgttcccctt ccagttcctg cccaacttcc    2280
cccactccct ttacccctta cggaccgag ccctcgccca caacttgctg gtcaaggccg    2340
agccaaagtc accccgggac gccctcaagg tgggcggccc cagtgccgag tgccccttg    2400 atctcaccac caagcccaaa gacgtgaagc ccatcctgcc catgcccaag ggcccctcgg    2460
cccccgcatc cggcgaggag cagccgctgg acctgagcat cggcagccgg gcccgtgcca    2520
gccaaaacgg cggcgggcgg gagccccgca gaaccacgt ctatggggaa cgcaagctgg    2580
gcgccggcga ggggctgccc caggtgtgcc cggcgcggat gccccagcag cccccgctcc    2640
actacgccaa gccctcgccc ttcttcatgg accccatcta cagggtagaa aagcggaagg    2700
tcacagaccc cgtgggagcc ctgaaggaga agtacctgcg gccgtccccg ctgctcttcc    2760
acccccagat gtcagccata gagaccatga cagagaagct ggagagcttt gcagccatga    2820
aggcggactc gggcagctcc ctgcagcccc tcccccacca ccccttcaac ttccggtccc    2880 caccccaac gctctccgac cccatcctca ggaagggcaa ggagcgatac acgtgcaggt    2940
actgtgggaa gatcttcccc agatcagcca atctcaccag acacctgagg acgcacactg    3000
gggagcagcc gtacaggtgt aagtactgcg accgctcctt cagcatctct tcgaacctcc    3060
agcggcacgt ccggaacatc cacaacaagg agaagccttt caagtgccac ctgtgcaacc    3120
gctgcttcgg gcagcagacc aacctggacc ggcacctcaa gaagcacgag cacgagaacg    3180
caccagtgag ccagcacccc ggggtcctca cgaaccacct ggggaccagc cgtcctctc    3240 ccacctcaga gtcggacaac cacgcacttt tagacgagaa agaagactct tatttctcgg    3300
aaatcagaaa ctttattgcc aatagtgaga tgaaccaagc atcaacgcga acagagaaac    3360
gggcggacat gcagatcgtg gacggcagtg cccagtgtcc aggcctagcc agtgagaagc    3420
aggaggacgt ggaggaggag gacgacgatg acctggagga ggacgatgag gacagcctgg    3480
ccgggaagtc gcaggatgac accgtgtccc ccgcacccga gccccaggcc gcctacgagg    3540
atgaggagga tgaggagcca gccgcctccc tggccgtggg cttttgaccac acccgaaggt    3600 gtgctgagga ccacgaaggc ggtctgttag cttttggagcc gatgccgact tttgggaagg    3660
ggctggacct ccgcagagca gctgaggaag catttgaagt taaagatgtg cttaattcca    3720
ccttagattc tgaggcttta aaacatacac tgtgcaggca ggctaagaac cagggttctc    3780
tggacgcttg gttgaaggtc actggagcca cgtcggagtc tggagcattt cacccccatca    3840 accacctctg acgggctggg cagccgggg ccggtggcca gagcgagggc accagccacg    3900
aaggacggag gcgggcgggg ccccggagaa ccctgtccct gcgtgtggcc actcctcagc    3960
atcctcccca cccaccatgg ttcattccga cttttccaat ggaaactcag atcccaaaag    4020
tccctaaagc agtcgtagag tctcaccatc tccaaggatt ggtcttgaga acactgttca    4080 gtgacgcca tgcaggtggc cgtccaaaga cagccaacgg agctgcctcg cagaatcagc    4140
cagtgggcag gtggacgctc tgctgagaca gaagctggtg gccactgccg ggtgcccgcg    4200
```

```
tggggtcgcg aagggaatg gatagactgg tgtgctcaaa agagagagat cactcaaatg    4260
atttttataa tgaaatgaca agaataaccc ttttggtaac cgtattgact gcagagtcta    4320
tttaagcatg tggttttaaa aatagacagt attttttaaa aatcaaaaaa tgacttgcaa    4380 attgttttt aaaagtaatt ttgcattgct ttgaaatttg agctcatttg caaacccgag    4440
tctgcctggg aacccgcact gtgcctgggt gtattcttta tactgtagat aatggagaaa    4500
ttttctatct ctgtccctat ttgtataagc caaggtgatg ctgggtgccc cgaggcagaa    4560
caagaggcgc ggggccacac ccgtgaacca tgcagacggc cgaagaagtc ttaggcaggg    4620
cgccctgggc tgcaggcctg cccgaggctg ggatgggaag tgtgcctgcc ctcgtgtgac    4680
atggaattgg tgtcaggacc gccacgtggc cttcagagga atccacaggt ccccacccaa    4740
gatccctcaa ttatatgggg aagtcgaggg cctgtggctt ggatccgcca tgcagagatg    4800
tggccgggca cccatcttcc ttccctcctc tgtccctgcc tcggccaccc cacgcgggaa    4860
cccagcgccg tcctctgaag gcagggcctt ggccacgtcc tgggtctccc acctcccacc    4920
tgaccccagc ggctccggtg tcctccacgt ggctgccctg gggagcaatc ccagcggatc    4980
gctccgggcc accaagccgc acctgtgcct gagactccgg atggacgaca cagtcgtcac    5040
gtcgctcttc ctgcgggttc ttggcgagac acagcttgag aacagaaggg cgtcggggga    5100
acctgccgca aggagcagag acagcacagc ccccgggcc cagccgcctc cctctcttgg    5160
gacgcaactt cttccccact cggatgggct ttaaattatt cccataggg ccaatttcaa    5220 ataataattt ttttccctga tggaatttac cttaatctgt atataacttg taatttttc    5280 taattcattt ctttctttat tttatttcct ccttaacagt attttggca ttagacattc    5340 ttattgtgaa gaaataatgt taatataagt atctggtgaa ggaccaaaac cgtgtgataa    5400
ggttgtgtgt cgtgtgggag tggggcgatt ttttatgtgc caaatacccc cgtcccccc    5460 atgaatcctg ctgtccctgc tgccgtttac cagacaatca tatgttttg ttaaatttgc    5520 gtttcagtta catttgcatt taagacaagt gttctattta tttcttgtat tgtttggaag    5580
aaaaaatgat gatagagtcc caaaagaag agaaaaaaa tgcccaagtt gcccttaaa    5640 aaaaaagagc gtaaatacaa acaggagtgg tgcaagccgc cttggtgtgg gtttgtgtca    5700
cgtgtggaca tctcctcagg ctttgtgtca cgcgtggaca tctcctcagg ctgtccccag    5760 cggtgacgg aggtgtcctg gctgctccag gacaaaagac aatcgtctct gtgggtgccg    5820
ggtggtccag gcttgcactg aagacgtgcc acggggaggc tcctgcagga ggctcaaccc    5880
gacggatcac agtgaaaggg attcctccca cgccagatct gcacaacgag gcaagacagg    5940
acccacctgt gcgtgcgctg gggccatggg gtggcccgc cggggcagcg ggggagctgc    6000
ctgcagaaga gccagctggc gtgtcgggaa ggatccagga tctgcaaaca caactgctca    6060
ggccttctca cgcgtttcca caacatcccc tgggtcagac ccaccaggta ccccgtagga    6120
atttccagtt tcccttgatc tagatgggat tcttataaaa attcaacctc agacataaac    6180
accccatttc tgtaaaccca aattatatgg tttcttctgc gaaagagtaa ggtgtgtgct    6240 ttttttttt tgcaatatga ccccgtctct ctgaagtggg acattcggac ggatggagcc    6300
ctcagcgtgt cttttcagca ggagcagaac cgatgagagc cgcccttacc gttggtctcc    6360
ggatccccca gtcccatccc gccgttttcg gctgtcttcc taaccgtcct gtcttctctt    6420
ggcgctcttt ccttccacct ttcccaagag tcctggttgc acgttttaag tcatatattt    6480 tcgtcccct gaaaatgatg gcaagcccag tttctcctga gcattcagac ccccaggccc    6540
cagcacttgg cgttttcagg aggccctgtt cttagagccc ctgacaaagg cagcacttat    6600
```

```
ttcctgggct ggtgcgcccc aaaacacggc cccgacactt agtgtggccc caggccccag    6660
cgagcctcgc cctcccagtt ttgctctgcc cagcagtgtt ggtgcccaga gatgacaagg    6720
gccagggagc ctggcccggg tgtgagaatt cagagattct ggcctccagc tgtcaccaca    6780
ccgtaacggg gccatgtaac tgtgcagcat ggacagggat gcgacggggc agctggctgt    6840
gtccatggcc aggtggccag ggtcagggct gcaagccagg ggtccagggc cttccgttc     6900 agcccaaatg ctgccccaat gctaactcct tggattgtca accccatcc cccaaatgga    6960 aattccgaag gaggcctcct cgcacctgcc ctccgctgct cctcagaccc cagccccag    7020 cgagccgacg tccccacccg ttcctgctct catcccagg ttgggcacgt ggggttcctc    7080
ctctgtgggc ctggcagacc cttcatgagt gggacccaag atatcactga cttcaaccca    7140
gaggatcgag cccctgcacc ctgcctgggg ccctggggtg tggagcagtg gctggggtgg    7200
gcgtggtgtg gcctgagaga ctgcccagct ggagaggcct tcctttacaa ggccacgcgt    7260
gcagctgtcc catccagacc ccgactggcc aagacctcca cgtccccaga gtccagccct    7320
ggaaattcca agggccctgg cgtcctctgc cttccccgct tccccatgag cgtctgcaaa    7380
acacttgcct gaatacatat cacgtatttt agactcgaag cctcaaagca ctggattgtg    7440
gtcccctgcc ccctctgtcc cgtccccctg cccaagtgac tgaaacctac tgagctatat    7500
tcactgtgct gtcctagggg gagggagagc agagctcgcc cctgcactgc agccttgtgg    7560
gggagggcaa ggctctcctc ccagccaggg acgccaggac atagctgctc ctggtcagtg    7620
gaggtcagcc gggtatcaaa agccatgaaa ctgtgtctct gtagcaatga gtgatactgt    7680
gacaaaacca tccttgcatt cttcctagaa gagttcctct gctccttcca ttccattttt    7740
gtgtttgttt tgttctttc tgtcactgat ccgtattacc actttggaa aaaaataaat     7800 aaataaataa ataaaaggca gcttgagttt ccaaacgtgt gattcacttg tgaacaaaag    7860
tcattctaac aattgccttc agcgtcacgt gcattgccac tgcgctttcg gcacgaggga    7920
tgctgagccc tggtgtcaga gtcgtaattt aaagcgtgtg tgtatatgga cttttgtccct   7980 taaggtcgat ataagaaatc ctcgcagaat cacagacctg tgccgcccgc caccttctgc    8040
cattgttaca ttacagattt ggtttagttt tgttttgttt tgttttttct tttagaactg    8100
tatagtattg aaaagaaat caaatgtaaa tgtctggttt tcatataatg tttaaaaga      8160 ccattgagaa ggaggctggc gctcgcccca tgtccccctt gattgtaaat tgcttctgtt    8220
ctgtttataa gtaaactgtg catgactcct gcttagcggt cattatcgtg tctgttggtg    8280 aaattttat taaaaggaaa attctgtaga tgcacttatt gaatatgtga ttaggatcta    8340
cgtctgagac taggagtcct gaactgctga cgcgaaagag gcgcagttcc caattaatac    8400
ggaaatcgct gtgggagaag aatgaaataa gacgtgaagt gtaggaaatc atgaaaagaa    8460
caattttgca aattgcattc tgatgcttgt gatgaacaca aatgtacttg tgtagagaca    8520
tttccttaag agaaagccta ggagaagccg atttggaggt taatgctgta gaataggact    8580
gtataccaaa tgtaatcttt ccaatgctcc aatgaattta tacatgagat tgatatgcaa    8640
taaatctgtg tgcttttcta aaaaaaaaa                                     8669
```

<210> SEQ ID NO 4
<211> LENGTH: 1256
<212> TYPE: PRT
<213> ORGANISM: Homo sapiens

<400> SEQUENCE: 4

```
Met Arg Ser Lys Ala Arg Ala Arg Lys Leu Ala Lys Ser Asp Gly Asp
  1               5                  10                  15

Val Val Asn Asn Met Tyr Glu Pro Asn Arg Asp Leu Leu Ala Ser His
             20                  25                  30

Ser Ala Glu Asp Glu Ala Glu Asp Ser Ala Met Ser Pro Ile Pro Val
         35                  40                  45

Gly Pro Pro Ser Pro Phe Pro Thr Ser Glu Asp Phe Thr Pro Lys Glu
     50                  55                  60

Gly Ser Pro Tyr Glu Ala Pro Val Tyr Ile Pro Glu Asp Ile Pro Ile
 65                  70                  75                  80

Pro Ala Asp Phe Glu Leu Arg Glu Ser Ile Pro Gly Ala Gly Leu
                 85                  90                  95

Gly Val Trp Ala Lys Arg Lys Met Glu Ala Gly Glu Arg Leu Gly Pro
            100                 105                 110

Cys Val Val Pro Arg Ala Ala Lys Glu Thr Asp Phe Gly Trp
            115                 120                 125

Glu Gln Ile Leu Thr Asp Val Glu Val Ser Pro Gln Glu Gly Cys Ile
        130                 135                 140

Thr Lys Ile Ser Glu Asp Leu Gly Ser Glu Lys Phe Cys Val Asp Ala
145                 150                 155                 160

Asn Gln Ala Gly Ala Gly Ser Trp Leu Lys Tyr Ile Arg Val Ala Cys
                165                 170                 175

Ser Cys Asp Asp Gln Asn Leu Thr Met Cys Gln Ile Ser Glu Gln Ile
            180                 185                 190

Tyr Tyr Lys Val Ile Lys Asp Ile Glu Pro Gly Glu Glu Leu Leu Val
        195                 200                 205

His Val Lys Glu Gly Val Tyr Pro Leu Gly Thr Val Pro Pro Gly Leu
        210                 215                 220

Asp Glu Glu Pro Thr Phe Arg Cys Asp Glu Cys Asp Glu Leu Phe Gln
225                 230                 235                 240

Ser Lys Leu Asp Leu Arg Arg His Lys Lys Tyr Thr Cys Gly Ser Val
                245                 250                 255

Gly Ala Ala Leu Tyr Glu Gly Leu Ala Glu Glu Leu Lys Pro Glu Gly
            260                 265                 270

Leu Gly Gly Gly Ser Gly Gln Ala His Glu Cys Lys Asp Cys Glu Arg
        275                 280                 285

Met Phe Pro Asn Lys Tyr Ser Leu Glu Gln His Met Val Ile His Thr
        290                 295                 300

Glu Glu Arg Glu Tyr Lys Cys Asp Gln Cys Pro Lys Ala Phe Asn Trp
305                 310                 315                 320

Lys Ser Asn Leu Ile Arg His Gln Met Ser His Asp Ser Gly Lys Arg
                325                 330                 335

Phe Glu Cys Glu Asn Cys Val Lys Val Phe Thr Asp Pro Ser Asn Leu
            340                 345                 350

Gln Arg His Ile Arg Ser Gln His Val Gly Ala Arg Ala His Ala Cys
            355                 360                 365

Pro Asp Cys Gly Lys Thr Phe Ala Thr Ser Ser Gly Leu Lys Gln His
        370                 375                 380

Lys His Ile His Ser Thr Val Lys Pro Phe Ile Cys Glu Val Cys His
385                 390                 395                 400

Lys Ser Tyr Thr Gln Phe Ser Asn Leu Cys Arg His Lys Arg Met His
                405                 410                 415

Ala Asp Cys Arg Thr Gln Ile Lys Cys Lys Asp Cys Gly Gln Met Phe
```

```
            420             425             430
Ser Thr Thr Ser Ser Leu Asn Lys His Arg Phe Cys Glu Gly Lys
            435             440             445
Asn His Tyr Thr Pro Gly Gly Ile Phe Ala Pro Gly Leu Pro Leu Thr
    450             455             460
Pro Ser Pro Met Met Asp Lys Ala Lys Pro Ser Pro Ser Leu Asn His
465             470             475             480
Ala Ser Leu Gly Phe Asn Glu Tyr Phe Pro Ser Arg Pro His Pro Gly
                485             490             495
Ser Leu Pro Phe Ser Thr Ala Pro Pro Thr Phe Pro Ala Leu Thr Pro
            500             505             510
Gly Phe Pro Gly Ile Phe Pro Pro Ser Leu Tyr Pro Arg Pro Pro Leu
        515             520             525
Leu Pro Pro Thr Ser Leu Leu Lys Ser Pro Leu Asn His Thr Gln Asp
    530             535             540
Ala Lys Leu Pro Ser Pro Leu Gly Asn Pro Ala Leu Pro Leu Val Ser
545             550             555             560
Ala Val Ser Asn Ser Ser Gln Gly Thr Thr Ala Ala Gly Pro Glu
                565             570             575
Glu Lys Phe Glu Ser Arg Leu Glu Asp Ser Cys Val Glu Lys Leu Lys
            580             585             590
Thr Arg Ser Ser Asp Met Ser Asp Gly Ser Asp Phe Glu Asp Val Asn
        595             600             605
Thr Thr Thr Gly Thr Asp Leu Asp Thr Thr Thr Gly Thr Gly Ser Asp
    610             615             620
Leu Asp Ser Asp Val Asp Ser Asp Pro Asp Lys Asp Lys Gly Lys Gly
625             630             635             640
Lys Ser Ala Glu Gly Gln Pro Lys Phe Gly Gly Leu Ala Pro Pro
                645             650             655
Gly Ala Pro Asn Ser Val Ala Glu Val Pro Val Phe Tyr Ser Gln His
                660             665             670
Ser Phe Phe Pro Pro Pro Asp Glu Gln Leu Leu Thr Ala Thr Gly Ala
            675             680             685
Ala Gly Asp Ser Ile Lys Ala Ile Ala Ser Ile Ala Glu Lys Tyr Phe
    690             695             700
Gly Pro Gly Phe Met Gly Met Gln Glu Lys Lys Leu Gly Ser Leu Pro
705             710             715             720
Tyr His Ser Ala Phe Pro Phe Gln Phe Leu Pro Asn Phe Pro His Ser
                725             730             735
Leu Tyr Pro Phe Thr Asp Arg Ala Leu Ala His Asn Leu Leu Val Lys
            740             745             750
Ala Glu Pro Lys Ser Pro Arg Asp Ala Leu Lys Val Gly Gly Pro Ser
        755             760             765
Ala Glu Cys Pro Phe Asp Leu Thr Thr Lys Pro Lys Asp Val Lys Pro
    770             775             780
Ile Leu Pro Met Pro Lys Gly Pro Ser Ala Pro Ala Ser Gly Glu Glu
785             790             795             800
Gln Pro Leu Asp Leu Ser Ile Gly Ser Arg Ala Arg Ala Ser Gln Asn
                805             810             815
Gly Gly Gly Arg Glu Pro Arg Lys Asn His Val Tyr Gly Glu Arg Lys
            820             825             830
Leu Gly Ala Gly Glu Gly Leu Pro Gln Val Cys Pro Ala Arg Met Pro
        835             840             845
```

-continued

```
Gln Gln Pro Pro Leu His Tyr Ala Lys Pro Ser Pro Phe Met Asp
    850                 855                 860
Pro Ile Tyr Arg Val Glu Lys Arg Lys Val Thr Asp Pro Val Gly Ala
865                 870                 875                 880
Leu Lys Glu Lys Tyr Leu Arg Pro Ser Pro Leu Leu Phe His Pro Gln
                885                 890                 895
Met Ser Ala Ile Glu Thr Met Thr Glu Lys Leu Glu Ser Phe Ala Ala
                900                 905                 910
Met Lys Ala Asp Ser Gly Ser Ser Leu Gln Pro Leu Pro His His Pro
        915                 920                 925
Phe Asn Phe Arg Ser Pro Pro Thr Leu Ser Asp Pro Ile Leu Arg
930                 935                 940
Lys Gly Lys Glu Arg Tyr Thr Cys Arg Tyr Cys Gly Lys Ile Phe Pro
945                 950                 955                 960
Arg Ser Ala Asn Leu Thr Arg His Leu Arg Thr His Thr Gly Glu Gln
                965                 970                 975
Pro Tyr Arg Cys Lys Tyr Cys Asp Arg Ser Phe Ser Ile Ser Ser Asn
                980                 985                 990
Leu Gln Arg His Val Arg Asn Ile His Asn Lys Glu Lys Pro Phe Lys
                995                 1000                1005
Cys His Leu Cys Asn Arg Cys Phe Gly Gln Gln Thr Asn Leu Asp Arg
        1010                1015                1020
His Leu Lys Lys His Glu His Glu Asn Ala Pro Val Ser Gln His Pro
1025                1030                1035                1040
Gly Val Leu Thr Asn His Leu Gly Thr Ser Ala Ser Ser Pro Thr Ser
                1045                1050                1055
Glu Ser Asp Asn His Ala Leu Leu Asp Glu Lys Glu Asp Ser Tyr Phe
                1060                1065                1070
Ser Glu Ile Arg Asn Phe Ile Ala Asn Ser Glu Met Asn Gln Ala Ser
            1075                1080                1085
Thr Arg Thr Glu Lys Arg Ala Asp Met Gln Ile Val Asp Gly Ser Ala
        1090                1095                1100
Gln Cys Pro Gly Leu Ala Ser Glu Lys Gln Glu Asp Val Glu Glu Glu
1105                1110                1115                1120
Asp Asp Asp Asp Leu Glu Glu Asp Asp Glu Asp Ser Leu Ala Gly Lys
                1125                1130                1135
Ser Gln Asp Asp Thr Val Ser Pro Ala Pro Glu Pro Gln Ala Ala Tyr
            1140                1145                1150
Glu Asp Glu Glu Asp Glu Pro Ala Ala Ser Leu Ala Val Gly Phe
        1155                1160                1165
Asp His Thr Arg Arg Cys Ala Glu Asp His Glu Gly Gly Leu Leu Ala
    1170                1175                1180
Leu Glu Pro Met Pro Thr Phe Gly Lys Gly Leu Asp Leu Arg Arg Ala
1185                1190                1195                1200
Ala Glu Glu Ala Phe Glu Val Lys Asp Val Leu Asn Ser Thr Leu Asp
                1205                1210                1215
Ser Glu Ala Leu Lys His Thr Leu Cys Arg Gln Ala Lys Asn Gln Gly
            1220                1225                1230
Ser Leu Asp Ala Trp Leu Lys Val Thr Gly Ala Thr Ser Glu Ser Gly
        1235                1240                1245
Ala Phe His Pro Ile Asn His Leu
    1250                1255
```

<210> SEQ ID NO 5
<211> LENGTH: 4330
<212> TYPE: DNA
<213> ORGANISM: Mus sp.

<400> SEQUENCE: 5

```
gaattcatgc gatccaaggc aagggcgaag aagctagcca aaagtgacgg tgacgttgta      60
aataatatgt atgaacctga cccggacctg ctggccggcc agagtgccga ggaggagacc     120
gaagacggca tcctgtcccc catccccatg gggccaccgt ccccttccc caccagcgag      180
gacttcactc ccaaggaggg ctcgccctat gaggctcctg tctacattcc tgaagacatt     240
ccaatcccac cagacttcga gctacgagag tcctccatac caggagctgg cctggggatc     300
tgggccaagc ggaagatgga aatcgggagg aggtttggcc cctacgtggt gacgccccgg     360
gccgcactga aggaggccga ctttggatgg agatgctga cggatacaga ggtgtcatcc      420
caggagagct gcatcaaaaa gcagatctct gaagacttgg gtagcgagaa gttctgcgtg     480
gatgccaatc aggcggggtc tggcagctgg ctcaagtaca tccgtgtagc gtgttcctgt     540
gatgaccaaa acctcgccat gtgtcagatc aacgaacaga tttactataa agtcattaag     600
gacatcgagc ctggagagga actgttggtg catgtgaaag aaggtgccta ctccttgggt     660
gtcatggccc ccagcttgga tgaggacccc acattccgct gtgatgagtg tgatgagctc     720
ttccagtgca ggctggacct gaggcgccac aagaagtacg cgtgcagctc tgcaggagcc     780
cagctctacg agggcctagg ggaggaactc aagcccgagg ccttggcgt gggcagcgac      840
gggcaagcgc atgagtgcaa ggattgcgag cggatgttcc ccaacaagta cagcttggag     900
caacacatga tcgtccacac ggaagagcgt gagtacaaat gtgaccagtg tcccaaggcc     960
ttcaactgga gtccaacct catccgccac cagatgtctc acgacagtgg caagcgcttc    1020
gaatgtgaaa actgtgtcaa ggtgttcacg gaccccagca acctccagcg tcacatccgc    1080
tcacagcatg tcggtgcccg ggcccatgcc tgccctgact gtggcaagac cttcgccaca    1140
tcctctggcc tcaaacagca caagcatatc cacagcacgg tgaagccatt catatgcgag    1200
gtctgccaca gtcctacac gcagttctcc aacctgtgcc ggcacaagcg gatgcacgcc    1260
gactgcagga cgcagatcaa gtgcaaggac tgtgggcaga tgttcagcac tacctcctcc    1320
ctcaacaagc atcggagatt ctgcgagggc aagaaccatt acacgcctgg cagcatcttc    1380
accccaggcc tgcccttgac cccagccccc atgatggaca agacaaaacc ctcccgacc    1440
ctcaaccacg ggggcctagg cttcagcgag tacttcccct ccagacctca tcctgggagc    1500
ctgcccttct cggctgctcc tccggccttc cccacactca ctccgggctt cccgggcatc    1560
tttcctccat ccctgtaccc acgaccacct ctgctacctc ccacgccgct gctcaagagc    1620
cccctgaacc acgcgcagga cgccaagcta cccagcccgc tgggaaaccc agccctgccc    1680
cttgtctccg cggtcagcaa tagcagccag ggtgccacag cggccaccgg gtcagaggag    1740
aaatttgatg gccgcttgga agacgcatat gcggagaagg tcaaaaatag gagccctgac    1800
atgtcggacg gcagtgactt tgaggatatc aacaccacga ccgggacaga cttggacact    1860
accacgggca cggggtcaga cctggacagc gacctggaca gtgacagaga caaaggcaag    1920
gacaagggga agccagtgga gagcaaacct gagtttgggg gtgcatctgt gccccctggg    1980
gccatgaaca gtgtggccga ggtaccggcc ttctactcac agcattcctt ctttccgcca    2040
cccgaggaac agctgctgac ggcctcggga gctgccggcg actccatcaa ggccatcgcg    2100
tccatcgcgg agaaatactt cgatcctggc ttcatgagca tgcaggagaa gaagctgggc    2160
```

```
tcactaccct accactccgt gttcccnttc cagttcctgc ttaactttcc ccactccctc   2220
taccccttta cggaccgagc cctcgcccac aacttgctgg tcaaggctga gccaaagtca   2280
ccccaggatg ccctcaaggt gggcggcccc agtgcggagt gccccttcga cctcaccacc   2340
aaaccaaaag aggccaaacc cgccctgctc gcacccaagg tcccctcat cccctcatct   2400
ggcgaggaac agccactgga cctgagcatc ggcagcaggg ccagggcaag ccagaacgga   2460
ggtggccgtg agccgcggaa gaaccacgtc tacggtgaac ggaagccggg ggtcagcgag   2520
gggctgccta aggtgtgccc agcacagctg ccccagcagc cctccttgca ttatgctaag   2580
ccttcaccgt tcttcatgga tcccatctac agggtagaaa agcggaaggt ggcagaccct   2640
gtgggagtcc tgaaagagaa gtacctgcgg ccgtccccac ttctgttcca cccccagatg   2700
tcagccatag aaaccatgac ggagaagctg agagctttg cagccatgaa ggccgactca   2760
ggcagctccc tgcagcccct gcctcaccac ccgttcaact tccgctcccc accccaacg   2820
ctctcggatc ccatcctcag gaaggggaag gagagataca cgtgcaggta ctgtggcaag   2880
atcttcccca gatctgcaaa tctcacaaga catctgagga cacacacagg ggagcagcca   2940
tacaggtgca agtactgtga ccggtcattc agcatctcct ccaacctcca gcggcacgtg   3000
aggaacatcc acaacaaaga gaagccgttc aagtgccatc tgtgcaaccg ctgcttcggg   3060
cagcagacca acctagaccg gcacctgaag aagcacgaac acgagggcgc accagtgagc   3120
cagcactccg gggtgctcac gaaccacctg gcaccagcg cctcctcccc cacctccgag   3180
tcggacaacc atgcactttt agatgagaag gaagattctt acttctccga gatccgaaac   3240
ttcatcgcca acagcgagat gaaccaggca tccactcgaa tggacaaacg gcctgagatc   3300
caagacctgg acagcaaccc accgtgtcca ggctcagcca gtgcaaagcc agaggacgta   3360
gaggaggagg aagaggagga gctggaggaa gaggatgatg acagcttagc cgggaagtca   3420
caggaggaca cggtgtcccc cacacctgag ccccaaggag tctatgaaga tgaagaggat   3480
gaggaaccac ccagcctgac catgggcttt gaccataccc ggaggtgtgt tgaggagcga   3540
ggaggcggcc tgttagcttt ggagccgacg ccgacccttg gaagggget ggatctccgc   3600
agagcagctg aggaagcatt tgaagttaaa gatgtgctta attccacctt agattctgag   3660
gttttaaaac aaaccctgta caggcaggct aagaaccagg catatgcaat gatgctgtcc   3720
ctctctgaag acactcctct ccacgccccc tcccagagct cactggatgc ttggttgaac   3780
atcacaggac cctcgtcaga gtccggagcc tttaaccca tcaaccacct ctgaggtcct   3840
ggaggcccca gggccagagt ccaaagccag ggtaccagct gcaggagatg gagaaggggc   3900
cagggagcag ccccccaccc tcaacacctc cactttgcaa agtccagctt ctccattgaa   3960
actcagaacc cgaaggtccc tcgagtagcc gctggccttc atcacctctc tgaactggcc   4020
tcaaggacac gatctgcagt gggtgcggtg cacgggccac ccaggagctg ctcacaggag   4080
ccgtggatca gaaaactcgt gggcaagggt ggggtctcta tcccagcagg agccagttgg   4140
ccacatccag gcaactgcat ggtatgaaag aggaaatcag aaagacgtgg gcaagtgcta   4200
tggagagaga cctcatcaat gattttata atgagaatca catgattaag cctttggta    4260
atcttattga ctatagagtc tatttaagca tgtgggtttt aaaaaaaata gacggtattt   4320
tttaaaaatc                                                          4330
```

<210> SEQ ID NO 6
<211> LENGTH: 1275
<212> TYPE: PRT

<213> ORGANISM: Mus sp.

<400> SEQUENCE: 6

```
Met Arg Ser Lys Ala Arg Ala Lys Lys Leu Ala Lys Ser Asp Gly Asp
 1               5                  10                  15
Val Val Asn Asn Met Tyr Glu Pro Asp Pro Asp Leu Leu Ala Gly Gln
             20                  25                  30
Ser Ala Glu Glu Glu Thr Glu Asp Gly Ile Leu Ser Pro Ile Pro Met
         35                  40                  45
Gly Pro Pro Ser Pro Phe Pro Thr Ser Glu Asp Phe Thr Pro Lys Glu
     50                  55                  60
Gly Ser Pro Tyr Glu Ala Pro Val Tyr Ile Pro Glu Asp Ile Pro Ile
 65                  70                  75                  80
Pro Pro Asp Phe Glu Leu Arg Glu Ser Ile Pro Gly Ala Gly Leu
             85                  90                  95
Gly Ile Trp Ala Lys Arg Lys Met Glu Ile Gly Glu Arg Phe Gly Pro
            100                 105                 110
Tyr Val Val Thr Pro Arg Ala Ala Leu Lys Glu Ala Asp Phe Gly Trp
            115                 120                 125
Glu Met Leu Thr Asp Thr Glu Val Ser Ser Gln Glu Ser Cys Ile Lys
        130                 135                 140
Lys Gln Ile Ser Glu Asp Leu Gly Ser Glu Lys Phe Cys Val Asp Ala
145                 150                 155                 160
Asn Gln Ala Gly Ser Gly Ser Trp Leu Lys Tyr Ile Arg Val Ala Cys
            165                 170                 175
Ser Cys Asp Asp Gln Asn Leu Ala Met Cys Gln Ile Asn Glu Gln Ile
            180                 185                 190
Tyr Tyr Lys Val Ile Lys Asp Ile Glu Pro Gly Glu Glu Leu Leu Val
            195                 200                 205
His Val Lys Glu Gly Ala Tyr Ser Leu Gly Val Met Ala Pro Ser Leu
        210                 215                 220
Asp Glu Asp Pro Thr Phe Arg Cys Asp Glu Cys Asp Glu Leu Phe Gln
225                 230                 235                 240
Cys Arg Leu Asp Leu Arg Arg His Lys Lys Tyr Ala Cys Ser Ser Ala
            245                 250                 255
Gly Ala Gln Leu Tyr Glu Gly Leu Gly Glu Glu Leu Lys Pro Glu Gly
            260                 265                 270
Leu Gly Val Gly Ser Asp Gly Gln Ala His Glu Cys Lys Asp Cys Glu
            275                 280                 285
Arg Met Phe Pro Asn Lys Tyr Ser Leu Glu Gln His Met Ile Val His
        290                 295                 300
Thr Glu Glu Arg Glu Tyr Lys Cys Asp Gln Cys Pro Lys Ala Phe Asn
305                 310                 315                 320
Trp Lys Ser Asn Leu Ile Arg His Gln Met Ser His Asp Ser Gly Lys
            325                 330                 335
Arg Phe Glu Cys Glu Asn Cys Val Lys Val Phe Thr Asp Pro Ser Asn
            340                 345                 350
Leu Gln Arg His Ile Arg Ser Gln His Val Gly Ala Arg Ala His Ala
        355                 360                 365
Cys Pro Asp Cys Gly Lys Thr Phe Ala Thr Ser Ser Gly Leu Lys Gln
    370                 375                 380
His Lys His Ile His Ser Thr Val Lys Pro Phe Ile Cys Glu Val Cys
385                 390                 395                 400
```

His Lys Ser Tyr Thr Gln Phe Ser Asn Leu Cys Arg His Lys Arg Met
            405                 410                 415
His Ala Asp Cys Arg Thr Gln Ile Lys Cys Lys Asp Cys Gly Gln Met
            420                 425                 430
Phe Ser Thr Thr Ser Ser Leu Asn Lys His Arg Arg Phe Cys Glu Gly
            435                 440                 445
Lys Asn His Tyr Thr Pro Gly Ser Ile Phe Thr Pro Gly Leu Pro Leu
450                 455                 460
Thr Pro Ser Pro Met Met Asp Lys Thr Lys Pro Ser Pro Thr Leu Asn
465                 470                 475                 480
His Gly Gly Leu Gly Phe Ser Glu Tyr Phe Pro Ser Arg Pro His Pro
            485                 490                 495
Gly Ser Leu Pro Phe Ser Ala Ala Pro Pro Ala Phe Pro Thr Leu Thr
            500                 505                 510
Pro Gly Phe Pro Gly Ile Phe Pro Pro Ser Leu Tyr Pro Arg Pro Pro
            515                 520                 525
Leu Leu Pro Pro Thr Pro Leu Leu Lys Ser Pro Leu Asn His Ala Gln
            530                 535                 540
Asp Ala Lys Leu Pro Ser Pro Leu Gly Asn Pro Ala Leu Pro Leu Val
545                 550                 555                 560
Ser Ala Val Ser Asn Ser Ser Gln Gly Ala Thr Ala Ala Thr Gly Ser
            565                 570                 575
Glu Glu Lys Phe Asp Gly Arg Leu Glu Asp Ala Tyr Ala Glu Lys Val
            580                 585                 590
Lys Asn Arg Ser Pro Asp Met Ser Asp Gly Ser Asp Phe Glu Asp Ile
            595                 600                 605
Asn Thr Thr Thr Gly Thr Asp Leu Asp Thr Thr Thr Gly Thr Gly Ser
            610                 615                 620
Asp Leu Asp Ser Asp Leu Asp Ser Asp Arg Asp Lys Gly Lys Asp Lys
625                 630                 635                 640
Gly Lys Pro Val Glu Ser Lys Pro Glu Phe Gly Gly Ala Ser Val Pro
            645                 650                 655
Pro Gly Ala Met Asn Ser Val Ala Glu Val Pro Ala Phe Tyr Ser Gln
            660                 665                 670
His Ser Phe Phe Pro Pro Glu Glu Gln Leu Leu Thr Ala Ser Gly
            675                 680                 685
Ala Ala Gly Asp Ser Ile Lys Ala Ile Ala Ser Ile Ala Glu Lys Tyr
            690                 695                 700
Phe Asp Pro Gly Phe Met Ser Met Gln Glu Lys Lys Leu Gly Ser Leu
705                 710                 715                 720
Pro Tyr His Ser Val Phe Pro Phe Gln Phe Leu Leu Asn Phe Pro His
            725                 730                 735
Ser Leu Tyr Pro Phe Thr Asp Arg Ala Leu Ala His Asn Leu Leu Val
            740                 745                 750
Lys Ala Glu Pro Lys Ser Pro Gln Asp Ala Leu Lys Val Gly Gly Pro
            755                 760                 765
Ser Ala Glu Cys Pro Phe Asp Leu Thr Thr Lys Pro Lys Glu Ala Lys
            770                 775                 780
Pro Ala Leu Leu Ala Pro Lys Val Pro Leu Ile Pro Ser Ser Gly Glu
785                 790                 795                 800
Glu Gln Pro Leu Asp Leu Ser Ile Gly Ser Arg Ala Arg Ala Ser Gln
            805                 810                 815
Asn Gly Gly Gly Arg Glu Pro Arg Lys Asn His Val Tyr Gly Glu Arg

-continued

```
            820                 825                 830
Lys Pro Gly Val Ser Glu Gly Leu Pro Lys Val Cys Pro Ala Gln Leu
        835                 840                 845
Pro Gln Gln Pro Ser Leu His Tyr Ala Lys Pro Ser Pro Phe Phe Met
    850                 855                 860
Asp Pro Ile Tyr Arg Val Glu Lys Arg Lys Val Ala Asp Pro Val Gly
865                 870                 875                 880
Val Leu Lys Glu Lys Tyr Leu Arg Pro Ser Pro Leu Leu Phe His Pro
                885                 890                 895
Gln Met Ser Ala Ile Glu Thr Met Thr Glu Lys Leu Glu Ser Phe Ala
            900                 905                 910
Ala Met Lys Ala Asp Ser Gly Ser Ser Leu Gln Pro Leu Pro His His
        915                 920                 925
Pro Phe Asn Phe Arg Ser Pro Pro Thr Leu Ser Asp Pro Ile Leu
    930                 935                 940
Arg Lys Gly Lys Glu Arg Tyr Thr Cys Arg Tyr Cys Gly Lys Ile Phe
945                 950                 955                 960
Pro Arg Ser Ala Asn Leu Thr Arg His Leu Arg Thr His Thr Gly Glu
                965                 970                 975
Gln Pro Tyr Arg Cys Lys Tyr Cys Asp Arg Ser Phe Ser Ile Ser Ser
            980                 985                 990
Asn Leu Gln Arg His Val Arg Asn Ile His Asn Lys Glu Lys Pro Phe
        995                 1000                1005
Lys Cys His Leu Cys Asn Arg Cys Phe Gly Gln Gln Thr Asn Leu Asp
    1010                1015                1020
Arg His Leu Lys Lys His Glu His Glu Gly Ala Pro Val Ser Gln His
1025                1030                1035                1040
Ser Gly Val Leu Thr Asn His Leu Gly Thr Ser Ala Ser Ser Pro Thr
                1045                1050                1055
Ser Glu Ser Asp Asn His Ala Leu Leu Asp Glu Lys Glu Asp Ser Tyr
            1060                1065                1070
Phe Ser Glu Ile Arg Asn Phe Ile Ala Asn Ser Glu Met Asn Gln Ala
        1075                1080                1085
Ser Thr Arg Met Asp Lys Arg Pro Glu Ile Gln Asp Leu Asp Ser Asn
    1090                1095                1100
Pro Pro Cys Pro Gly Ser Ala Ser Ala Lys Pro Glu Asp Val Glu Glu
1105                1110                1115                1120
Glu Glu Glu Glu Glu Leu Glu Glu Asp Asp Asp Ser Leu Ala Gly
                1125                1130                1135
Lys Ser Gln Glu Asp Thr Val Ser Pro Thr Pro Glu Pro Gln Gly Val
            1140                1145                1150
Tyr Glu Asp Glu Glu Asp Glu Glu Pro Pro Ser Leu Thr Met Gly Phe
        1155                1160                1165
Asp His Thr Arg Arg Cys Val Glu Glu Arg Gly Gly Gly Leu Leu Ala
    1170                1175                1180
Leu Glu Pro Thr Pro Thr Phe Gly Lys Gly Leu Asp Leu Arg Arg Ala
1185                1190                1195                1200
Ala Glu Glu Ala Phe Glu Val Lys Asp Val Leu Asn Ser Thr Leu Asp
                1205                1210                1215
Ser Glu Val Leu Lys Gln Thr Leu Tyr Arg Gln Ala Lys Asn Gln Ala
            1220                1225                1230
Tyr Ala Met Met Leu Ser Leu Ser Glu Asp Thr Pro Leu His Ala Pro
        1235                1240                1245
```

Ser Gln Ser Ser Leu Asp Ala Trp Leu Asn Ile Thr Gly Pro Ser Ser
    1250                1255                1260

Glu Ser Gly Ala Phe Asn Pro Ile Asn His Leu
1265                1270                1275

<210> SEQ ID NO 7
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gaagagcgug aguacaaa                                                    18

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
caacgaacag auuuacuau                                                   19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gaagagcgug aguacaaau                                                   19

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gatccgacaa gataagataa ggatctataa gaagatgagg tatg                       44

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcctccactc acattggttt                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
tcctccaggg tagtggtgtc                                          20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcactggcaa gttctactgc aa                                       22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttggccaca cactccaata                                          20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acaccgagat ttccttcaaa ctg                                      23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtggcataag agaagcagca gtc                                      23

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgctcttctg tatcgcccag t                                        21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 18
accaagcgaa tgctggacat                                                    20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctgcatctg tgaagaggac aac                                                23

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagcgtcatg gtcagtctgt                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaaccatgaa gccaacgact                                                    20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcaggattct tctgagcgtt ct                                                 22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcgttgtcct tcaggcttag                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 24
cgaggattct ctggaactgc                                              20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcaagcataa gactggacca aa                                           22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cagtgtggtg cacgtctcca atc                                          23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tccgcgttct catgtaggtc t                                            21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgctgcatcc agttgaagac                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttctgcacag cttccacatc                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
```
gtcccaacca gaccatcaac                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtgatccaca cgaaccagtg                                               20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtgactggaa cactggtcct a                                             21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccgcgaagaa agcagttctg                                               20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agactccggt tttggtggaa c                                             21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acacgagctg ctacattaag ga                                            22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tggctcacac tgatctctgg                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
actaggaccc cgtcgaatct                                              20

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccctgccatt gttaagacc                                               19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcgtacggca atggctttat                                              20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtgccagttt cgatccgtag a                                            21

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cagcacggtg aagccattc                                               19

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tggccttcat cacctctctg aa                                           22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
taccgccttg tcaagaaacc                                              20

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctgtccagtc tatccttgca cac                                          23

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tccactctgg atctcccaag a                                            21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtccagcgtc tccatcactt                                              20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggctgaaggc aaagtcagtg t                                            21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gaagctgcgg tacaattcca g                                            21

```
<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
actgccacac ctccagtcat t                                              21

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctgttgtggg agacacgatg                                                20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
attgaagaaa gctgggctga                                                20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
accagatcct ggtggtgaag                                                20

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtaggtgaag agaacggcct tgt                                            23

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gggctgacaa gattcatggt                                                20
```

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
ccatctaggg ttatgatgct cttca                                          25

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
tatccttgtg gctgtccttg g                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
gccgtgttaa ggaatctgct g                                              21

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
ggcggagaag ccctgaa                                                   17

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
cagcttgtaa tgggttccac agt                                            23

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
agaaaaccgt gtggcagaga                                                20

<210> SEQ ID NO 61

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcgaagttca cagtggttcc                                              20

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gtcagcagcc tcctagatca tgt                                          23

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tccccacatc tgttctcaca                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggtcgcttct tcaaggtctg                                              20

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttgttggcat ctgtgtaaga gaatc                                        25

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tgaaccaaag ttgaccacca g                                            21

<210> SEQ ID NO 67
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggacctgatg caaccctatg a                                               21

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tgccatgttc atcaccttgt                                                 20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggaagaattc gtcaccctca                                                 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctccatcttg ctctggaagc                                                 20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tcccgctttt tcttgtccta                                                 20

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccagccagtt gcattgtag                                                  19

<210> SEQ ID NO 73
<211> LENGTH: 22
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 73
caaaaaacgt gtcgagctgg ta         22

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cacagagggc aaagatggaa c          21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cccagtcagt cgagtggatg            20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gccagagcct ttactgcatc            20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
accatgctct acgtgctgtg            20

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgctgctgtt cctgttttc             19

<210> SEQ ID NO 79
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 79
gaacggcttc ctcaggttct t                                           21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggccagcatc gtgtagatga                                             20

<210> SEQ ID NO 81
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcgtgcatcc gcttgtg                                                17

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tttctgatcc acggctcctg tga                                         23

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
agtggagcgc cagaatagaa                                             20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cagaaggcac agcagtcttg a                                           21

<210> SEQ ID NO 85
<211> LENGTH: 23
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 85
tccctccact gtaacgaaga ctc                                              23

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggtgacaagc acaagctgaa                                                  20

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tggaatctgt cctgctgtcc t                                                21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ccccttgtac ccttcaccaa t                                                21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ctttgcctca ctcaggattg g                                                21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cctcttctca gggctcacag                                                  20
```

MOLECULAR CONTROL OF BROWN FAT DIFFERENTIATION AND ENERGY EXPENDITURE

RELATED APPLICATIONS

This application claims the benefit of priority to U.S. Provisional Application No. 60/852,564 filed 18 Oct. 2006, which application is incorporated herein in its entirety by this reference.

GOVERNMENT SUPPORT

Work herein was supported under Grant No. 5R37DK031405-25, awarded by the National Institutes of Health. The U.S. governments therefore may have certain rights in this invention.

BACKGROUND OF THE INVENTION

Obesity represents the most prevalent of body weight disorders, affecting an estimated 30 to 50% of the middle-aged population in the western world. Obesity, defined as a body mass index (BMI) of 30 kg/$^2$m or more, contributes to diseases such as coronary artery disease, hypertension, stroke, diabetes, hyperlipidemia and some cancers. (See, e.g., Nishina, P. M. et al. (1994), *Metab.* 43:554-558; Grundy, S. M. & Barnett, J. P. (1990), Dis. Mon. 36:641-731). Obesity is a complex multifactorial chronic disease that develops from an interaction of genotype and the environment and involves social, behavioral, cultural, physiological, metabolic and genetic factors.

Generally, obesity results when energy intake exceeds energy expenditure, resulting in the growth and/or formation of adipose tissue via hypertrophic and hyperplastic growth. Hypertrophic growth is an increase in size of adipocytes stimulated by lipid accumulation. Hyperplastic growth is defined as an increase in the number of adipocytes in adipose tissue. It is thought to occur primarily by mitosis of pre-existing adipocytes caused when adipocytes fill with lipid and reach a critical size. An increase in the number of adipocytes has far-reaching consequences for the treatment and prevention of obesity.

Adipose tissue consists primarily of adipocytes. Vertebrates possess two distinct types of adipose tissue: white adipose tissue (WAT) and brown adipose tissue (BAT). WAT stores and releases fat according to the nutritional needs of the animal. This stored fat is used by the body for (1) heat insulation (e.g., subcutaneous fat), (2) mechanical cushion (e.g., surrounding internal organs), and (3) as a source of energy. BAT burns fat, releasing the energy as heat through thermogenesis. BAT thermogenesis is used both (1) to maintain homeothermy by increasing thermogenesis in response to lower temperatures and (2) to maintain energy balance by increasing energy expenditure in response to increases in caloric intake (Sears, I. B. et al. (1996) *Mol. Cell. Biol.* 16(7): 3410-3419). BAT is also the major site of thermogenesis in rodents and plays an important role in thermogenesis in human infants. In humans, and to a lesser extent rodents, brown fat diminishes with age, but can be re-activated under certain conditions, such as prolonged exposure to cold, maintenance on a high fat diet and in the presence of noradrenaline producing tumors.

Fat metabolism is regulated by two pathways, lipogenesis and lipolysis. Lipogenesis is the deposition of fat which occurs in the liver and in adipose tissue at cytoplasmic and mitochondrial sites. This process allows the storage of energy that is ingested which is not needed for current energy demands. Lipolysis is the chemical decomposition and release of fat from adipose and/or other tissues. This process predominates over lipogenesis when additional energy is required by the body.

Any treatment for obesity has to reduce energy intake, increase energy expenditure or combine both effects. Current therapies for obesity predominantly lead to decreased energy intake by acting at satiety centers in the brain or by reducing the efficiency of intestinal absorption. To date, no safe and reliable molecular mechanism for treating and/or preventing obesity by increasing energy expenditure or metabolic activity has been identified. Given the severity and prevalence of obesity related disorders, there exists a great need for the identification of an anti-obesity therapeutic.

SUMMARY OF THE INVENTION

The present invention is based on the discovery that Prdm16 can induce brown fat differentiation in mammals. Increased brown fat differentiation in mammals induces the expression of mitochondrial genes and cellular respiration. Densely packed mitochondria are a characteristic of brown fat cells. Increased respiration (both total and uncoupled respiration) results in increased heat dissipation and increased energy expenditure by the mammal. The increases in heat dissipation and increased energy expenditure stimulate the metabolic rate of the mammal. Through the stimulation of the metabolic rate, Prdm16 may be used to treat and/or prevent obesity or an obesity related disorder.

Accordingly, the present invention provides methods for preventing or treating obesity or an obesity related disorder in a subject (e.g., a human) comprising inducing Prdm16 expression sufficient to activate brown fat cell differentiation, wherein the differentiated brown fat cells increase energy expenditure to thereby prevent or treat obesity or an obesity related disorder in the subject. The obesity related disorder may be insulin resistant obesity, type II diabetes, hyperphagia, endocrine abnormalities, triglyceride storage disease, Bardet-Biedl syndrome, Lawrence-Moon syndrome, Prader-Labhart-Willi syndrome, anorexia, and cachexia.

In another aspect, the invention provides a method for treating a subject (e.g., human) suffering from obesity or an obesity-related disorder comprising administering to the subject an agent capable of inducing Prdm16 expression or activity, wherein Prdm16 expression increases respiration and energy expenditure to thereby treat obesity or an obesity related disorder in the subject. In one embodiment, the increase in respiration is in total cellular respiration. In another embodiment, the increase in respiration is in uncoupled respiration. Uncoupled respiration may be measured by oxygen consumption. Further, energy expenditure by cells expressing Prdm16 increases or stimulates the metabolic rate of the subject.

In another aspect, the of the invention provides a method for increasing energy expenditure in a mammal (e.g., a human) comprising inducing Prdm16 expression sufficient to activate brown fat cell differentiation in the mammal, wherein the differentiated brown fat cells promote energy expenditure thereby increasing energy expenditure in the mammal.

In a further aspect, the invention provides for a method for identifying a compound capable of modulating Prdm16 expression or activity comprising contacting a cells (e.g., an adipose cell) with a test compound and determining whether Prdm16 expression or activity is modulated. It will be appreciated that Prdm16 expression or activity may be determined by methods known to those skilled in the art. For example, Prdm16 expression may be measured based on Prdm16 polypeptide expression and is detected by an anti-Prdm16 antibody. In an alternate embodiment, Prdm16 expression is measured based on Prdm16 mRNA expression and may be detected by Northern blotting. In addition, the expression or activity of mitochondrial genes (e.g., cytochrome c, cox4i1, cox III, cox 5b, atpase b2, cox II, atp5o and/or ndufb5) may be determined. In another embodiment, Prdm16 expression may be measured by monitoring cellular respiration as measured by oxygen consumption.

In further embodiment, the compound capable of modulating Prdm16 expression or activity may be a peptide, a peptidomimetic, a small molecule, an antisense nucleic acids. Compounds that increase or stimulate Prdm16 expression and/or activity may be used to treat or prevent obesity or an obesity related disorder.

Another aspect of the invention provides a method for inducing brown fat cell differentiation in a mammal comprising expressing Prdm16 in preadipocyte cells; injecting the preadipocyte cells expressing Prdm16 into the mammal; and monitoring the differentiation of brown fat cells in the mammal. Preadipocyte cells expressing Prdm16 may be injected into the mammal, e.g., by a subcutaneous or an intravenous injection.

In one embodiment, the differentiation of brown fat cells in the mammal may be monitored by measuring the expression of a classic marker for brown adipose tissue including cidea, type II deiodinase, cig30, pgc1α, ucp1, and Prdm16. In another embodiment, the differentiation of brown fat cells may be monitored by measuring the expression of a mitochondrial gene including, cytochrome C, cox4i1, coxIII, cox5b, atpase b2, cox II, atp5o, and/or ndufb5. In yet another embodiment, the differentiation of brown fat cells may be monitored by measuring the expression of a marker listed in Table 1. In an alternate embodiment, the differentiation of brown fat cells may be monitored by measuring respiration within the cell expressing Prdm16. Respiration may be total or uncoupled respiration and may be measured by oxygen consumption.

In a further aspect, the invention provides a method of reducing brown fat cells comprising contacting cells expressing Prdm16 with the antisense nucleic acid sequence. The antisense nucleic acid may be the nucleic acid sequence set forth in SEQ ID NO: 7.

Other features and advantages of the invention will be apparent from the following detailed description and claims.

BRIEF DESCRIPTION OF FIGURES

FIG. 1 shows the (A) nucleic acid and (B) amino acid sequence for human Prdm16 transcript variant 1.

FIG. 2 shows the (A) nucleic acid and (B) amino acid sequence for human Prdm16 transcript variant 2.

FIG. 3 shows the (A) nucleic acid and (B) amino acid sequence for murine Prdm16.

FIG. 4 is a series of graph showing that Prdm16 is enriched in BAT tissue and cell lines. (A) is a graph that shows relative mRNA expression of Prdm16 in WAT tissue and BAT tissue. (B) is a graph that shows Prdm16 mRNA expression is increased in two BAT tissues (BAT1 and BAT2). (C) is a graph showing Prdm16 expression in BAT tissue at zero, four and eight days of differentiation. (D) is a graph showing Prdm16 expression in various tissues.

FIG. 5 is a series of graphs showing that Prdm16 induces brown fat-specific genes. (A) is a graph showing expression of Prdm16 in the presence and absence of cAMP. (B and D) are graphs showing that Prdm16 induces expression of brown fat specific genes including cidea, type II deiodinase (deiodinase-D2), cig30, pgc1α, and ucp1 in the presence and absence of cAMP. (C) Adiponectin and PPARγ expression are not affected by Prdm16 expression. "Puro" refers to the empty vector control.

FIG. 10 is (A) western blot and (B) a graph showing selective reduction of brown fat-specific mRNAs in Prdm16-depleted brown fat cells.

FIG. 24G shows Western blot analysis of UCP1 protein levels in primary brown fat cells expressing sh-PRDM16 or sh-SCR control with and without cAMP treatment. (H) shows mRNA levels of various mitochondrial components in adipocytes from sh-PRDM16 and sh-SCR expressing primary brown preadipocytes. (n=3-5, mean±SD)(* $p<0.05$; ** $p<0.01$).

DETAILED DESCRIPTION OF THE INVENTION

Figure 6:
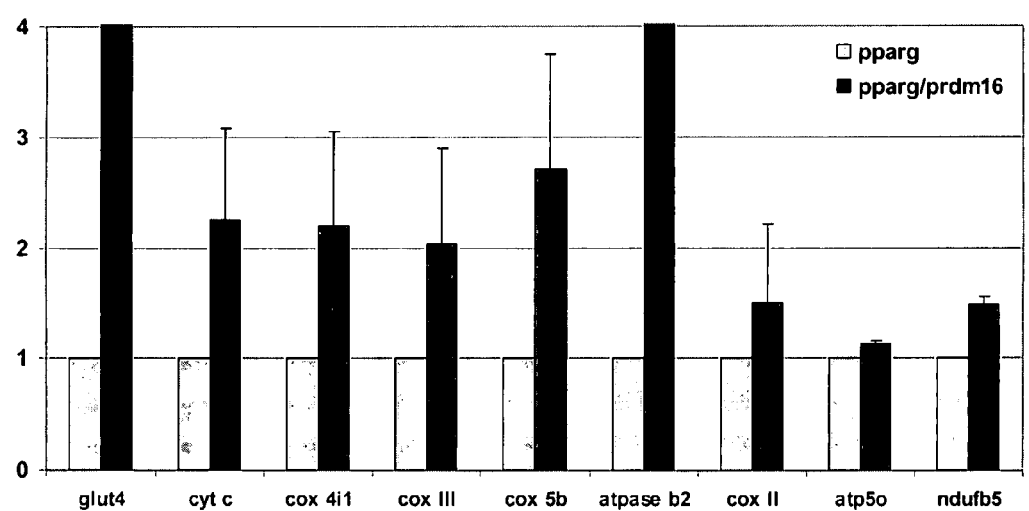
FIG. 6 is a graph showing induction of mitochondrial genes by Prdm16 in the presence of PPARγ. Mitochondrial genes: Cytochrome C (cytc), cytochrome C oxidase subunit IV isoform 1 (cox4 μl), cytochrome C oxidase, subunit III (cox III), cytochrome C oxidase subunit Vb (cox 5b), atpase b2, cox II, atp5o and NADH dehydrogenase (ubiquinone) 1 beta subcomplex, 5 (ndufb5).

The present invention is based on the discovery that Prdm16 can induce brown fat cell differentiation. These results indicate a regulatory role of Prdm16 in brown fat differentiation and thermogenesis. The discovery further suggests that Prdm16 can direct the activation of a distinct set of target genes (e.g., cidea, type II deiodinase, cig30, pgc1α and ucp1) that are markers of brown fat. In particular, expression of Prdm16 induces the expression of mitochondrial genes (e.g., cytochrome c, cox 4i1, cox III, cox 5b, atpase b2, cox II, atp5o and ndufb5) and respiration (i.e., total and uncoupled respiration). Prdm16 expression increases the fraction of respiration that is uncoupled. Increased brown fat in mammals and increased uncoupled respiration results in increased heat dissipation and thereby increases energy expenditure by the mammal. Thus, by increasing the metabolic rate of the mammal through increased energy expenditure, Prdm16 can be used to treat obesity and obesity-related disorders.

It has been further discovered Prdm16 expression can be reduced a short hairpin RNA of the nucleotide sequence set forth in SEQ ID NO: 7. Reduction of Prdm16 expression results in decreased expression of the set of target genes (e.g., cig30, cidea, pgc1α, and ucp1) that are markers of brown fat cells.

In order that the present invention may be more readily understood, certain terms are first defined. Additional definitions are set forth throughout the detailed description.

The terms "metabolic disorder" and "obesity related disorders" are used interchangeably herein and include a disorder, disease or condition which is caused or characterized by an abnormal metabolism (i.e., the chemical changes in living cells by which energy is provided for vital processes and activities) in a subject. Metabolic disorders include diseases, disorders, or conditions associated with aberrant thermogenesis or aberrant adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response). Examples of metabolic disorders include obesity, including insulin resistant obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia.

As used herein, "obesity" refers to a body mass index (BMI) of 30 kg/$^2$m or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/$^2$m or more, 26 kg/$^2$m or more, 27 kg/$^2$m or more, 28 kg/$^2$m or more, 29 kg/$^2$m or more, 29.5 kg/$^2$m or more, or 29.9 kg/$^2$m or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

"Treatment" refers to reducing the BMI of the mammal to less than about 25.9, and maintaining that weight for a period of time, e.g., for at least about 6 months. The treatment suitably results in an increase in metabolic activity.

"Prevention" refers to preventing obesity or an obesity related disorder from occurring if the treatment is administered prior to the onset of the obese condition. Moreover, if treatment is commenced in subjects already suffering from or having symptoms of obesity or an obesity related disorder, such treatment is expected to prevent, or to prevent the progression of obesity or the obesity related disorder, and the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

As used herein, the term "Prdm16" refers to a PR-domain containing protein-16 and is intended to include fragments, variants (e.g., allelic variants) and derivatives thereof. Two spliced variants encoding distinct isoforms of Prdm16 have been previously described (Nishikata, et al. (2003) Blood 102(9):3323-32; Mochizuki, N. et al., (2000) Blood 96(9): 3209-14). The nucleic acid sequence of human Prdm16 corresponding to spliced transcript variant 1 (Genbank Accession number NM_022114) is provided herein as SEQ ID NOs: 1 (see FIG. 1). The nucleic acid sequence of human Prdm16 corresponding to spliced transcript variant 2 (Genbank Accession number NM_199454) is provided herein as SEQ ID NOs: 3 (see FIG. 2). Variant 1 encodes a longer isoform of Prdm16. Variant 2 uses an alternative splice site for the 3' exon compared to variant 1, and thus, lacks an internal region compared to variant 1. The amino acid sequences of human Prdm16 corresponding to spliced transcript variants 1 and 2 are provided herein as SEQ ID NOs: 2 and 4, respectively (Genbank Accession numbers NP_071397 and NP_955533, respectively).

The nucleotide and amino acid sequences of mouse Prdm16, which correspond to Genbank Accession number NM_027504 and NP_081780 respectively, are set forth in SEQ ID NO: 5 and 6 (see FIG. 3).

As used herein, the term "PGC-1" refers to a PPARγ Coactivator 1 protein and is intended to include any of its' derivatives, including PGC-1α and PGC-1β. PGC-1 has been described previously (Puigserver, P. et al. (1998) *Cell* 92(6): 829-39; U.S. Pat. No. 6,166,192; and PCT International Publication Nos. WO 98/54220; the contents of all of which are incorporated herein by reference).

PGC-1 was initially identified as a PPARγ-interacting protein from a brown adipose tissue (BAT) library and was subsequently found to associate with an array of nuclear receptors (NRs) and transcription factors (Puigserver, P. et al. (1998) *Cell* 92:829-839; Wu, Z. et al. (1999) *Cell* 98:115-124; Vega, R. B. et al. (2000) *Mol. Cell. Biol.* 20:1868-1876; Michael, L. F. et al. (2001) *Proc. Natl. Acad. Sci. USA* 98:3820-3825). PGC-1 has been shown to coordinately regulate the program of mitochondrial biogenesis and adaptive thermogenesis in BAT and skeletal muscle, mainly through the coactivation of PPARs and nuclear respiratory factor 1 (NRF1), a nuclear transcription factor that regulates the expression of many mitochondrial genes (Puigserver et al. (1998) supra; Wu et al. (1999) supra). In transgenic mice, PGC-1 increases mitochondrial biogenesis and β-oxidation of fatty acids in the heart, likely through augmentation of PPARα and NRF1 transcriptional activity (Lehman, J. J. et al. (2000) *J. Clin. Invest.* 106:847-856). Recently, PGC-1 expression was found to be elevated in fasted liver and several models of type-1 and type-2 diabetes; in addition, PGC-1 can directly control the activation of hepatic gluconeogenesis (Yoon, J. C. et al. (2001) *Nature* 413:131-138; Herzig, S. et al. (2001) *Nature* 413:179-183). Prdm16 acts upstream of PGC-1.

I. Nucleic Acids of the Invention

One aspect of the invention pertains to methods utilizing isolated nucleic acid molecules that encode Prdm16 or biologically active portions thereof, as well as nucleic acid fragments sufficient for use as hybridization probes to identify prdm16-encoding nucleic acid (i.e., Prdm16 mRNA). As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Prdm16 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, i.e., a nucleic acid molecule having the nucleotide sequence of SEQ ID NOs: 1, 3, and 5 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in SEQ ID NOs: 1, 3, and 5 or a portion thereof (i.e., 400, 450, 500, or more nucleotides), can be isolated using standard molecular biology techniques and the sequence information provided herein. For example, a human prdm16 cDNA can be isolated from a human liver, heart, kidney, or brain cell line (from Stratagene, LaJolla, Calif., or Clontech, Palo Alto, Calif.) using all or portion of SEQ ID NOs: 1, 3, and 5 as a hybridization probe and standard hybridization techniques (i.e., as described in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989). Moreover, a nucleic acid molecule encompassing all or a portion of SEQ ID NOs: 1, 3, or 5 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs: 1, 3, or 5 can be isolated by the polymerase chain reaction using oligonucleotide primers designed based upon the sequence of SEQ ID NOs: 1, 3, or 5 or the homologous nucleotide sequence. For example, mRNA can be isolated from liver cells, heart cells, kidney cells, brain cells, or brown adipocytes (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NOs: 1, 3, or 5 or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a Prdm16 nucleotide sequence can be prepared by standard synthetic techniques, i.e., using an automated DNA synthesizer.

Probes based on the prdm16 nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a Prdm16 protein, such as by measuring a level of a Prdm16-encoding nucleic acid in a sample of cells from a subject, i.e., detecting Prdm16 mRNA levels.

Nucleic acid molecules encoding other prdm16 family members and thus which have a nucleotide sequence which differs from the Prdm16 sequences of SEQ ID NOs: 1, 3, or 5 are intended to be of the invention. Moreover, nucleic acid molecules encoding Prdm16 proteins from different species, and thus which have a nucleotide sequence which differs from the Prdm16 sequences of SEQ ID NOs:1, 3 or 5 are intended to be within the scope of the invention. For example, rat or monkey Prdm16 cDNA can be identified based on the nucleotide sequence of a human and/or mouse Prdm16.

In one embodiment, the nucleic acid molecule of the invention encodes a protein or portion thereof which includes an amino acid sequence which is sufficiently homologous to an amino acid sequence of SEQ ID NO: 2, 4, or 6 such that the protein or portion thereof maintains one or more of the following biological activities: 1) it can modulate the expression of cidea, type II deiodinase, cig30, PGC-1α and ucp1; 2) it can modulate the expression of mitochondrial genes including, cytochrome c, cox 4i1, cox III, cox 5b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO: 2, 4, or 6) amino acid residues to an amino acid sequence of SEQ ID NO: 2, 4, or 6 such that the protein or portion thereof maintains one or more of the following biological activities: 1) it can modulate the expression of cidea, type II deiodinase, cig30, PGC-1α and ucp1; 2) it can modulate the expression of mitochondrial genes including, cytochrome c, cox 4i1, cox III, cox 5b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

In another embodiment, the protein is at least about 50%, preferably at least about 60%, more preferably at least about 70%, yet more preferably at least about 80%, still more preferably at least about 90%, and most preferably at least about 95% or more homologous to the entire amino acid sequence of SEQ ID NO: 2, 4, or 6.

Portions of proteins encoded by the Prdm16 nucleic acid molecule of the invention are preferably biologically active portions of the Prdm16 protein. As used herein, the term "biologically active portion of Prdm16" is intended to include a portion, e.g., a domain/motif, of Prdm16 that has one or more of the following activities: 1) it can modulate the expression of cidea, type II deiodinase, cig30, PGC-1α and ucp1; 2) it can modulate the expression of mitochondrial genes including, cytochrome c, cox 4i1, cox III, cox 5b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

Standard binding assays, e.g., immunoprecipitations and yeast two-hybrid assays, as described herein, can be performed to determine the ability of a Prdm16 protein or a biologically active portion thereof to interact with a target of interest. To determine whether a Prdm16 family member of the present invention modulates cidea, type II deiodinase, cig30, PGC-1α and ucp1 expression, in vitro transcriptional assays can be performed. To perform such an assay, the full length promoter/enhancer region of the gene of interest (e.g., cidea, type II deiodinase, cig30, PGC-1α and ucp1) can be linked to a reporter gene such as chloramphenicol acetyl-transferase (CAT) or luciferase and introduced into host cells (e.g., liver cells such as Fao hepatoma cells, or COS cells). The same host cells can then be transfected a nucleic acid molecule encoding the Prdm16 molecule. In some embodiments, nucleic acid molecules encoding PPARγ can also be transfected. The effect of the Prdm16 molecule can be measured by testing CAT or luciferase activity and comparing it to CAT or luciferase activity in cells which do not contain nucleic acid encoding the Prdm16 molecule. An increase or decrease in CAT or luciferase activity indicates a modulation of expression of the gene of interest. In another embodiment, because cidea, type II deiodinase, cig30, pgc-1α, and ucp1 expression is known to be a critical component in the cascade of events leading to elevated thermogenesis, this assay can also measure the ability of the Prdm16 molecule to modulate thermogenesis in adipocytes.

The invention further encompasses nucleic acid molecules that differ from the nucleotide sequence shown in SEQ ID NO: 1, 3 or 5 (and portions thereof) due to degeneracy of the genetic code and thus encode the same Prdm16 protein as that encoded by the nucleotide sequence shown in SEQ ID NO: 1, 3, or 5. In another embodiment, an isolated nucleic acid molecule of the invention has a nucleotide sequence encoding a protein having an amino acid sequence shown in SEQ ID NO: 2, 4, or 6 or a protein having an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO: 2, 4, or 6.

In addition to the human and mouse Prdm16 nucleotide sequences shown in SEQ ID NO: 1 or 3 and SEQ ID NO: 4, respectively, it will be appreciated by those skilled in the art that DNA sequence polymorphisms that lead to changes in the amino acid sequences of Prdm16 may exist within a population (e.g., a mammalian population, e.g., a human population). Such genetic polymorphism in the Prdm16 gene may exist among individuals within a population due to natural allelic variation. As used herein, the terms "gene" and "recombinant gene" refer to nucleic acid molecules comprising an open reading frame encoding a Prdm16 protein, preferably a mammalian, e.g., human, Prdm16 protein. Such natural allelic variations can typically result in 1-5% variance in the nucleotide sequence of the Prdm16 gene. Any and all such nucleotide variations and resulting amino acid polymorphisms in Prdm16 that are the result of natural allelic variation and that do not alter the functional activity of Prdm16 are intended to be within the scope of the invention. Moreover, nucleic acid molecules encoding Prdm16 proteins from other species, and thus which have a nucleotide sequence which differs from the human or mouse sequences of SEQ ID NO: 1, 3, or 5, are intended to be within the scope of the invention. Nucleic acid molecules corresponding to natural allelic variants and homologues of the human or mouse Prdm16 cDNAs of the invention can be isolated based on their homology to the human or mouse Prdm16 nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the Prdm16 sequence that may exist in the population, the skilled artisan will further appreciate that changes can be introduced by mutation into the nucleotide sequence of SEQ ID NO: 1, 3, or 5 thereby leading to changes in the amino acid sequence of the encoded Prdm16 protein, without altering the functional ability of the Prdm16 protein. For example, nucleotide substitutions leading to amino acid substitutions at "non-essential" amino acid residues can be made in the sequence of SEQ ID NO: 1, 3, or 5. A "non-essential" amino acid residue is a residue that can be altered from the wild-type sequence of Prdm16 (e.g., the sequence of SEQ ID NO: 2, 4, or 6) without altering the activity of Prdm16, whereas an "essential" amino acid residue is required for Prdm16 activity. Other amino acid residues, however, (e.g., those that are not conserved or only semi-conserved between mouse and human) may not be essential for activity and thus are likely to be amenable to alteration without altering Prdm16 activity. Furthermore, amino acid residues that are essential for Prdm16 functions related to thermogenesis and/or adipogenesis, but not essential for Prdm16 functions related to gluconeogenesis, are likely to be amenable to alteration.

Accordingly, another aspect of the invention pertains to nucleic acid molecules encoding Prdm16 proteins that contain changes in amino acid residues that are not essential for Prdm16 activity. Such Prdm16 proteins differ in amino acid sequence from SEQ ID NO: 2, 4, or 6 yet retain at least one of the Prdm16 activities described herein. In one embodiment, the isolated nucleic acid molecule comprises a nucleotide sequence encoding a protein, wherein the protein comprises an amino acid sequence at least about 60% homologous to the amino acid sequence of SEQ ID NO: 2, 4, or 6 and is capable of inducing brown fat differentiation. Preferably, the protein encoded by the nucleic acid molecule is at least about 70% homologous, preferably at least about 80-85% homologous, still more preferably at least about 90%, and most preferably at least about 95% homologous to the amino acid sequence of SEQ ID NO: 2, 4, or 6.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (J. Mol. Biol. (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a Prdm16 protein homologous to the protein of SEQ ID NO: 2, 4, or 6 can be created by introducing one or more nucleotide substitutions, additions or deletions into the nucleotide sequence of SEQ ID NO: 1, 3, or 5 or a homologous nucleotide sequence such that one or more amino acid substitutions, additions or deletions are introduced into the encoded protein. Mutations can be introduced into SEQ ID NO: 1, 3, or 5 or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in Prdm16 is preferably replaced with another amino acid residue from the same side chain family. Alternatively, in another embodiment, mutations can be introduced randomly along all or part of a Prdm16 coding sequence, such as by saturation mutagenesis, and the resultant mutants can be screened for a Prdm16 activity described herein to identify mutants that retain Prdm16 activity. Following mutagenesis of SEQ ID NO: 1, 3 or 5, the encoded protein can be expressed recombinantly (as described herein) and the activity of the protein can be determined using, for example, assays described herein.

Prdm16 levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, Prdm16 levels are ascertained by measuring gene transcript (e.g. mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the Prdm16 mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding Prdm16. Other suitable probes for use in the diagnostic assays of the invention are described herein. Hybridization of an mRNA with the probe indicates that Prdm16 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the Prdm16 mRNA expression levels.

An alternative method for determining the Prdm16 mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the Prdm16 mRNA.

As an alternative to making determinations based on the absolute Prdm16 expression level, determinations may be based on the normalized Prdm16 expression level. Expression levels are normalized by correcting the absolute Prdm16 expression level by comparing its expression to the expression of a non-Prdm16 gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a Prdm16 protein can also be detected and/or quantified by detecting or quantifying the expressed polypeptide. The Prdm16 polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express Prdm16.

In addition to the nucleic acid molecules encoding Prdm16 proteins described above, another aspect of the invention pertains to isolated nucleic acid molecules which are antisense thereto. An "antisense" nucleic acid comprises a nucleotide sequence which is complementary to a "sense" nucleic acid encoding a protein, i.e., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Prdm16 coding strand, or to only a portion thereof. In one embodiment, an antisense nucleic acid molecule is antisense to a "coding region" of the coding strand of a nucleotide sequence encoding Prdm16. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding Prdm16. The term "noncoding region" refers to 5' and 3' sequences which flank the coding region that are not translated into amino acids (i.e., also referred to as 5' and 3' untranslated regions).

II. Recombinant Expression Vectors and Host Cells

Another aspect of the invention pertains to the use of vectors, preferably expression vectors, containing a nucleic acid encoding Prdm16 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Adenoviral vectors comprising a Prdm16 nucleic acid molecule are preferred.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., Prdm16 proteins, mutant forms of Prdm16, fusion proteins, etc.).

The recombinant expression vectors of the invention can be designed for expression of Prdm16 in prokaryotic or eukaryotic cells. For example, Prdm16 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the Prdm16 is cloned into a pGEX expression vector to create a vector encoding a fusion protein comprising, from the N-terminus to the C-terminus, GST-thrombin cleavage site-Prdm16. The fusion protein can be purified by affinity chromatography using glutathione-agarose resin. Recombinant Prdm16 unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the Prdm16 expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, Prdm16 can be expressed in insect cells using baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to Prdm16 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Prdm16 protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Prdm16 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Prdm16 protein. Accordingly, the invention further provides methods for producing Prdm16 protein using the host cells of the invention. In one embodiment, the method comprises culturing the host cell of invention (into which a recombinant expression vector encoding Prdm16 has been introduced) in a suitable medium until Prdm16 is produced. In another embodiment, the method further comprises isolating Prdm16 from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which Prdm16-coding sequences have been introduced. Such host cells can then be used to create non-human transgenic animals in which exogenous Prdm16 sequences have been introduced into their genome or homologous recombinant animals in which endogenous Prdm16 sequences have been altered. Such animals are useful for studying the function and/or activity of Prdm16 and for identifying and/or evaluating modulators of Prdm16 activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous Prdm16 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing Prdm16-encoding nucleic acid into the male pronuclei of a fertilized oocyte, e.g., by microinjection, retroviral infection, and allowing the oocyte to develop in a pseudopregnant female foster animal. The human Prdm16 cDNA sequence can be introduced as a transgene into the genome of a nonhuman animal. Alternatively, a nonhuman homologue of the human Prdm16 gene (SEQ ID NO: 1 or 3), such as a mouse Prdm16 gene (SEQ ID NO: 5), can be used as a transgene. Intronic sequences and polyadenylation signals can also be included in the transgene to increase the efficiency of expression of the transgene. A tissue-specific regulatory sequence(s) can be operably linked to the Prdm16 transgene to direct expression of Prdm16 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the Prdm16 transgene in its genome and/or expression of Prdm16 mRNA in tissues or cells of the animals. A transgenic founder animal can then be used to breed additional animals carrying the transgene. Moreover, transgenic animals carrying a transgene encoding Prdm16 can further be bred to other transgenic animals carrying other transgenes.

To create a homologous recombinant animal, a vector is prepared which contains at least a portion of a Prdm16 gene into which a deletion, addition or substitution has been introduced to thereby alter, e.g., functionally disrupt, the Prdm16 gene. The Prdm16 gene can be a human gene (e.g., from a human genomic clone isolated from a human genomic library screened with the cDNA of SEQ ID NO: 1 or 3), but more preferably, is a nonhuman homologue of a human Prdm16 gene. For example, a mouse Prdm16 gene can be used to construct a homologous recombination vector suitable for altering an endogenous Prdm16 gene in the mouse genome. In a preferred embodiment, the vector is designed such that, upon homologous recombination, the endogenous Prdm16 gene is functionally disrupted (i.e., no longer encodes a functional protein; also referred to as a "knock out" vector). Alternatively, the vector can be designed such that, upon homologous recombination, the endogenous Prdm16 gene is mutated or otherwise altered but still encodes functional protein (e.g., the upstream regulatory region can be altered to thereby alter the expression of the endogenous Prdm16 protein). In the homologous recombination vector, the altered portion of the Prdm16 gene is flanked at its 5' and 3' ends by additional nucleic acid of the Prdm16 gene to allow for homologous recombination to occur between the exogenous Prdm16 gene carried by the vector and an endogenous Prdm16 gene in an embryonic stem cell. The additional flanking Prdm16 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Prdm16 gene has homologously recombined with the endogenous Prdm16 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated Prdm16 Proteins and Anti-Prdm16 Antibodies

Another aspect of the invention pertains to the use of isolated Prdm16 proteins, and biologically active portions thereof, as well as peptide fragments suitable for use as immunogens to raise anti-Prdm16 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of Prdm16 protein in which the protein is separated from cellular components of the cells in which it is naturally or recombinantly produced. In one embodiment, the language "substantially free of cellular material" includes preparations of Prdm16 protein having less than about 30% (by dry weight) of non-Prdm16 protein (also referred to herein as a "contaminating protein"), more preferably less than about 20% of non-Prdm16 protein, still more preferably less than about 10% of non-Prdm16 protein, and most preferably less than about 5% non-Prdm16 protein. When the Prdm16 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of Prdm16 protein in which the protein is separated from chemical precursors or other chemicals which are involved in the synthesis of the protein. In one embodiment, the language "substantially free of chemical precursors or other chemicals" includes preparations of Prdm16 protein having less than about 30% (by dry weight) of chemical precursors or non-Prdm16 chemicals, more preferably less than about 20% chemical precursors or non-Prdm16 chemicals, still more preferably less than about 10% chemical precursors or non-Prdm16 chemicals, and most preferably less than about 5% chemical precursors or non-Prdm16 chemicals. In preferred embodiments, isolated proteins or biologically active portions thereof lack contaminating proteins from the same animal from which the Prdm16 protein is derived. Typically, such proteins are produced by recombinant expression of, for example, a human Prdm16 protein in a nonhuman cell.

An isolated Prdm16 protein or a portion thereof of the invention has one or more of the following biological activities: 1) it can modulate the expression of cidea, type II deiodinase, cig30, PGC-1α and ucp1; 2) it can modulate the expression of mitochondrial genes including, cytochrome c, cox 4I1, cox III, cox 5b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

In preferred embodiments, the protein or portion thereof comprises an amino acid sequence which is sufficiently homologous to an amino acid sequence of SEQ ID NO: 2, 4, or 6 such that the protein or portion thereof maintains one or more of the following biological activities: 1) it can modulate the expression of cidea, type II deiodinase, cig30, pgc-1α and ucp1; 2) it can modulate the expression of mitochondrial genes including, cytochrome c, cox 4i1, cox III, cox 5b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity. The portion of the protein is preferably a biologically active portion as described herein. In another preferred embodiment, the Prdm16 protein has an amino acid sequence shown in SEQ ID NO: 2, 4, or 6, respectively, or an amino acid sequence which is at least about 50%, preferably at least about 60%, more preferably at least about 70%, yet more preferably at least about 80%, still more preferably at least about 90%, and most preferably at least about 95% or more homologous to the amino acid sequence shown in SEQ ID NO: 2, 4, or 6. In yet another preferred embodiment, the Prdm16 protein has an amino acid sequence which is encoded by a nucleotide sequence which hybridizes, e.g., hybridizes under stringent conditions, to the nucleotide sequence of SEQ ID NO:1, 3 or 5 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO: 1, 3, or 5. The preferred Prdm16 proteins of the present invention also preferably possess at least one of the Prdm16 biological activities described herein. For example, a preferred Prdm16 protein of the present invention includes an amino acid sequence encoded by a nucleotide sequence which hybridizes, e.g., hybridizes under stringent conditions, to the nucleotide sequence of SEQ ID NO:1, 3 or 5 and which can maintain one or more of the following biological activities: 1) it can modulate the expression of cidea, type II deiodinase, cig30, PGC-1α and ucp1; 2) it can modulate the expression of mitochondrial genes including, cytochrome c, cox III, cox 5b, atpase b2, cox II, atp5o and ndufb5; 3) it can increase or stimulate total respiration of a cell; 4) it can increase or stimulate uncoupled respiration of a cell; 5) it can increase or stimulate heat dissipation; 6) it can modulate thermogenesis; 7) it can increase or stimulate energy expenditure; 8) it can treat diseases or disorders characterized by increased PGC-1 expression or activity, e.g., diabetes or obesity.

In other embodiments, the Prdm16 protein is substantially homologous to the amino acid sequence of SEQ ID NO: 2, 4 or 6 and retains the functional activity of the protein of SEQ ID NO: 2, 4 or 6 yet differs in amino acid sequence due to natural allelic variation or mutagenesis, as described in detail in subsection I above. Accordingly, in another embodiment, the Prdm16 protein is a protein which comprises an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO: 2, 4, or 6.

Biologically active portions of the Prdm16 protein include peptides comprising amino acid sequences derived from the amino acid sequence of the Prdm16 protein, e.g., the amino acid sequence shown in SEQ ID NO: 2, 4, or 6 or the amino acid sequence of a protein homologous to the Prdm16 protein, which include fewer amino acids than the full length Prdm16 protein or the full length protein which is homologous to the Prdm16 protein, and exhibit at least one activity of the Prdm16 protein. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., PR domain (PRD1-BF1-RIZ homology region). In a preferred embodiment, the biologically active portion of the protein which includes one or more the domains/motifs described herein can modulate differentiation of adipocytes and/or thermogenesis in brown adipocytes. Moreover, other biologically active portions, in which other regions of the protein are deleted, can be prepared by recombinant techniques and evaluated for one or more of the activities described herein. Preferably, the biologically active portions of the Prdm16 protein include one or more selected domains/motifs or portions thereof having biological activity.

Prdm16 proteins are preferably produced by recombinant DNA techniques. For example, a nucleic acid molecule encoding the protein is cloned into an expression vector (as described above), the expression vector is introduced into a host cell (as described above) and the Prdm16 protein is expressed in the host cell. The Prdm16 protein can then be isolated from the cells by an appropriate purification scheme using standard protein purification techniques. Alternative to recombinant expression, a Prdm16 protein, polypeptide, or peptide can be synthesized chemically using standard peptide synthesis techniques. Moreover, native Prdm16 protein can be isolated from cells (e.g., brown adipocytes), for example using an anti-Prdm16 antibody (described further below).

The invention also provides Prdm16 chimeric or fusion proteins. As used herein, a Prdm16 "chimeric protein" or "fusion protein" comprises a Prdm16 polypeptide operatively linked to a non-Prdm16 polypeptide. A "Prdm16 polypeptide" refers to a polypeptide having an amino acid sequence corresponding to Prdm16, whereas a "non-Prdm16 polypeptide" refers to a polypeptide having an amino acid sequence corresponding to a protein which is not substantially homologous to the Prdm16 protein, e.g., a protein which is different from the Prdm16 protein and which is derived from the same or a different organism. Within the fusion protein, the term "operatively linked" is intended to indicate that the Prdm16 polypeptide and the non-Prdm16 polypeptide are fused in-frame to each other. The non-Prdm16 polypeptide can be fused to the N-terminus or C-terminus of the Prdm16 polypeptide. For example, in one embodiment the fusion protein is a GST-Prdm16 fusion protein in which the Prdm16 sequences are fused to the C-terminus of the GST sequences. Such fusion proteins can facilitate the purification of recombinant Prdm16. In another embodiment, the fusion protein is a Prdm16 protein containing a heterologous signal sequence at its N-terminus. In certain host cells (e.g., mammalian host cells), expression and/or secretion of Prdm16 can be increased through use of a heterologous signal sequence.

Preferably, a Prdm16 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A Prdm16-encoding nucleic acid can be cloned into such an expression vector such that the fusion moiety is linked in-frame to the Prdm16 protein.

The present invention also pertains to homologues of the Prdm16 proteins which function as either a Prdm16 agonist (mimetic) or a Prdm16 antagonist. In a preferred embodiment, the Prdm16 agonists and antagonists stimulate or inhibit, respectively, a subset of the biological activities of the naturally occurring form of the Prdm16 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the Prdm16 protein.

Homologues of the Prdm16 protein can be generated by mutagenesis, e.g., discrete point mutation or truncation of the Prdm16 protein. As used herein, the term "homologue" refers to a variant form of the Prdm16 protein which acts as an agonist or antagonist of the activity of the Prdm16 protein. An agonist of the Prdm16 protein can retain substantially the same, or a subset, of the biological activities of the Prdm16 protein. An antagonist of the Prdm16 protein can inhibit one or more of the activities of the naturally occurring form of the Prdm16 protein, by, for example, competitively binding to a downstream or upstream member of the Prdm16 cascade which includes the Prdm16 protein. Thus, the mammalian Prdm16 protein and homologues thereof of the present invention can be, for example, either positive or negative regulators of adipocyte differentiation and/or thermogenesis in brown adipocytes.

In an alternative embodiment, homologues of the Prdm16 protein can be identified by screening combinatorial libraries of mutants, e.g., truncation mutants, of the Prdm16 protein for Prdm16 protein agonist or antagonist activity. In one embodiment, a variegated library of Prdm16 variants is generated by combinatorial mutagenesis at the nucleic acid level and is encoded by a variegated gene library. A variegated library of Prdm16 variants can be produced by, for example, enzymatically ligating a mixture of synthetic oligonucleotides into gene sequences such that a degenerate set of potential Prdm16 sequences is expressible as individual polypeptides, or alternatively, as a set of larger fusion proteins (e.g., for phage display) containing the set of Prdm16 sequences therein. There are a variety of methods which can be used to produce libraries of potential Prdm16 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Prdm16 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the Prdm16 protein coding can be used to generate a variegated population of Prdm16 fragments for screening and subsequent selection of homologues of a Prdm16 protein. In one embodiment, a library of coding sequence fragments can be generated by treating a double stranded PCR fragment of a Prdm16 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Prdm16 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Prdm16 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Prdm16 homologues (Arkin and Youvan (1992) *Proc. Natl. Acad. Sci. USA* 89:7811-7815; Delagrave et al. (1993) *Protein Engineering* 6(3):327-331).

In one embodiment, an isolated Prdm16 protein, or a portion or fragment thereof, can be used as an immunogen to generate antibodies that bind Prdm16 using standard techniques for polyclonal and monoclonal antibody preparation. The full-length Prdm16 protein can be used or, alternatively, antigenic peptide fragments of Prdm16 can be used as immunogens. A Prdm16 immunogen typically is used to prepare antibodies by immunizing a suitable subject, (e.g., rabbit, goat, mouse or other mammal) with the immunogen. An appropriate immunogenic preparation can contain, for example, recombinantly expressed Prdm16 protein or a chemically synthesized Prdm16 peptide. The preparation can further include an adjuvant, such as Freund's complete or incomplete adjuvant, or similar immunostimulatory agent. Immunization of a suitable subject with an immunogenic Prdm16 preparation induces a polyclonal anti-Prdm16 antibody response.

Accordingly, another aspect of the invention pertains to the use of anti-Prdm16 antibodies. The term "antibody" as used herein refers to immunoglobulin molecules and immunologically active portions of immunoglobulin molecules, i.e., molecules that contain an antigen binding site which specifically binds (immunoreacts with) an antigen, such as prdm16. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Prdm16. The term "monoclonal antibody" or "monoclonal antibody composition", as used herein, refers to a population of antibody molecules that contain only one species of an antigen binding site capable of immunoreacting with a particular epitope of Prdm16. A monoclonal antibody composition thus typically displays a single binding affinity for a particular Prdm16 protein with which it immunoreacts.

Polyclonal anti-Prdm16 antibodies can be prepared as described above by immunizing a suitable subject with a Prdm16 immunogen. The anti-Prdm16 antibody titer in the immunized subject can be monitored over time by standard techniques, such as with an enzyme linked immunosorbent assay (ELBA) using immobilized Prdm16. If desired, the antibody molecules directed against Prdm16 can be isolated from the mammal (e.g., from the blood) and further purified by well known techniques, such as protein A chromatography to obtain the IgG fraction. At an appropriate time after immunization, i.e., when the anti-Prdm16 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a Prdm16 immunogen as described above, and the culture supernatants of the resulting hybridoma cells are screened to identify a hybridoma producing a monoclonal antibody that binds Prdm16.

Any of the many well-known protocols used for fusing lymphocytes and immortalized cell lines can be applied for the purpose of generating an anti-Prdm16 monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Prdm16, i.e., using a standard ELISA assay.

Alternative to preparing monoclonal antibody-secreting hybridomas, a monoclonal anti-Prdm16 antibody can be identified and isolated by screening a recombinant combinatorial immunoglobulin library (e.g., an antibody phage display library) with Prdm16 to thereby isolate immunoglobulin library members that bind Prdm16. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-Prdm16 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-Prdm16 antibody (e.g., monoclonal antibody) can be used to isolate Prdm16 by standard techniques, such as affinity chromatography or immunoprecipitation. An anti-Prdm16 antibody can facilitate the purification of natural Prdm16 from cells and of recombinantly produced Prdm16 expressed in host cells. Moreover, an anti-Prdm16 antibody can be used to detect Prdm16 protein (e.g., in a cellular lysate or cell supernatant) in order to evaluate the abundance and pattern of expression of the Prdm16 protein. Anti-Prdm16 antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In vivo techniques for detection of Prdm16 protein include introducing into a subject a labeled antibody directed against the protein. For example, the antibody can be labeled with a radioactive marker whose presence and location in a subject can be detected by standard imaging techniques.

IV. Methods of the Invention

The methods of the invention relate the induction of Prdm16 expression sufficient to activate brown fat cell differentiation, wherein the differentiated brown fat cells increase energy expenditure to thereby treat obesity or an obesity related disorder, e.g., Type II diabetes.

The invention also relates to methods for increasing energy expenditure in a mammal comprising inducing Prdm16 expression sufficient to activate brown fat cell differentiation in the mammal, wherein the differentiated brown fat cells promote energy expenditure thereby increasing energy expenditure in the mammal.

The term "sufficient to activate" is intended to encompass any increase in Prdm16 expression that promotes, activates, stimulates, enhances, or results in brown fat differentiation. In another aspect, the invention relates to methods for treating obesity or an obesity-related disorder, e.g., Type II diabetes, in a subject comprising administering to the subject an agent that induces expression of Prdm16, wherein Prdm16 expression increases respiration and energy expenditure to thereby treat obesity or an obesity-related disorder. In one embodiment, total respiration is increased following the induction of Prdm16 expression. In another embodiment, uncoupled respiration is increased following the induction of Prdm16 expression. Uncoupled respiration dissipates heat and thereby increases energy expenditure in the subject.

As used herein, the term "agent" and "therapeutic agent" is defined broadly as anything that cells from a subject with obesity or an obesity-related disorder may be exposed to in a therapeutic protocol.

The term "administering" is intended to include routes of administration which allow the agent to perform its intended function of increasing Prdm16 expression and/or activity. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo.

The term "effective amount" of an agent that induces Prdm16 expression and/or activity is that amount necessary or sufficient to promote Prdm16 expression and/or activity in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular respiration uncoupling agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances. U.S. Pat. No. 5,427,916, for example, describes a method for predicting the effectiveness of antineoplastic therapy in individual subjects, and illustrates certain methods which can be used in conjunction with the treatment protocols of the instant invention.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular respiration uncoupling agent to treat obesity or obesity-related disorders can be monitored by comparing two or more samples obtained from a subject undergoing anti-obesity or obesity-related disorder treatment. In general, it is preferable to obtain a first sample from the subject prior to beginning therapy and one or more samples during treatment. In such a use, a baseline of expression of cells from subjects with obesity or obesity-related disorders prior to therapy is determined and then changes in the baseline state of expression of cells from subjects with obesity or obesity-related disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with obesity or obesity-related disorders is increasing or decreasing.

Another aspect of the invention relates to a method for identifying a compound or agent (e.g., peptides, peptidomimetics, small molecules or other drugs) capable of inducing the expression and/or activity of Prdm16.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell, which expresses Prdm16 is contacted with a test compound and the ability of the test compound to stimulate Prdm16 expression is determined. Determining the ability of the test compound to stimulate Prdm16 expression can be accomplished by, for example, antibody-based or PCR-based assays. The cell, for example, can be of mammalian origin, e.g., a liver cell, a skeletal muscle cell, or a fat cell, such as an adipocyte.

In an alternative embodiment, determining the ability of the test compound to stimulate Prdm16 expression can be accomplished by determining the ability of Prdm16 to further modulate the activity of a downstream effector of a Prdm16 target molecule.

In another embodiment, a method for identifying a compound capable of inducing the activity of Prdm16 comprising contacting a cell expressing Prdm16 with a test compound and assaying the ability of a test compound to stimulate the activity of Prdm16, which results in increased respiration (i.e., total and uncoupled respiration) of the cell. Respiration may be measured by oxygen consumption.

In another embodiment, agents are identified in a method wherein a cell is contacted with a candidate compound and the expression of Prdm16, e.g., mRNA or polypeptide levels, in the cell is determined. The level of expression of Prdm16 mRNA or polypeptide levels in the presence of the candidate compound is compared to the level of expression of Prdm16 mRNA or polypeptide in the absence of the candidate compound, and/or compared to the level of expression of Prdm16 mRNA or polypeptide in the presence of a known respiration uncoupling agent. The candidate compound can then be identified as a modulator of Prdm16 expression based on this comparison. For example, when expression of Prdm16 mRNA or polypeptide is greater (statistically significantly greater) in the presence of the candidate compound than in its absence, the candidate compound is identified as an agent that induces Prdm16 expression. Alternatively, when expression of Prdm16 mRNA or polypeptide is less (statistically significantly less) in the presence of the candidate compound than in its absence, the candidate compound is likely not an agent that induces or stimulates Prdm16 expression. Likewise, when expression of Prdm16 mRNA or polypeptide is substantially similar (i.e., not statistically different) to the expression in the presence of a known agent, the candidate compound is identified as an agent that does not stimulate Prdm16 expression. The level of Prdm16 mRNA or polypeptide expression in the cells can be determined by methods described herein for detecting Prdm16 mRNA or polypeptide.

In another aspect, the invention pertains to a combination of two or more of the assays described herein. For example, a test compound can be identified using a cell-based or a cell-free assay, and the ability of the agent to stimulate Prdm16 expression can be confirmed in vivo, e.g., in an animal such as an animal model for obesity or diabetes. Examples of animals that can be used include the transgenic mouse described in U.S. Pat. No. 5,932,779 that contains a mutation in an endogenous melanocortin-4-receptor (MC4-R) gene; animals having mutations which lead to syndromes that include obesity symptoms (described in, for example, Friedman, J. M. et al. (1991) *Mamm. Gen.* 1:130-144; Friedman, J. M. and Liebel, R. L. (1992) *Cell* 69:217-220; Bray, G. A. (1992) *Prog. Brain Res.* 93:333-341; and Bray, G. A. (1989) *Amer. J. Clin. Nutr.* 5:891-902); the animals described in Stubdal H. et al. (2000) *Mol. Cell. Biol.* 20(3):878-82 (the mouse tubby phenotype characterized by maturity-onset obesity); the animals described in Abadie J. M. et al. *Lipids* (2000) 35(6):613-20 (the obese Zucker rat (ZR), a genetic model of human youth-onset obesity and type 2 diabetes mellitus); the animals described in Shaughnessy S. et al. (2000) *Diabetes* 49(6): 904-11 (mice null for the adipocyte fatty acid binding protein); the animals described in Loskutoff D. J. et al. (2000) *Ann. N.Y. Acad. Sci.* 902:272-81 (the fat mouse); or animals having mutations which lead to syndromes that include diabetes (described in, for example, Alleva et al. (2001) *J. Clin. Invest.* 107:173-180; Arakawa et al. (2001) *Br. J. Pharmacol.* 132:578-586; Nakamura et al. (2001) *Diabetes Res. Clin. Pract.* 51:9-20; O'Harte et al. (2001) *Regul. Pept.* 96:95-104; Yamanouchi et al. (2000) *Exp. Anim.* 49:259-266; Hoenig et al. (2000) *Am. J. Pathol.* 157:2143-2150; Reed et al. (2000) *Metabolism* 49:1390-1394; and Clark et al. (2000) *J. Pharmacol. Toxicol. Methods* 43:1-10). Other examples of animals that may be used include non-recombinant, non-genetic animal models of obesity such as, for example, rabbit, mouse, or rat models in which the animal has been exposed to either prolonged cold or long-term over-eating, thereby, inducing hypertrophy of BAT and increasing BAT thermogenesis (Himms-Hagen, J. (1990), supra).

This invention further pertains to novel agents identified by the above-described screening assays. Accordingly, it is within the scope of this invention to further use an agent identified as described herein in an appropriate animal model.

For example, an agent that induces expression of Prdm16 identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Monitoring the influence of agents (e.g., drugs) on obesity and obesity-related disorders can be applied not only in basic drug screening, but also in clinical trials. In such clinical trials, the expression of Prdm16 can be used as a "read out." In addition, genes, including Prdm16, that are modulated in cells by treatment with the putative agent can be identified. Thus, to study the effect of agents that induce Prdm16 expression on obesity and obesity-related disorders, for example, in a clinical trial, cells can be isolated and RNA prepared and analyzed for the levels of expression of Prdm16 and other genes implicated in the metabolism-associated disorder, respectively. The levels of gene expression (e.g., a gene expression pattern) can be quantified by northern blot analysis or RT-PCR, as described herein, or alternatively by measuring the amount of polypeptide produced, by one of the methods as described herein, or by measuring the levels of activity of Prdm16 or other genes. In this way, the gene expression pattern can serve as a marker, indicative of the physiological response of the cells to the agent. Accordingly, this response state may be determined before, and at various points during treatment of the individual with the agent.

Another aspect of the invention relates to a method for inducing brown fat cell differentiation in a mammal comprising expressing Prdm16 in preadipocyte cells; injecting the preadipocyte cells expressing Prdm16 into the mammal; and monitoring the differentiation of brown fat cells. Injection of preadipocytes may be by a subcutaneous or intravenous injection. Increased brown adipose tissue in the mammal will warm up the body and blood of the mammal resulting in an increased energy expenditure from the cells. The increased energy expenditure will increase the metabolic rate of the subject and may be used for the treatment and/or prevention of obesity and obesity related disorders.

Another aspect of the invention relates to a method of reducing brown fat cells comprising contacting cells expressing Prdm16 with the nucleic acid sequence set forth in SEQ ID NO: 7; and assaying for the reduction of brown fat cells. The reduction of brown fat cells may be monitored by 1) a decrease or failure to stimulate the expression of cidea, type II deiodinase, cig30, PGC-1α and ucp1; 2) a decrease or failure to stimulate the expression of mitochondrial genes including, cytochrome c, cox 4i1, cox III, cox 5b, atpase b2, cox II, atp5o and ndufb5; 3) a decrease in or failure to stimulate total respiration of a cell; 4) a decrease in or failure to stimulate uncoupled respiration of a cell; 5) a decrease in or failure to stimulate heat dissipation; 6) a decrease in or failure to stimulate thermogenesis; 7) decrease in or failure to stimulate energy expenditure.

V. Gene Therapy

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Feigner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) *Gene*, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

VI. Pharmaceutical Compositions

In another aspect, the present invention provides pharmaceutically acceptable compositions which comprise a therapeutically-effective amount of an agent that induces Prdm16 expression and/or activity formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that induces Prdm16 expression and/or activity, or composition comprising an agent that induces Prdm16 expression and/or activity, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that induce Prdm16 expression and/or activity encompassed by the invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that induce Prdm16 expression and/or activity. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that induces Prdm16 expression and/or activity with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that induces Prdm16 expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that induces Prdm16 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that induces Prdm16 expression and/or activity can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that induces Prdm16 expression and/or activity in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1

Prdm16 Directs the Development of Brown Adipose Cells and Increases Energy Expenditure Mammals possess two distinct types of fat tissue with competing metabolic roles. White adipocyte tissue (WAT) is specialized for the storage and release of triglycerides in response to changing systemic energy levels. Conversely, brown fat tissue (BAT) oxidizes fatty acids for the production of heat in response to cold-exposure or diet. Structurally, brown fat cells are characterized by densely packed mitochondria (responsible for brown color of tissue) and multiple lipid inclusions. White fat cells contain fewer mitochondria and store lipid within a single large vacuole that occupies almost the entire volume of the cell. A critical distinguishing feature between these two cell types is the specific expression of ucp1 protein in the inner mitochondrial membrane of brown fat cells. Ucp1 is a proton transporter that leaks protons across the mitochondrial inner membrane, thereby dissipating the electrochemical proton gradient normally used for ATP synthesis (Klingenberg, M. and S. G. Huang, Biochim Biophys Acta, 1999. 1415(2):271-96).

Brown fat is highly adapted to produce heat as a means of maintaining body temperature in cold environments. Many aspects of thermogenesis are controlled by the sympathetic nervous system. Sympathetic nerves release noradrenaline in the vicinity of brown adipocytes which respond by activating a G-protein signaling cascade mediated by β-adrenergic receptors. Cold exposure and high energy diets enhance SNS activity, whereas fasting reduces SNS activity (Rothwell, N. J. and M. J. Stock, Adv Nutr Res, 1983. 5:201-20; Cannon, B. and J. Nedergaard, Physiol Rev, 2004. 84(1):277-359). Norepinephrine stimulates the proliferation of brown preadipocytes (Nedergaard, J., et al., Exp Nephrol, 1994. 2(2):135; Bronnikov, G. et al., J Biol Chem, 1992. 267(3):2006-13) and promotes differentiation, mitochondrial biogenesis and ucp1 expression in mature adipocytes (Puigserver, P., et al., Cell, 1998. 92(6):829-39; Gomez-Ambrosi, J. et al. Mol Cell Endocrinol, 2001. 176(1-2):85-90). Lipolysis, the process by which triglycerides are broken down into free fatty acids, is also activated by norepinephrine and crucial for thermogenesis. It is thought that fatty acids activate the uncoupling function of ucp1 in addition to providing the substrate for mitochondrial β-oxidation (Cannon, B. and J. Nedergaard, Physiol Rev, 2004. 84(1):277-359; Matthias, A., et al., J Biol Chem, 2000. 275(33):25073-81).

Unlike rodents and other small mammals that retain brown fat as adults, humans quickly lose their brown fat after birth. Newborn humans possess abundant brown fat required for non-shivering thermogenesis to defend their body temperature (Lean, M. E., et al., Clin Sci (Lond), 1986. 71(3):291-7). As humans age, BAT is uniformly replaced by WAT. Significantly, a small number of brown adipocytes and detectable levels of ucp1 mRNA are found in adult white adipose depots (Garruti, G. and D. Ricquier, Int J Obes Relat Metab Disord, 1992. 16(5):383-90; Oberkofler, H., et al., J Lipid Res, 1997. 38(10):2125-33). The presence of these ucp1 expressing, multilocular fat cells in adult tissue suggests that reactivation of the brown fat program can be achieved. Furthermore, BAT and oxidative activity can be increased by chronic cold exposure in humans (Huttunen, P., et al., Eur J Appl Physiol Occup Physiol, 1981. 46(4):339-45). Experiments in rodents also demonstrate that prolonged cold exposure or β3-adrenergic stimulation induces the expression of ucp1 in white fat (Himms-Hagen, J., et al., Am J Physiol Cell Physiol, 2000. 279(3):C670-81). Genetic studies in mice show that the proportion of brown fat cells resident in white fat is a complex trait influenced my multiple loci (Guerra, C., et al., J Clin Invest, 1998. 102(2):412-20; Xue, B., et al., Mol Cell Biol, 2005. 25(18):8311-22). These brown adipocytes have three possible origins: the interconversion of mature white adipocytes, the differentiation of committed progenitors, or the directed differentiation of bipotential progenitors. Further studies are required to characterize the ontogeny of these cells and determine whether they represent bona-fide "brown adipocytes".

Brown Fat Thermogenesis in Energy Homeostasis

A role for brown fat thermogenesis in regulating energy balance and body weight is suggested by several lines of experimental evidence in mice and rats. Firstly, BAT is recruited and activated in response to calorie dense diets (Lupien, J. R., et al., Am J Physiol, 1985. 249(6 Pt 2):R694-8; Glick, Z., et al., Am J Physiol, 1985. 249(5 Pt 1):E519-24). Increased ucp1 expression in mouse fat promotes energy expenditure, reduces adiposity and protects animals from diet-induced and genetic forms of obesity (Guerra, C., et al., J Clin Invest, 1998. 102(2):412-20; Cederberg, A., et al., Cell, 2001. 106(5):563-73; Tsukiyama-Kohara, K., et al., Nat Med, 2001. 7(10):1128-32; Ghorbani, M. and J. Himms-Hagen, Int J Obes Relat Metab Disord, 1997. 21(6):465-75). For instance, mice expressing a ucp1 transgene in white fat display reduced adiposity and are protected against the development of obesity and diabetes (Kopecky, J., et al., J Clin Invest, 1995. 96(6):2914-23; Kopecky, J., et al., Am J Physiol, 1996. 270(5 Pt 1):E768-75). Consistent with a role for thermogenesis in body weight regulation, mice with atrophied brown fat exhibit increased adiposity and metabolic disease correlating with obesity (Lowell, B. B., et al., Nature, 1993. 366(6457):740-2). Paradoxically however, ucp1-deficient mice are also lean and resistant to obesity (Enerback, S., et al., Nature, 1997. 387(6628):90-4). This result has been interpreted to suggest the existence of alternative, less energy efficient thermoregulatory mechanisms in the absence of functional brown fat. The enormous oxidative capacity of BAT suggests that even a small amount of this tissue could contribute to overall energy expenditure. Strategies to enhance the recruitment and function of human BAT can therefore increase energy expenditure and limit the storage of triglycerides in white fat.

Brown Adipose Differentiation

Adipogenic differentiation has been investigated using cell lines that typically give rise to white adipocytes. Preadipocytes are specialized fibroblast-like cells contained in white and brown adipose depots that differentiate into mature fat storing adipocytes in response to hormones (Gregoire, F. M., et al., Physiol Rev, 1998. 78(3):783-809; Sorisky, A., Crit. Rev Clin Lab Sci, 1999. 36(1):1-34). Preadipocytes isolated from white and brown fat tissue appear to be "committed" since fibroblasts cultured from brown depots differentiate as brown fat cells whereas those from white tissue differentiate as white adipocytes (Klaus, S., et al., J Cell Sci, 1995. 108 (Pt 10):3171-80). Based on in vitro models, BAT and WAT, although functionally distinct, activate a similar transcriptional cascade during their differentiation.

Members of the c/ebp (CCAAT enhancer binding protein) and ppar (peroxisome-proliferator activated receptor) families of transcription factors play important roles in adipogenic differentiation. Specifically, transient expression of c/ebpβ and c/ebpγ after hormone induction is followed by the induction of pparγ and c/ebpα (Rosen, E. D. and B. M. Spiegelman, Annu Rev Cell Dev Biol, 2000. 16:145-71). Pparγ and c/ebpα then orchestrate the program of adipocyte differentiation including activation of lipogenic and structural genes. Based on genetic loss-of-function experiments, pparγ is essential for the differentiation of both brown and white adipocytes (Rosen, E. D., et al., Mol Cell, 1999. 4(4):611-7; Rosen, E. D., et al., Genes Dev, 2000. 14(11):1293-307; Barak, Y., et al., Mol Cell, 1999. 4(4):585-95). In brown fat, activated pparγ appears to contribute to recruitment of new cells and ucp1 induction in response to adrenergic signaling (Mercer, S. W. and P. Trayhurn, FEBS Lett, 1986. 195(1-2):12-6; Rothwell, N. J., et al., Mol Cell Endocrinol, 1987. 51(3):253-7; Foellmi-Adams, L. A., et al., Biochem Pharmacol, 1996. 52(5):693-701).

An important molecular distinction between white and brown fat has been elucidated recently with the identification of pgc1α (pparγ coactivator-1α). Pgc1α was isolated from brown fat as a pparγ coactivator protein that was dramatically induced after cold-exposure (Puigserver, P., et al., Cell, 1998. 92(6):829-39). Since its discovery, pgc1α has been shown to be a master regulator of mitochondrial biogenesis, muscle fiber type switching and liver gluconeogenesis (Puigserver, P., et al., Nature, 2003. 423(6939):550-5; Rhee, J., et al., Proc Natl Acad Sci USA, 2003. 100(7):4012-7; Yoon, J. C., et al., Nature, 2001. 413(6852):131-8; Lin, J., et al., Nature, 2002. 418(6899):797-801). In brown fat cells, pgc1α induces mitochondrial biogenesis and directly stimulates ucp1 expression (Puigserver, P., et al., Cell, 1998. 92(6): 29-39). Significantly, overexpression of pgc1α in human white adipocytes is sufficient for the induction of ucp1 and other features of brown fat (Tiraby, C., et al., J Biol Chem, 2003. 278(35):33370-6). Consistent with an essential role in brown fat, pgc1α-deficient mice are cold-intolerant and express decreased levels of ucp1 (Lin, J., et al., Cell, 2004. 119(1):121-35). These results indicate that pgc1α is not required for the formation of brown adipocytes, but is essential for activating the thermogenic program during cold exposure. Pparα, a nuclear hormone receptor closely related to pparγ, is also expressed at higher levels in brown fat and likely regulates enzymes involved in fatty acid oxidation. Although pgc1α is an important component of brown fat cells, there are clearly other factors that function upstream of pgc1α for the determination and differentiation of this cell lineage.

Recent studies implicate a role for pRb (retinoblastoma) and p107 in regulating the decision for preadipocytes to undergo white versus brown adipogenesis (Scime, A., et al., Cell Metab, 2005. 2(5):283-95; Hansen, J. B., et al., Proc Natl Acad Sci USA, 2004. 101(12):4112-7). Rb protein appears to be enriched in white relative to brown fat precursors. Notably, Rb-deficient fibroblasts or primary preadipocytes undergo brown fat differentiation and express all the characteristic markers of brown fat (Scime, A., et al., Cell Metab, 2005. 2(5):283-95; Hansen, J. B., et al., Proc Natl Acad Sci USA, 2004. 101(12):4112-7). Mechanistically, Rb has been implicated as a direct repressor of pgc1α gene expression (Scime, A., et al., Cell Metab, 2005. 2(5):283-95). Future experiments investigating the nature of this pathway in vivo will reveal its importance to brown fat determination.

Transcriptional regulation of the ucp1 gene has been the subject of intense investigation. By reporter gene studies, two regulatory regions have been described—a proximal promoter and a distal enhancer region about 3 kb upstream of the start site (Cannon, B. and J. Nedergaard, Physiol Rev, 2004. 84(1):277-359). Adrenergic control of ucp1 transcription is mediated by cAMP response (CRE) elements in both regulatory regions that interact with CREB (cAMP response element binding protein) and ATF2 (Activating Transcription Factor-2) (Kozak, U. C., et al., Mol Cell Biol, 1994. 14(1): 59-67). Particularly important is a PPRE (ppar response element) in the distal ucp1 enhancer that recruits pgc1α to the ucp1 promoter and likely mediates the stimulatory effects of pparγ agonists. Activated thyroid receptor (TR) acts through a thyroid response element in the distal enhancer to enhance the effect of norepinephrine on ucp1 expression (Rabelo, R., et al., Endocrinology, 1995. 136(3):1003-13; Rabelo, R., et al., Endocrinology, 1996. 137(8):3478-87). Type-II deiodinase expressed in brown adipocytes catalyzes the conversion of thyroxine (T4) to 3,5,3'-tri-iodothyronine (T3) which binds to and activates TR (Pavelka, S., et al., Biochem J, 1993. 292 (Pt 1):303-8; Leonard, J. L. et al., Endocrinology, 1983. 112 (3):1153-5). Recently, p38 MAPK (Mitogen Activated Protein Kinase) has been demonstrated as a key regulator of thermogenesis through its induction of ucp1 gene expression via activation of ATF2 and pgc1α (Cao, W., et al., Mol Cell Biol, 2004. 24(7):3057-67). Identifying the tissue-specific factors and mechanisms that restrict ucp1 expression to brown fat is a promising strategy to approach the question of lineage commitment.

Identification of Prdm16 as a Regulator of Brown Adipose Differentiation

The role of transcription factors as master regulators of developmental and metabolic gene programs is well documented. The regulated expression of a single transcription factor or transcriptional coactivator can control the execution of complicated genetic programs. Transcription factors are often expressed at low levels relative to other classes of genes, and therefore changes in their mRNA levels are more difficult to assay and interpret by conventional methods.

To identify transcription factors expressed differentially in white and brown fat tissues, an RT-PCR screen was conducted using primers specific to all mouse transcription factors. This collection has been used successfully to examine transcription factor expression in mouse brain development (Gray, P. A., et al., Science, 2004. 306(5705):2255-7). The expression of ~1700 factors was assayed in brown and white tissue samples from adult mice. Several transcription factors including Prdm16 (PR-domain containing protein-16) were identified as being differentially expressed in brown versus white fat. The uniform correlation of Prdm16 expression in all brown fat tissues and cell lines and its absence in corresponding samples of white fat strongly suggested a role in brown versus white fat development and physiology (FIG. 4). Moreover, Prdm16 expression was induced during brown adipogenesis (FIG. 4). Prdm16 mRNA, however, was not induced during acute cold exposure and is therefore not cold sensitive. The PR domain (PRDI-BF1-RIZ homology region) is related to the well-characterized SET domain, which functions in chromatin remodeling and lysine methylation. Prdm16 is a zinc finger containing transcription factor expressed in leukemias that carry a particular chromosomal translocation (Lahortiga, I., et al., Oncogene, 2004. 23(1):311-6; Barjesteh van Waalwijk van Doorn-Khosrovani, S., et al., Exp Hematol, 2003. 31(11):1066-72; Nishikata, I., et al., Blood, 2003. 102 (9):3323-32; Mochizuki, N., et al., Blood, 2000. 96(9):3209-14). Overexpression of Prdm16 has been associated with leukemogenesis and inhibition of myeloid differentiation (Nishikata, I., et al., Blood, 2003. 102(9):3323-32). Favorable disease outcome in these leukemias is correlated with the lowest levels of Prdm16 expression (Barjesteh van Waalwijk van Doorn-Khosrovani, S., et al., Exp Hematol, 2003. 31(11): 1066-72). The chromosomal translocations associated with leukemia appear to disrupt the normal control of prdm16 transcription such that it is expressed at higher levels and inappropriately induced during differentiation of hematopoietic lineages. A role for Prdm16 outside of the blood system has not been reported.

Prdm16 expression was localized to the nucleus using a Flag-tagged Prdm16 and anti-Flag tagged antibodies. Expression in the nucleus is consistent with it role as a transcription factor.

Prdm16 Directs Brown Fat Cell Differentiation

Full-length mouse Prdm16 cDNA was cloned into a retroviral expression vector to allow for high-level stable expression in various cell lines. For example, ppar$\gamma^{-/-}$ cells were transduced with ppar$\gamma$ alone or ppar$\gamma$ together with prdm16. Ppar$\gamma^{-/-}$ cells were selected as a model system since they have absolutely no fat character whatsoever in the absence of ppar$\gamma$. Stable Prdm16 and control lines were subjected to adipogenic differentiation protocols and treated with cAMP to mimic β-adrenergic signaling. The ppar$\gamma$-control fibroblasts gave rise to white adipocytes whereas Prdm16 expressing cells activated classical markers of brown fat including cidea, cig30, pgc1α, type II deiodinase, and ucp1 (FIGS. 5A-D). As in true BAT cells, ucp1, type II deiodinase and pgc1α were further induced upon treatment with cAMP. This data illustrate a role for Prdm16 in the regulation of brown fat differentiation and function. Brown fat cells are also characterized by densely packed mitochondria responsible for their increased energy expenditure. Notably, Prdm16 expressing cells displayed significantly expression of several mitochondrial genes including cytochrome c (cyt c), cox 4i1, coxIII, cox5b, atpase b2, etc. (FIG. 6). Further, PGC-1α and ucp1 are induced by Prdm16 are induced in the absence of PPARγ.

In contrast, Rb expression is reduced approximately twofold following overexpression of Prdm16 in the presence of PPARγ. As indicated above, Rb protein appears to be enriched in white fat cells compared to brown fat cell precursors.

Figure 7A:
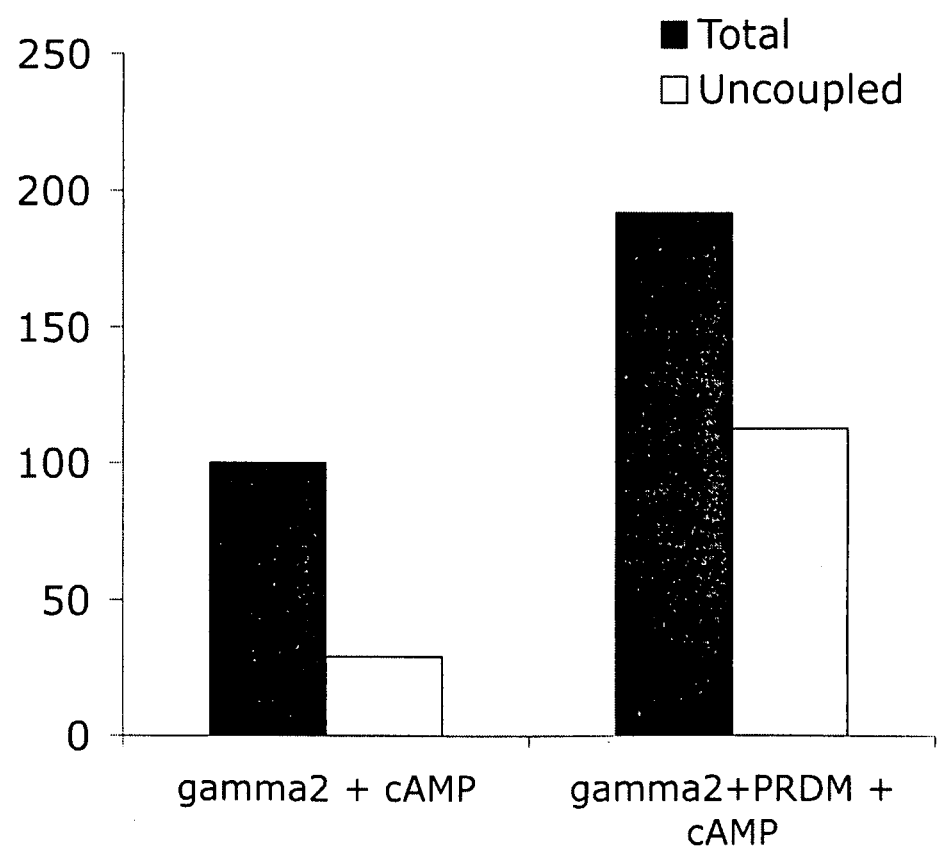
FIG. 7A is a graph showing induction of total and uncoupled respiration by Prdm16 in the presence of pparγ 2 and cAMP.
Figure 7B:
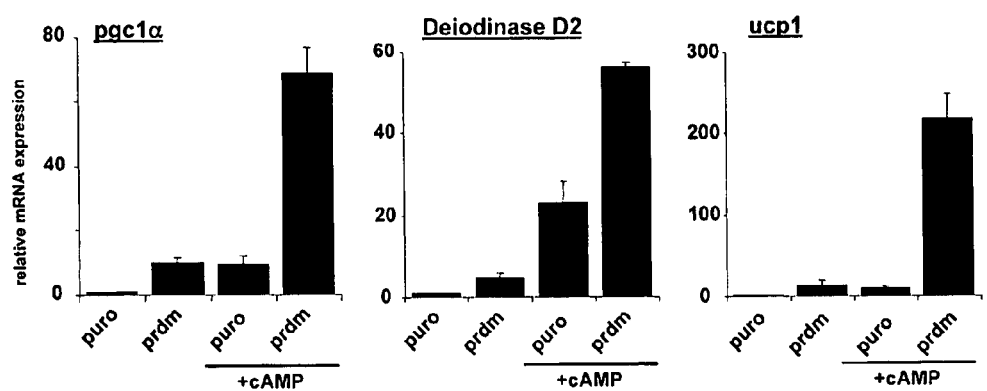
FIG. 7B is a graph showing cAMP-regulated brown fat cell genes as highly induced in Prdm16-expressing fat cells.

To determine the functional consequence of Prdm16 expression in fat cells, total and uncoupled respiration was measured in control and Prdm16 expressing fat cells. Fat cells expressing Prdm16 showed a significant increase in both total and uncoupled respiration as measured by oxygen consumption (FIG. 7A). cAMP-regulated brown fat cell genes are also highly induced in Prdm16-expressing fat cells (FIG. 7B). This data demonstrates that Prdm16 has a dramatic effect on energy expenditure. The approximate four-fold increase in uncoupled respiration is presumably attributed to the increase in ucp1 gene expression. Thus, these results indicate a powerful role for Prdm16 in directing the development of brown fat cells.

A requirement for Prdm16 in Brown Fat Cell Development and Function

The examples above indicate that prdm16 expression is sufficient to activate the brown fat cell differentiation program in white fat progenitors. To determine whether Prdm16 is necessary for the development and function of brown fat, siRNA technology was employed to deplete Prdm16 mRNA in bona-fide brown fat cells. Immortalized brown fat preadipocytes were generated from the interscapular brown adipose of newborn mice. These preadipocytes are able to undergo brown adipose differentiation in culture characterized by the specific expression of brown fat cell genes including cidea, cig30, pgc1α and ucp1. Furthermore, ucp1 and pgc1α are inducible by cAMP levels in these cells.

Figure 8:
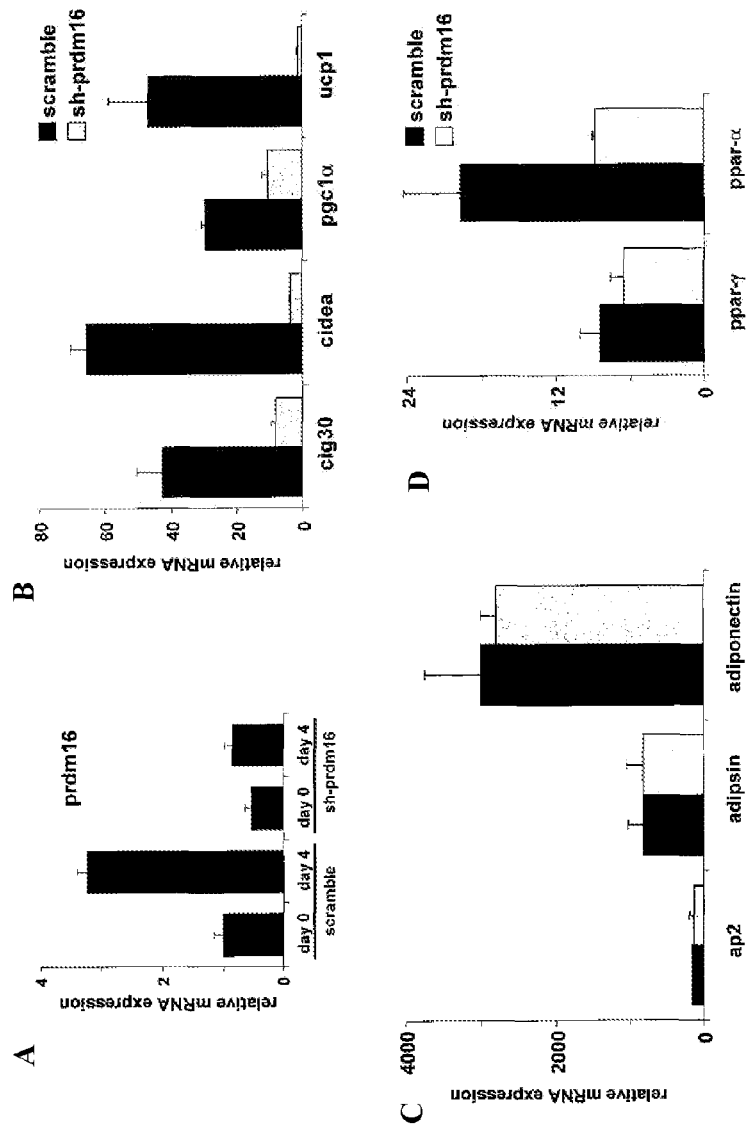
FIG. 8 shows a series of graphs showing reduced expression of Prdm16 RNA and brown fat markers following knockdown of Prdm16 by expressing shRNA using retrovirus in cells stably expressing a short hairpin RNA expressed from adenovirus (si-1 and si-3). The graphs show relative mRNA levels of prdm16 (A), and brown fat cell genes, including cig30, cidea, pgc1α, and ucp1 (B); ap2, adipsin, and adiponectin (C); and ppar-γ and ppar-α (D).

Knockdown of prdm16 RNA was accomplished by stably expressing an shRNA using retrovirus. The shRNA sequences used herein were gaagagcgugaguacaaa (referred to as si-3; SEQ ID NO: 7) and caacgaacagauuuacuau (referred to as si-1; SEQ ID NO: 8). Prdm16 mRNA was reduced by approximately 90% (FIG. 8A-B) and this reduction of Prdm16 results in a significant reduction in the expression of brown fat markers including cig30 and cidea, pgc1α, and ucp1 (FIG. 8C-D). These results suggest that Prdm16 is at least partially required for the proper differentiation of brown fat.

Example 2

Prdm16 Stimulates gal4-pgc1α Activity

To determine whether prdm16 and the pgc1 coactivators interact, a gal4 based transactivation assay was employed. Gal4-pgc1 was generated by fusing the DNA binding domain of the yeast gal4 protein with the full-length coding sequence of either pgc1α or pgc1β. After transfection into cells, the Gal4-pgc1 fusion protein binds to its recognition sequence in a Gal1 reporter plasmid and activates expression of the luciferase gene.

In this experiment, the reporter plasmid (UAS-Firefly Luciferase) was transfected along with either control plasmid+/−Prdm16 plasmid, gal4-pgc1α+/−Prdm16, or gal4-pgc1β+/−prdm16 into cos7 cells. 100 ng of UAS-Firefly Luciferase reporter, 10 ng of gal4-pgc1 and 150 ng of pcDNA-Prdm16 and respective control plasmids were transfected using Superfect (Qiagen) in 6 well plates. 50 ng of a control plasmid expressing *Renilla*-luciferase was also included in all transfection mixes. Cells were lysed in Promega 1× lysis buffer to measure luciferase activity. Firefly luciferase activity was normalized for transfection efficiency by measuring *Renilla* luciferase in all samples.

Figure 9:
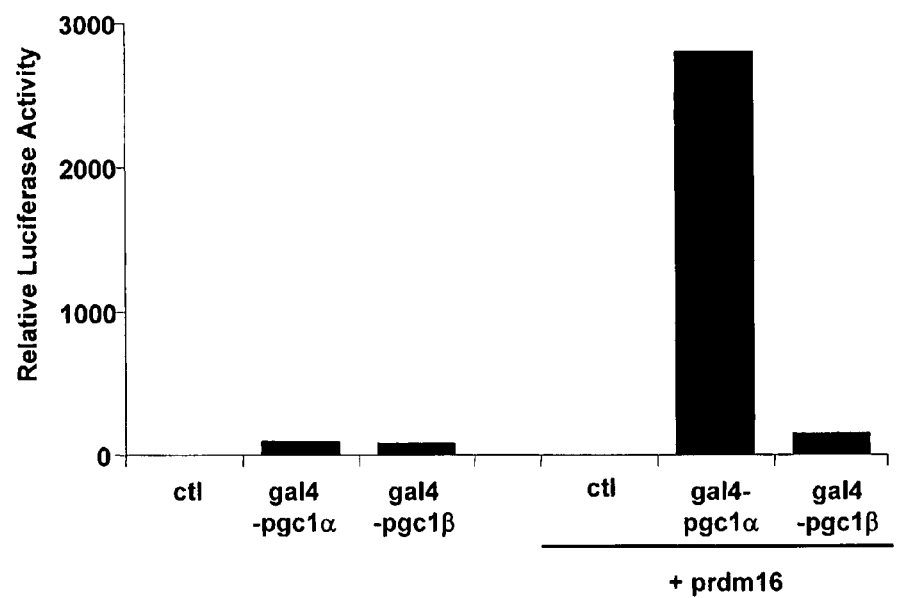
FIG. 9 is a graph showing ga14-pgc1α activation by Prdm16.

As shown in FIG. 9, the results of this experiment demonstrate that Prdm16 is a powerful activator of pgc1α activity. In cells expressing Prdm16, transactivation of the reporter by pgc1α was increased approximately 200 fold over control levels. Gal4-pgc1b however did not respond to Prdm16 expression demonstrating a specific relationship between prdm16 and pgc1α. These studies suggest the possibility that pgc1α and prdm16 proteins interact directly.

Prdm16 is Required for Expression of the Brown Fat Phenotype siRNA-mediated knockdown of prdm16 in brown fat cells was employed to determine whether Prdm16 is required for brown fat cell differentiation and function. Immortalized brown fat cells were established from wildtype C57 black6 mice using SV40 LargeT as previously described (Klein, et al., Bioessays, 2002). Retrovirus harboring short-hairpin RNA specific to Prdm16 or control scrambled sequences were introduced into brown preadipocytes. Stable cell lines expressing sh-Prdm16 or sh-scrambled were grown to confluence and induced to differentiate for 5 days by standard procedures using IBMX, Insulin, dexamethosone and Indomethacin (see Klein, 2002). At day 5, differentiated brown adipocytes were harvested for analysis of gene expression by real-time quantitative PCR. As demonstrated in FIG. 10, shRNA directed against Prdm16 was efficient in preventing the induction of Prdm16 that normally accompanies brown fat differentiation. As a result of Prdm16 depletion in brown fat cells, the expression of classical brown fat marker genes were specifically reduced including pgc1α, cig30, cidea, pparα and ucp1. Importantly, adipocyte genes that are expressed in brown as well as white fat cells were not affected by loss of prdm16 (e.g. ap2, adiponectin, pparγ). These results demonstrate that prdm16 is required for appropriate expression of the brown fat phenotype.

Prdm16 is Required for Brown Fat Differentiation from Primary Preadipocytes

Figure 11:
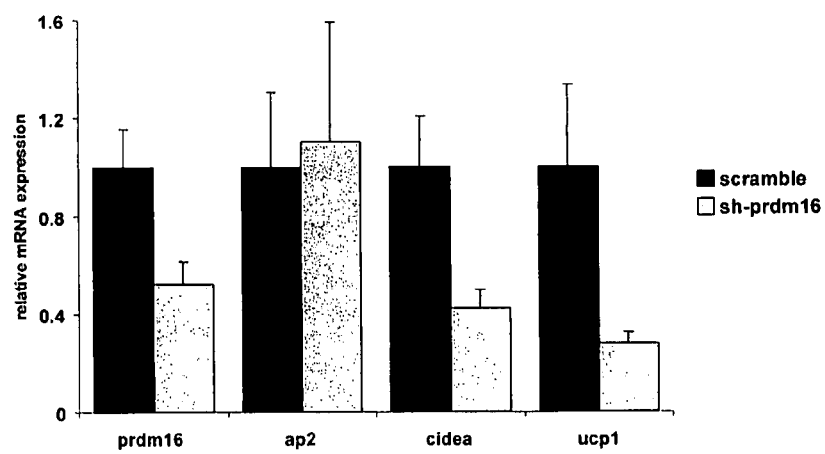
FIG. 11 is a graph showing reduced expression of brown fat cell markers in Prdm16-depleted primary brown fat cultures.

To further test the requirement for Prdm16 in brown fat cell development, primary preadipcoytes were isolated from newborn C57 black 6 mice. As cells neared confluence (day 2 in culture), the cells were infected with adenovirus-expressing either sh-prmd16 or control scrambled sequence at an M.O.I of 50. The transduction efficiency was assessed by GFP expression from recombinant adenoviruses. At confluence, cells were differentiated into brown adipocytes as above. 5 days after the start of differentiation, fat cells were harvested for analysis of gene expression. Adenoviral expression of sh-prdm16 in primary preadipocytes effectively knocked down the expression of prdm16 as well as other markers of brown fat cells including cidea and ucp1, without affecting the common fat cell genes such as ap2. As shown in FIG. 11, these results demonstrate a requirement for Prdm16 in the differentiation of brown fat cells.

Figure 12:
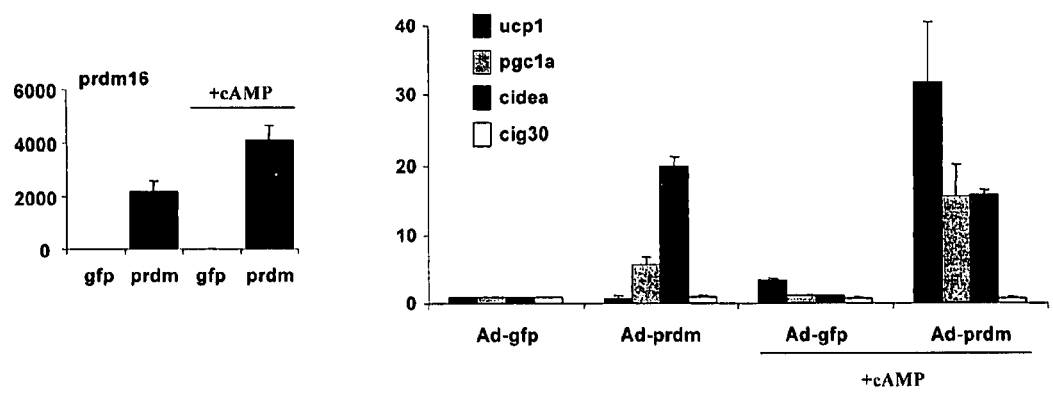
FIG. 12 is a bar graph showing brown fat gene induction by Prdm16 in mature white adipocytes.

Prdm16 Expression is Sufficient to Induce Brown Fat Cell Genes in Mature Adipocytes To test the ability of Prdm16 to direct the "conversion" of white fat cells to "brown" or "brown-like" fat, adenovirus expression vector was used to introduce the Prdm16 gene into mature adipocytes. In this experiment, pparγ-/- embryonic fibroblasts were transduced with retrovirus expressing pparγ to enable efficient control of differentiation with pparg-ligands. These cells differentiate as mature lipid packed white fat cells using the standard "313-L1 protocol". By extensive analysis of gene expression, all the classical fat cell markers are appropriately induced during the maturation of these cells including ap2, adiponectin, adipsin, FAS (fatty acid synthase), etc. At day 4 after differentiation, as cells express the mature adipocyte phenotype, cultures were transduced with adenovirus expressing Prdm16 or control virus at an M.O.I of 50. Cells were harvested 3 days after adenovirus infection to analyze gene expression. Remarkably, expression of Prdm16 in already-differentiated cells was sufficient to significantly induce several brown fat cell-specific markers including pgc1α, ucp1 and cidea. As in real brown fat cells, adipocytes expressing prdm16 were responsive to cAMP stimulation as observed by the induction of pgc1α and ucp1 following 5 hour incubation with 1 mM cAMP. Interestingly, cig30 expression was not elevated in Prdm16 expressing adipocytes. As shown in FIG. 12, these studies indicate that Prdm16 can influence the phenotype of terminally differentiated adipocytes and promote the conversion of white to brown-type adipocytes. It should be noted that the absolute levels of brown fat cell markers induced by Prdm16 in this experiment was substantially less than when Prdm16 is present throughout the differentiation procedure as demonstrated with retrovirus experiments.

Prdm16 Expressing Cells Acquire the Molecular Phenotype of Brown Fat In Vivo

To establish whether cells expressing Prdm16 were able to differentiate as brown fat or brown-fat like tissue in vivo, we performed cell transplantation experiments in nude mice (Foxn1 deficient). Nude mice were employed since they lack a fully functioning immune system and as such, do not reject foreign transplanted cells or tissue. Stable pparγ-/- cells expressing either pparγ or pparγ together with prdm16 were expanded as proliferating fibroblasts in cell culture. These cells grow readily and maintain their fibroblastic morphology while maintained under growth conditions. $1 \times 10^7$ subconfluent fibroblasts (pparγ/puro or pparγ/Prdm16) were trypsinized and suspended in 200 ul of complete growth medium (10% FBS/DMEM). A $28^{1/2}$ gauge insulin syringe was used to inject the cells subcutaneously just above the sternum in nude mouse recipients. This site of injection was chosen due to the lack of endogenous subcutaneous fat in this area. 6 weeks after cell transplantation, small but readily identifiable fat pads were observed at the site of injection. These fat pads were fixed in 4% paraformaldehyde for preparation of tissue sections and immunohistology. The ability for fibroblasts to differentiate as ectopic subcutaneous fat pads was first demonstrated by Green and Kehinde (J Cell Physiol., 1979). Presumably, the growth factors and microenvironment promotes the differentiation of adipose. This experimental model thus provides a convenient and adaptable genetic tool to study in vivo adipogenesis.

Figure 13:
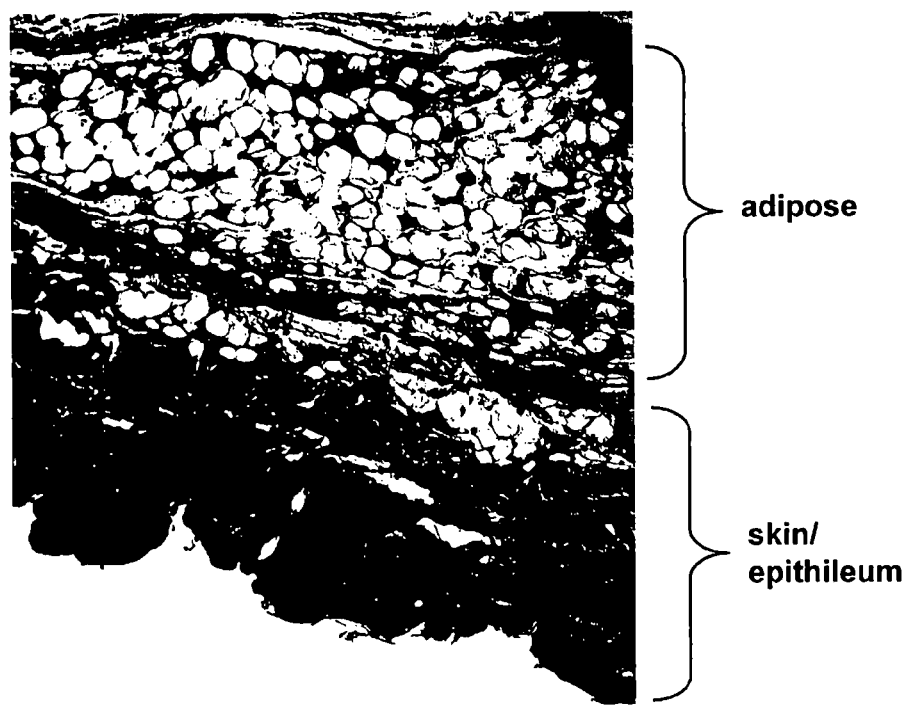
FIG. 13 is a photograph of an ectopic subcutaneous fat pad formation from implanted fibroblasts.
Figure 14:
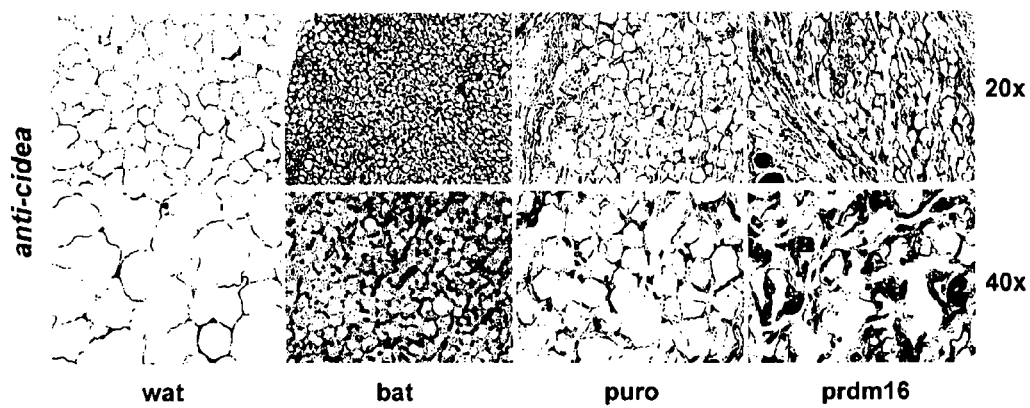
FIG. 14 are photographs showing the expression of brown fat markers in fat pads derived from Prdm16-expressing fibroblasts.
Figure 15:
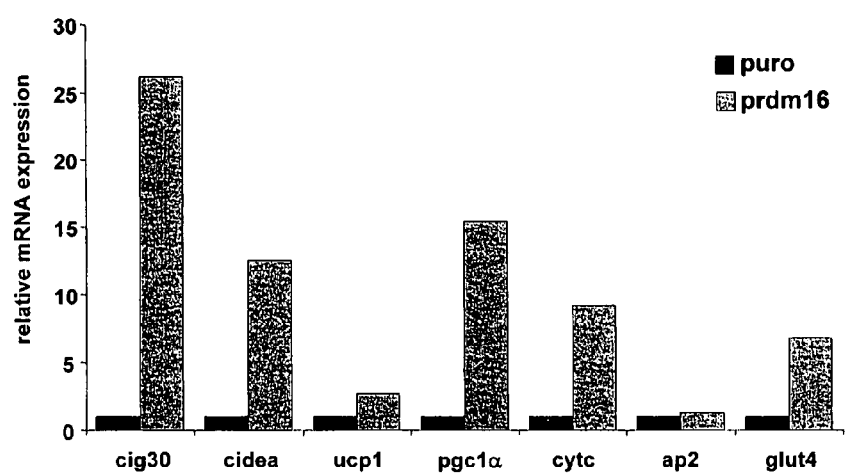
FIG. 15 is a bar graph showing increased expression of brown fat genes in fat pads derived form Prdm16-expressing fibroblasts.

FIG. 13 shows H&E staining of a representative transplant 6 weeks after implantation of $1 \times 10^7$ pparγ-/- cells that express pparγ and control puro vector. The fibroblasts were able to form a discrete fat pad under the skin as demonstrated by the presence of unilocular, fat containing adipocytes. FIG. 14 shows immunostaining of fat tissues derived from puro or Prdm16 expressing cells demonstrate increased expression of the classical brown fat cell protein, cidea (anti-Cidea: Chemicon). FIG. 15 clearly shows that brown fat markers are specifically enriched in fat tissue made from prdm16 expressing cells, as demonstrated by RNA analysis of ectopic fat pads. These studies show that Prdm16 can promote the appropriate differentiation of brown-fat like tissue in vivo.

Example 3

Expression of Prdm16 in Mammals

Prdm16 may be introduced into a mammal, human or non-human, to alter the metabolic rate of the mammal. Prdm16 nucleic acid may be expressed in a vector, e.g., an adenoviral vector, and introduced in a cell (e.g., a fat cell, fibroblast). Cells expressing Prdm16 may then be injected (e.g., subcutaneous or intravenous injection) into the mammal. Expression of Prdm16 in the mammal will induce brown adipocyte differentiation. Increased brown adipose tissue in the mammal will warm up the body and blood of the mammal resulting in an increased metabolic rate for the mammal. An increased metabolic rate will in turn lead to increased energy expenditure and the treatment and/or prevention of obesity and obesity related disorders.

Example 4

Transdifferentiation of Fat Cells

White fat cells may be induced into brown fat cells. For example, PPARγ may be introduced into nude mice to produce fat pads within the nude mice. Cells transfected with a vector comprising a Prdm16 nucleic acid may be cultured and subsequently injected into the fat pads in the nude mice.

Following injection of Prdm16 expressing cells, the fat pads will transdifferentiate into brown fat cells.

Example 5

Transcriptional Control of Brown Fat Determination by PRDM16

Adipose cells and tissue are of great interest in view of the worldwide epidemic of obesity and its associated metabolic disorders, such as insulin resistance, diabetes, dyslipidemia and hypertension. Fat cells occur in two distinct subtypes: white fat cells, that function primarily to store energy in the form of triglycerides, and brown fat cells that oxidize fuels and dissipate energy in the form of heat. Brown adipose tissue (BAT) is important for small mammals such as mice to defend against the cold. In humans, brown fat is abundant at birth, but is rapidly replaced by white adipose tissue (WAT) and is relatively scarce in the adult as an identifiable tissue (Lean and James, 1986). On the other hand, several reports indicate that brown fat cells are interspersed within WAT of rodents and humans (Cousin et al., 1992; Garruti and Ricquier, 1992; Guerra et al., 1998; Lean et al., 1986; Oberkofler et al., 1997; Xue et al., 2007). Identifying the mechanisms that stimulate the development or function of human BAT could, therefore, provide new therapeutic avenues to reduce obesity and its associated diseases.

Brown fat cells are characterized by densely packed mitochondria that contain uncoupling protein-1 (UCP1) in their inner mitochondrial membrane. UCP1, almost exclusive to brown fat cells, is a proton transporter that allows protons to leak across the mitochondrial inner membrane, thereby dissipating the electrochemical gradient normally used for ATP synthesis (reviewed by Klingenberg, 1999). The thermogenic capacity of brown fat cells, in which over 50% of cellular respiration is uncoupled from ATP synthesis, is unique among mammalian cell types (Nedergaard et al., 1977; Prusiner et al., 1968; Reed and Fain, 1968).

Brown fat cells also depend upon an extensive vascular bed and a high degree of sympathetic innervation to produce and distribute heat. Cold, sensed in the CNS, causes sympathetic nerves to release catecholamines which, through the β-adrenergic receptors, increases cyclic-AMP levels in brown fat cells (reviewed by Cannon and Nedergaard, 2004). Cyclic-AMP is a critical second messenger in the function of brown fat, stimulating the levels of key thermogenic factors such as PGC-1α, type 2 deiodinase and UCP1. Chronic adrenergic stimulation can also cause a proliferation of brown adipose preadipocytes and the emergence of pockets of brown fat cells in white fat depots (Bronnikov et al., 1992; Cannon and Nedergaard, 2004; Ghorbani and Himms-Hagen, 1997; Himms-Hagen et al., 2000; Nedergaard et al., 1994).

As noted above, a small number of brown adipocytes and detectable levels of UCP1 mRNA are found in white fat of adult humans (Garruti and Ricquier, 1992; Oberkofler et al., 1997). Indeed, BAT and oxidative activity can be increased by chronic cold exposure in humans (Huttunen et al., 1981). A re-emergence of BAT is also observed in adult humans with pheochromocytoma, where neuroendocrine tumors cause excessive catecholamine secretion (Ricquier et al., 1982). Experiments in rodents have also demonstrated that chronic cold exposure or β3-adrenergic stimulation induces the expression of UCP1 in classic white fat depots (Himms-Hagen et al., 2000). Interestingly, particular mouse strains have more brown adipose cells in their white fat depots, which correlates with a lower susceptibility to obesity and diabetes (Guerra et al., 1998). Moreover, ectopic deposits of BAT in mouse skeletal muscle protect against diet-induced obesity (Almind et al., 2007).

The extent to which BAT functions in the regulation of energy balance has been well studied in rodents. Overfeeding activates BAT thermogenesis through the stimulation of sympathetic nerves (Cannon and Nedergaard, 2004; Lupien et al., 1985; Rothwell and Stock, 1979). Increased UCP1 expression in mouse fat promotes energy expenditure, reduces adiposity and protects animals from diet-induced and genetic forms of obesity (Cederberg et al., 2001; Ghorbani et al., 1997; *Ghorbani and Himms-Hagen,* 1997; Guerra et al., 1998; Kopecky et al., 1995; Kopecky et al., 1996; Tsukiyama-Kohara et al., 2001). Furthermore, specific ablation of brown fat, through expression of a toxigene, leads to reduced whole body energy expenditure and increased obesity (Hamann et al., 1996; Lowell et al., 1993).

The developmental origin of fat, either brown or white, has not been fully elucidated; however, much is known about the process of adipogenic differentiation from preadipocytes. Extensive studies in cultured cell and mouse models have revealed the central role of PPARγ in the differentiation of both brown and white adipose cells (Barak et al., 1999; Kubota et al., 1999; Nedergaard et al., 2005; Rosen et al., 2002; Rosen et al., 1999; Tontonoz et al., 1994). Thus, PPARγ is apparently not the primary determinant of whether a fat cell assumes a brown versus white phenotype. In fact, brown and white preadipocytes appear to be fully "committed" at that stage since fibroblastic cells cultured from brown depots differentiate as brown fat cells whereas those from white fat tissue differentiate as white adipocytes (Klaus, 1997; Klaus et al., 1995; Kozak and Kozak, 1994). The cold-induced emergence of brown adipocytes in WAT, and replacement of BAT with WAT in newborn humans and obese rodents does, however, suggest some degree of plasticity, at least at the tissue level. However, whether mature adipocytes can interconvert, or whether separate pools of white and brown precursors mediate "transdifferentiation" of these tissues has not been resolved.

The influence of brown fat on energy balance has thus motivated strong interest in finding a dominant regulator of brown fat cell determination. To date, a "master" regulator of brown fat has not been found, in terms of a single, tissue-selective factor that can positively regulate the entire program of brown fat in a cell-autonomous manner and which is required for the brown fat cell phenotype. Several transcription-related factors have, however, been shown to influence the brown fat cellular phenotype. Notably, the transcriptional coactivator PGC-1α is highly expressed in brown fat compared to white fat, and can activate the adaptive thermogenic gene program when expressed in white fat cells (Puigserver et al., 1998; Tiraby et al., 2003). However, genetic experiments in cultured brown fat cells and mice have clearly indicated that PGC-1α, while critical for cAMP-dependent thermogenic aspects of the brown fat program, does not give cells their essential brown fat identity (Lin et al., 2004; Uldry et al., 2006).

In addition to PGC-1α, other factors have been shown to selectively influence the function of brown versus white fat. FOXC2, when expressed by transgenesis in WAT, induces many features of BAT tissue (Cederberg et al., 2001). However, FOXC2 is not expressed preferentially in BAT versus WAT, and its role in this interconversion between tissues is probably linked to its stimulation of adrenergic signaling when FOXC2 is overexpressed in vivo (Dahle et al., 2002; Gronning et al., 2006). A cell-autonomous role for FOXC2 in white to brown fat cell conversion has not been shown. Other factors, such as Rb (retinoblastoma), p107 and RIP140 have been shown to suppress the brown fat phenotype in white fat cells or tissue (Christian et al., 2005; Hansen et al., 2004; Leonardsson et al., 2004; Powelka et al., 2006; Scime et al., 2005). Quantitative increases in the levels of Rb, p107 or RIP140 have not, however, been demonstrated to preferentially favor the differentiation of white fat adipocytes. These data suggest that while each of these factors may participate, to various degrees, in the formation or function of brown fat cells, they are unlikely to be the central factor that determines an adipocyte to specifically commit to a brown adipose fate.

Using global expression analysis of murine transcriptional components, a very small number of factors that are selectively expressed in brown versus white fat cells were found. One of these was PRDM16, a 140 kD PR-(PRD1-BF-1-RIZ1 homologous) domain containing protein, that was first identified at a chromosomal breakpoint in myeloid leukemia (Nishikata et al., 2003). The results herein show that PRDM16 activates a broad program of brown fat differentiation when expressed in cultured white fat preadipocytes or in white fat depots in vivo. Uncoupled respiration accounts for the majority of the very high oxygen consumption of PRDM16-expressing cells, a classic hallmark of brown fat. Furthermore, shRNA-mediated knock-down of PRDM16 in bona fide brown fat preadipocytes allows normal differentiation to fat cells but results in a total loss of the brown fat character. These experiments reveal a dominant regulatory function for PRDM16 in the brown fat lineage.

Materials and Methods

Plasmids and Viral Vectors

Full-length coding sequence of mouse PRDM16 (GeneID: 70673) was amplified from brown fat RNA by PCR, and cloned into the Xho1/EcoR1 sites of pMSCV-puro retroviral vector (Stratagene) in frame with an N-terminal FLAG tag. PRDM16 cDNA was also cloned into the Xho1/EcoR1 sites of pcDNA3.1 (Invitrogen) for expression in mammalian cells. DNA-binding mutants of PRDM16, including the R998Q allele, were created by site-directed mutagenesis (Quickchange, Stratagene). Adenoviral vectors for PRDM16 expression were made in pAdTrack-CMV using the AdEasy system as described elsewhere (He et al., 1998). Adenoviral vectors for PGC-1α and GFP (Yoon et al., 2001); Gal4 fusion plasmids containing PGC-1β (Lin et al., 2002), PGC-1α and SRC-1 (Puigserver et al., 1999) have been described previously. The siRNA sequence identified for use in PRDM16-depletion experiments was: 5'-GAAGAGCGUGAGUA-CAAAU-3' (Dharmacon). The corresponding double-stranded DNA sequence was ligated into pSUPER-Retro (GFP-Neo) (Oligoengine) for retroviral shRNA expression. This siRNA sequence was able to specifically knockdown PRDM16 protein and mRNA expression by over 75%.

Cell Culture

3T3-L1, C3H-10T1/2 and cos7 cells were obtained from ATCC. Immortalized brown fat preadipocytes and PPARγ−/− fibroblasts have been described by others (Rosen et al., 2002; Uldry et al., 2006). 3T3-F442A cells were from H. Green (Green and Kehinde, 1979). Primary brown fat preadipocytes were obtained from mice by collagenase digestion as described elsewhere (Tseng et al., 2004). Primary white fat stromal vascular and mature fat cells were fractionated according to published methods (Rodbell, 1964; Soukas et al., 2001). For retrovirus production, ϕnx packaging cells (Kinsella and Nolan, 1996) were transfected at 70% confluence by Calcium Phosphate co-precipitation with 10 µg retroviral vectors; viral supernatant was harvested 48 hours later. For retroviral transduction, cells were incubated overnight with viral supernatant supplemented with 8 µg/mL polybrene. For adenoviral infection of mature adipocytes, the fat cell fraction (see above) from epididymal WAT of 10-12 week old C57B16 mice (N=4) was incubated with PRDM16 (GFP) or GFP-expressing adenovirus (M.O.I=100) in 0.5 mL eppendorf tubes for 2 hours in 10% FBS/DMEM. The medium was then replaced, and cells were maintained at 5% $CO_2$, 37° C. for an additional 48 hours prior to RNA extraction and expression analysis. GFP expressed from the adenoviral vectors was used to monitor infection efficiency, which was typically over 50%.

Adipocyte differentiation was induced by treating confluent cells for 48 hours in medium containing 10% FBS, 0.5 mM isobutylmethylxanthine, 125 nM indomethacin, 1 µM dexamethosone, 850 nM insulin, 1 nM $T_3$ and 1 µM rosiglitazone (Cayman Chemical). Two days after induction, cells were switched to maintenance medium containing 10% FBS, 850 nM insulin, 1 nM $T_3$ and 1 µM rosiglitazone. To stimulate thermogenesis, cells were incubated with 0.5 mM dibutyrl cyclic-AMP for 4 hours. All chemicals for cell culture were obtained from Sigma, unless otherwise indicated.

Global Expression Screen of Transcription-Related Factors

RNA was isolated from brown adipose tissue (BAT) and epididymal white fat tissue (WAT) of 5 adult male C57B16 mice at 10-12 weeks of age. First strand cDNA was prepared from RNA samples using oligo-d(T) and Superscript III (Invitrogen). cDNAs were normalized for equal loading by real-time PCR using TBP and HPRT mRNA expression levels. 30 cycles of PCR (94° C.-30 sec, 62° C.-45 sec, 68° C.-45 sec) with primer-sets described in (Gray et al., 2004) were performed in 50 µl reactions using Platinum Taq (Invitrogen). PCR products (average of 500 bp) were separated on 96 well-2% agarose E-gels (Invitrogen) containing ethidium bromide, imaged, and analyzed using E-Editor software (Invitrogen).

Reporter Gene Assays

Reporter gene assays were performed in cos7 cell or brown fat preadipocytes. Briefly, the −2 kb-PGC-1α reporter gene (Handschin et al., 2003) or the UCP1-4 kb reporter (a gift from L. Kozak) were transiently transfected with PRDM16 and/or PGC-1α expression plasmids in 12 well plates using Fugene6 (Roche). Forty-eight hours after transfection, cells were harvested and reporter gene activity was measured using the Dual-luciferase Reporter Assay System (Promega). Forskolin (100 µM) or differentiation cocktail was added for 4 or 24 hours prior to harvesting cells, respectively. Gal4 based reporter gene assays were performed in cos7 cells by co-transfecting Gal4-DBD or Gal4-DBD fusion constructs with PRDM16 or control expression constructs. Firefly luciferase reporter gene measurements were normalized using *Renilla* luciferase activity.

Binding Studies and Electrophoretic Mobility Shift Assays (EMSA)

To study protein-protein interactions, brown fat preadipocytes were transduced with retroviral-PRDM16 or control vector, and induced to differentiate into adipocytes. At day 6 of differentiation, whole cell extracts were incubated with flag-M2 agarose (Sigma) overnight at 4° C. Immunoprecipitates were washed three times with washing buffer (20 mM Tris HCl, 150 mM NaCl, 10% glycerol, 2 mM EDTA, 0.1% NP40, 0.1 mM PMSF), resolved by SDS-PAGE, transferred to PVDF membrane (Millipore) and blotted with anti-PGC-1α (Puigserver et al., 1999) and PGC-1β (Lin et al., 2005) antibodies. For GST-immunoaffinity assays, GST-PGC-1α fusion proteins immobilized to glutathione sepharose beads were purified as previously described (Wallberg et al., 2003). $^{35}$S-labeled PRDM16 or ERRα proteins were in vitro translated using TNT coupled transcription-translation system (Promega). To examine the binding of PGC-1α with the R998Q mutant allele of PRDM16, cos7 cells were co-transfected with HA-PGC-1α and Flag-PRDM16 (wt and R998Q). Whole cell extracts were immunoprecipitated with HA antibody (Roche), resolved by SDS-PAGE and blotted with anti-Flag antibody to detect PRDM16. For EMSA, an oligonucleotide probe containing the PRDM16 binding site (5'-GATCCGACAAGATAAGATAAGGATC-TATAAGAAGATGAGGTATG-3') (Nishikata et al., 2003) was end-labeled with $\gamma^{32}$P-ATP and incubated (5 fmol) with in vitro translated wildtype and R998Q mutant PRDM16 in binding buffer (10 mM Tris-HCl (pH 7.5), 50 mM NaCl, 1 mM MgCl2, 0.5 mM EDTA, 4% glycerol, 0.5 mM DTT, and 0.5 mg poly(dI-dC)-poly(dI-dC)). 50 or 500 fmol of unlabeled probe was added to the binding reaction for competition assays. DNA-protein complexes were separated by electrophoresis on a 4% PAGE gel then dried and exposed to X-ray film.

Oxygen Consumption Assays

PPARγ$^{-/-}$ fibroblasts transduced with retroviral-PPARγ2 and either PRDM16 or vector control were grown to confluence and induced to differentiate into adipocytes. At day 6 of differentiation, oxygen consumption was measured in fat cells as described previously (St-Pierre et al., 2003). For cyclic-AMP-induced respiration assays, fully differentiated fat cells were incubated with 0.5 mM dibutyrl cyclic-AMP for 12 hours before measuring oxygen consumption.

Electron Microscopy

Electron microscopy was performed as described previously (St-Pierre et al., 2003) on PPARγ$^{-/-}$ cells expressing PPARγ2 and PRDM16 or vector control before and after their differentiation into adipocytes (day 6). To calculate the mitochondrial volume density, a grid was laid on randomly selected micrographs (n>20), and the number of points falling onto mitochondria was expressed as a fraction of those landing on cell area.

Real-Time PCR Analysis and Western Blotting

Total RNA from cultured cells was isolated using Qiagen Rneasy mini columns according to manufacturer's instruction. Tissue RNA samples were prepared by the Trizol method (Invitrogen). Northern blot analysis was performed as described before (Maniatis et al., 1982). For real-time PCR analysis, RNA was reverse transcribed using the IScript cDNA synthesis kit (BioRad), and used in quantitative PCR reactions containing SYBR-green fluorescent dye (ABI). Relative expression of mRNAs was determined after normalization with TBP levels using the $^{\Delta\Delta}$-Ct method. Q-PCR was performed using the ABI-9300 PCR machine. As a point of reference, the Ct values for both PRDM16 and TBP mRNA expression in BAT were typically 24-26. Student's t-test was used for comparisons and to obtain statistics. Primers used for real-time PCR are shown in Table 2. For western blot analysis, cells or tissues were lysed in RIPA buffer (0.5% NP-40, 0.1% sodium deoxycholate, 150 mM NaCl, 50 mM Tris-Cl, pH 7.5). Lysates were resolved by SDS-PAGE, transferred to PVDF membrane (Millipore) and probed with anti-UCP1 (Chemicon), anti-Flag M2 (Sigma), anti-PRDM16 (rabbit polyclonal), and anti-pol-II (Santa-Cruz biotechnology).

Animals

All animal experiments were performed according to procedures approved by the Dana-Farber Cancer Institute's Institutional Animal Care and Use Committee. Mice were maintained on a standard rodent chow diet with 12 hr light and dark cycles. For acute cold-exposure studies, BAT was obtained from five 3-4 week old male C57Black6 mice that were housed at 4° C. for 4 hours. For transgenic mice, the complete PRDM16 cDNA was cloned 3' to the 5.4 kb aP2 promoter/enhancer and the human growth hormone polyadenylation site was inserted 3' to the cDNA. FVB Mouse oocytes were injected with this construct by the Dana-Farber Cancer Institute Core Facility. CL316, 243 (Sigma) at 0.5 mg/kg was injected intraperitoneally into mice daily for 6 days. Mice were euthanized for analysis of tissues 4 hours following the final injection on day 6. Transgenic and non-transgenic control littermates used for all experiments were 4-6 month old males. For cell transplantation, $10^7$ fibroblasts, transduced with retroviral-PPARγ2 and either PRDM16 or vector control, were suspended in 200 ml of 10% FBS/DMEM and implanted subcutaneously just above the sternum of nude (Nu/Nu) mice (Taconic) (N=10 mice/stable cell line) using an insulin syringe attached to a 28 gauge needle. This injection site was chosen due to the almost complete absence of endogenous subcutaneous fat. For Immunohistochemistry, paraffin-embedded sections were incubated with anti-cidea (Chemicon) or anti-UCP1 (Abcam) antibodies for 30 min at room temperature, followed by detection using the ABC Vectastain-Elite kit (Vector Labs) according to manufacturer's instructions.

Transcriptional Profiling

Total RNA was isolated from the epididymal WAT and interscapular BAT of 3 male C57B16 mice at 10-12 weeks of age. Array hybridization and scanning were performed by the Core Facility at Dana-Farber Cancer Institute using Affymetrix mouse 430 high-density oligonucleotide arrays according to established methods (Lockhart et al., 1996). The array data were normalized using the DNA-Chip Analyzer (dChip) software (Li and Wong, 2001). The statistical significance of differences in gene expression was assessed by unpaired t test ($p<0.05$). The microarray data set has been deposited in the Gene Expression Omnibus repository, accession no. GSE8044.

PRDM16 is Expressed Selectively in Brown Adipocytes

With the goal of identifying transcriptional components that regulate the development and function of brown adipocytes, a global expression screen of all genes known to be involved in transcription and those having a molecular signature suggestive of transcriptional function was performed. White and brown fat tissue RNA samples from C57B16 mice (n=5) at 10-12 weeks of age were examined by RT-PCR using primer-sets corresponding to all transcription-related mouse genes (Gray et al., 2004). Genes differentially regulated in these tissues were then assayed for their expression in cultured white and brown fat cells from established cell lines. Three genes, Lhx8, Zic1 and PRDM16 ultimately met the criteria of being preferentially expressed in brown versus white fat and having elevated (>5 fold) mRNA expression levels in immortalized brown fat cells (Uldry et al., 2006) compared to any of three immortalized white fat cell lines (3T3-L1, 3T3-F442A, C3H10T1/2). As described in detail below, ectopic expression demonstrated a function for PRDM16 in stimulating the brown fat phenotype.

Figure 16:
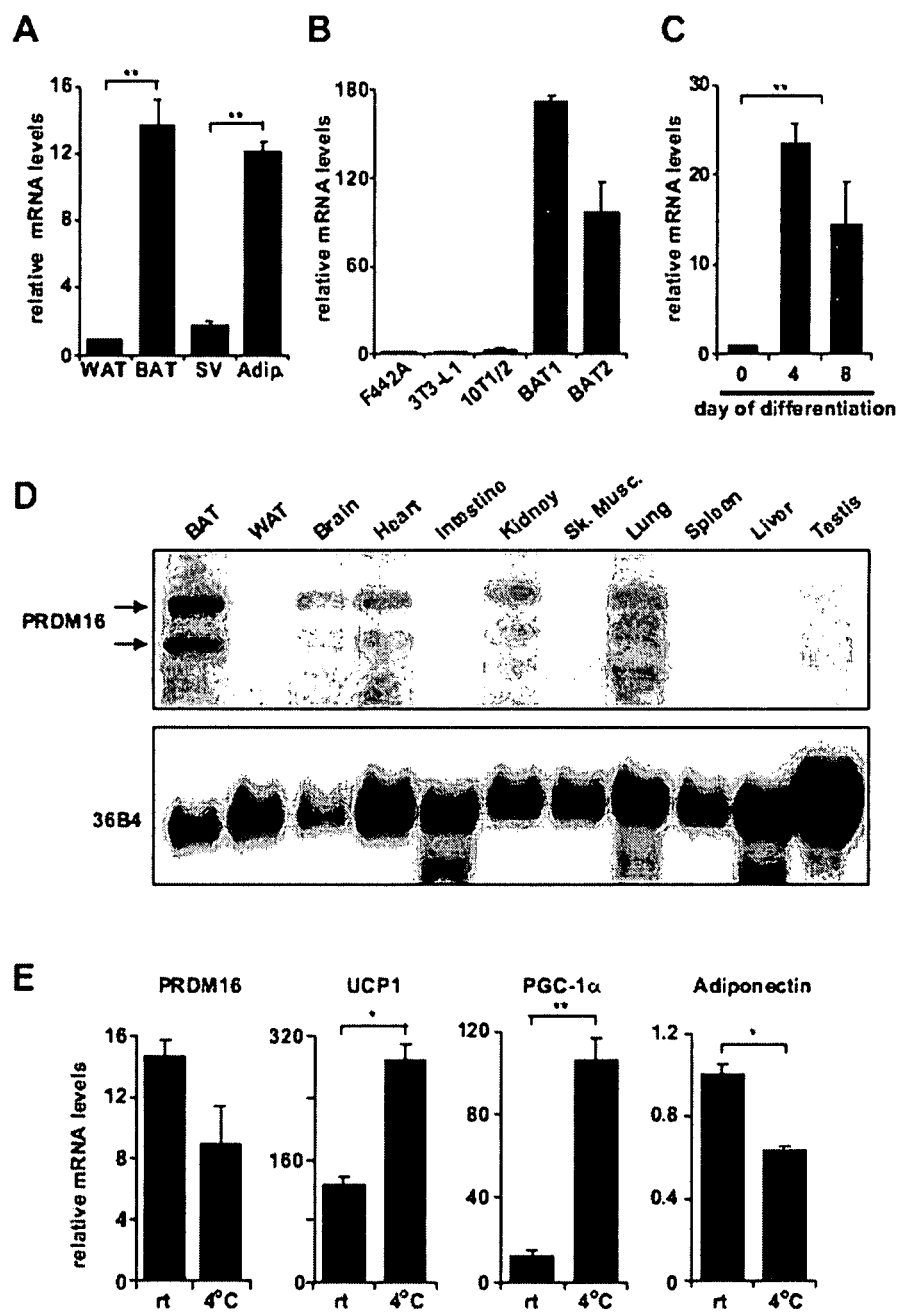
FIG. 16 shows that PRDM16 is expressed selectively in brown fat cells. (A) shows real-time PCR analysis of PRDM16 mRNA expression in BAT relative to WAT; and its expression in the adipocyte fraction (Adip.) compared to the stromal vascular fraction (SV) of BAT (n=6, mean±SD). (B) shows PRDM16 mRNA expression in adipocytes from immortalized BAT cell lines (BAT1 and BAT2) and three WAT cell lines (3T3-F442A, 3T3-L1, C3H-10T1/2) (n=3-5 samples per cell line, mean±SD). (C) shows PRDM16 mRNA levels during the differentiation of immortalized BAT cell lines (n=3 for each of 2 separate cell lines, mean±SD). (D) shows Northern blot analysis of PRDM16 mRNA and control, 36B4 mRNA, in adult mouse tissues. (E) shows expression of PRDM16, UCP1, PGC-1α and adiponectin in BAT after a 4° C. cold exposure of mice for 4 hours (n=5 mice per group, mean±SD) (rt: room temperature) (* $p<0.05$; ** $p<0.01$).

Quantitative analyses of PRDM16 expression at the mRNA level showed a 15-fold enrichment in brown (BAT) relative to white fat tissue (WAT) (n=6) (FIG. 16A). Fractionation of BAT showed that PRDM16 was mainly expressed in mature brown adipocytes as compared to stromal-vascular fraction that contains preadipocytes and other cell types (FIG. 16A). Importantly, PRDM16 was selectively expressed in adipocytes from two immortalized brown fat cell lines (Uldry et al., 2006) as compared to its expression in white fat cells from 3T3-F442A, 3T3-L1 and C3H-10T1/2 fibroblasts (FIG. 16B). Moreover, PRDM16 mRNA expression increased 20-fold during the differentiation of brown fat cells in culture (FIG. 16C). Northern blot analysis indicated that PRDM16 was expressed at its highest levels in BAT and was virtually undetectable in WAT (FIG. 16D). PRDM16 transcripts were also detected in heart, lung, kidney and brain. Acute cold-exposure of mice (4° C. for 4 hours) activated the thermogenic program of BAT without any significant regulation of PRDM16 mRNA expression (p=0.13) (FIG. 16E). Similarly, PRDM16 expression was not affected by cAMP treatment of cultured cells. These results suggest that PRDM16 expression in brown fat is linked to determination or differentiation but not to adaptive thermogenesis. Collectively, these data identify PRDM16 as a gene that is very selectively expressed in brown versus white adipocytes.

PRDM16 Drives the Molecular Phenotype of Brown Fat Cells

Figure 17:
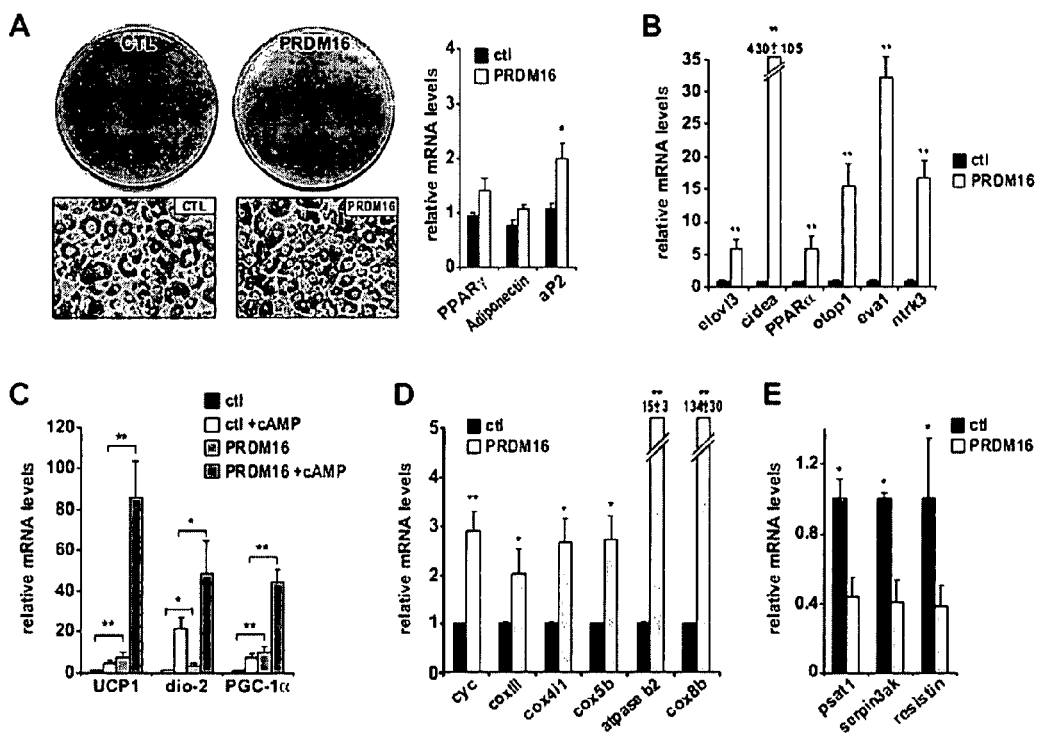
FIG. 17 shows that PRDM16 expression induces the gene program of brown fat cells. (A) shows Oil-red-0 staining of mature adipocytes (day 6) from PPARγ-deficient cells expressing retroviral PPARγ2 and either retroviral-PRDM16 or vector control (ctl). These adipocyte cultures were analyzed by real-time PCR for their expression of: differentiation markers common to WAT and BAT (A); brown fat cell-selective genes (B); brown fat-thermogenic genes (UCP1, deiodinase-d2 (dio-2), PGC-1α) with and without cAMP treatment (C); mitochondrial components (D); and white fat cell-selective markers (psat1, serpin3ak, resistin) (E). (n=3, mean±SD) (* $p<0.05$; ** $p<0.01$).

To study its role in brown fat cells, PRDM16 was expressed in cells with no preadipose (white or brown) character whatsoever, using fibroblasts genetically deficient in PPARγ (Rosen et al., 2002). A retroviral vector expressing PRDM16 or control vector was introduced together with a PPARγ2-expressing retroviral vector into subconfluent fibroblasts and selected for stable viral integration. Cells transduced with retroviral-PRDM16 expressed mRNA levels which were 4 to 6-fold higher than its endogenous expression in cultured brown fat cells. These cell cultures were grown to confluence and stimulated to undergo adipogenic differentiation driven by the ectopic PPARγ2. At day 6 of differentiation, cultures expressing PPARγ2 were composed mainly of adipocytes whether or not they also expressed PRDM16; ectopic PRDM16 did not appear to promote nor inhibit cellular differentiation per se (FIG. 17A). At the molecular level, expression of genes common to both white and brown fat lineages were either not affected (PPARγ and adiponectin) or moderately elevated (aP2) by PRDM16 expression (FIG. 17A).

To analyze the molecular phenotype of mature fat cells from PRDM16-expressing cultures in detail, global, unbiased expression analyses were performed to develop a more complete set of brown versus white fat-selective genes. To this end, brown and white fat tissues from three adult C57B16 mice were expression profiled using Affymetrix microarrays. The mRNA levels for the 40-most highly enriched genes in both brown and white fat tissue were analyzed by Q-PCR in samples from three independent mice to validate the microarray data. These genes were then assayed for their expression in mature fat cells from three white (3T3-L1, 3T3-F442A, C3H10T1/2) and two brown fat cell lines. Altogether, 19 BAT-selective and 9 WAT-selective genes were identified whose expression correlated completely with the BAT or WAT-adipocyte phenotype in tissue and in cultured cells (by all pair wise comparisons) (Table 1).

Strikingly, most brown fat selective mRNAs were specifically induced in adipocytes from PRDM16-expressing cells. For example, elovl3 (previously called cig30), a very long chain fatty acid elongase that is expressed in brown but not white fat and is implicated in brown fat hyperplasia (Tvrdik et al., 1997; Westerberg et al., 2006), was induced 6-fold by PRDM16 expression (FIG. 17B). Cidea, a gene predominantly expressed in brown fat where it is thought to regulate UCP1 activity (Zhou et al., 2003), was induced 430-fold by PRDM16 (FIG. 17B). PRDM16 also elevated PPARα expression, a brown fat selective gene and an important regulator of fatty acid oxidation (Barbera et al., 2001; Braissant et al., 1996), by 5-fold (FIG. 17B). In addition, several genes, not previously known to be expressed selectively in brown versus white adipocytes, such as otopetrin1 (otop1), epithelial like antigen-1 (eva1) and neurotrophic tyrosine kinase receptor type 3 (ntrk3) were significantly increased by PRDM16-expression (FIG. 17B). Moreover, PRDM16-transduced cells expressed several of the important thermogenic genes in a cAMP-dependent manner, similar to what bona fide brown fat cells do in culture and in vivo. The mRNA levels of UCP1, deiodinase-d2 and PGC-1α were increased by PRDM16 in unstimulated fat cells and induced to very high levels by PRDM16 in response to cAMP (FIG. 17C). UCP1, for instance, was elevated 20-fold by cAMP in PRDM16-expressing cells, compared to only a 3-fold increase in control cells. PRDM16 expression also elevated the mRNA levels for many genes of mitochondrial oxidative phosphorylation, that are known to be enriched in brown fat cells and tissue, such as cytochrome c (cyc), cox4 μl, and cox5b (FIG. 17D). In particular, cox8b, a highly brown fat-selective mitochondrial gene (see Table 1) was expressed at 134-fold higher levels in PRDM16-compared to control-adipocyte cultures.

Figure 18:
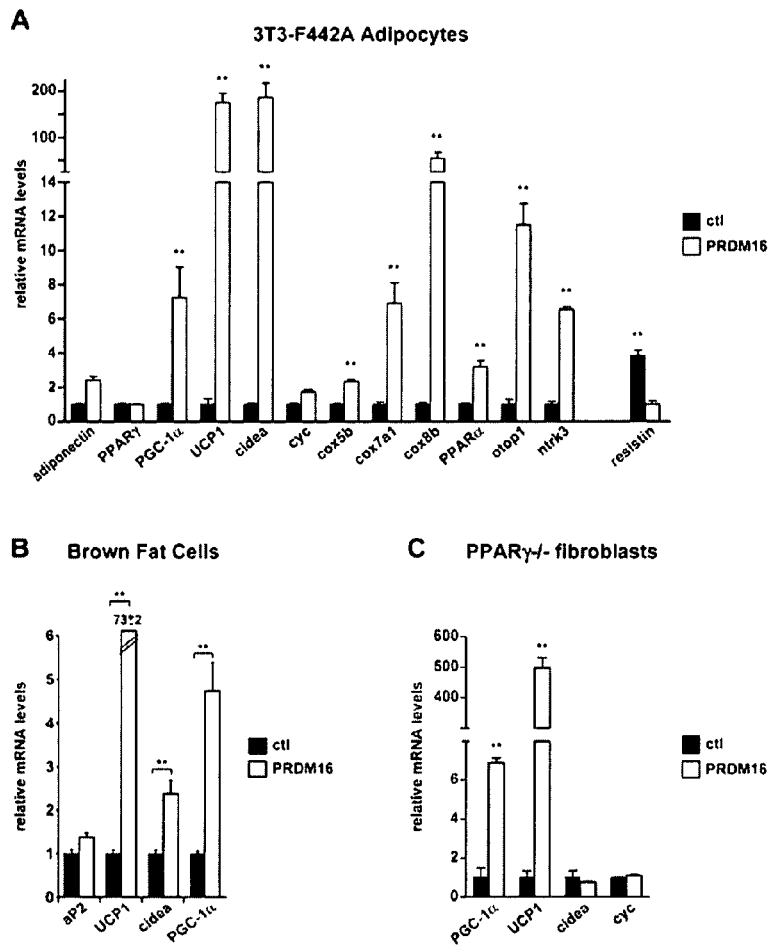
FIG. 18 shows that PRDM16 activates BAT genes in other fat cellular systems. Figure (A) shows real-time PCR analysis of gene expression in adipocytes (day 6) from 3T3-F442A preadipocytes expressing retroviral-PRDM16 or -vector control (ctl). (B) shows real-time PCR analysis of fat-related gene expression in adipocytes (day 4) from brown fat preadipocytes expressing retroviral-PRDM16 or -vector control (ctl). (C) shows real-time PCR analysis of gene expression in PPARγ-deficient fibroblasts expressing retroviral-PRDM16 or -vector control (ctl) that had been treated with the adipogenic differentiation protocol. (n=3, mean±SD) (* $p<0.05$; ** $p<0.01$).

The mRNA levels of several genes that are preferentially expressed in white relative to brown fat cells were significantly repressed by PRDM16 expression, including psat1, serpin3ak and resistin (FIG. 17E). In particular, resistin, a WAT-secreted protein in mice that promotes insulin resistance (Steppan et al., 2001), was reduced by 60% at the mRNA level as a result of PRDM16 expression. Altogether, 20/28 or 71% of the brown/white fat cell selective genes that were identified in an unbiased global expression analysis were regulated in a brown fat-specific manner by PRDM16 (Table 1). A robust regulation of brown fat cell genes by PRDM16 was observed in other cellular models including 3T3-F442A white preadipocytes and immortalized brown preadipocytes (FIG. 18A and FIG. 18B). In particular, PRDM16 increased the mRNA levels of UCP1 and cidea by almost 200-fold and repressed resistin expression by 70% in 3T3-F442A adipocytes (FIG. 18A). These data, therefore, demonstrate that the action of PRDM16 in activating brown fat gene expression was not unique to PPARγ$^{-/-}$ fibroblasts and also not dependent on exogenous PPARγ expression. Moreover, PRDM16 dramatically induced the expression of key brown fat genes UCP1 and PGC-1α, but not cidea or mitochondrial components in the genetic absence of PPARγ (FIG. 18C). These results show that certain genes characteristic of the brown fat gene program do not absolutely require the fat cell environment and/or PPARγ function. Altogether, these data thus strongly suggest a role for PRDM16 as a positive regulator of the brown fat cell gene program.

Figure 19:
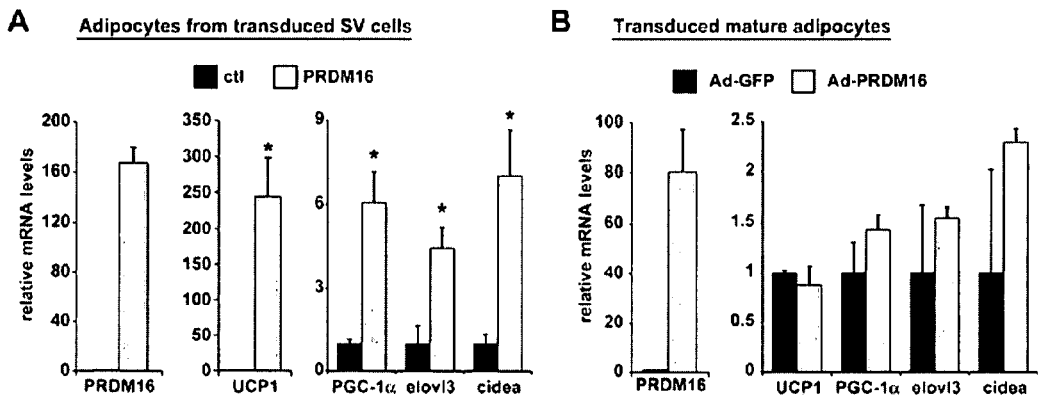
FIG. 19 shows that PRDM16 function is required before or during adipocyte differentiation. (A) and (B) show real-time PCR analysis of the expression of brown fat cell-selective genes in adipocytes from PRDM16- or ctl-transduced stromal-vascular cells isolated from mouse white fat (A); and in mature fat cells from the same tissue transduced with adenoviral-PRDM16 or -GFP control (B). (n=3, mean±SD) (* $p<0.05$; ** $p<0.01$).

An important question is whether PRDM16 can stimulate the transdifferentiation of mature white fat cells into brown fat. This question was addressed by analyzing the effect of PRDM16 expression in stromal-vascular cells and mature adipocytes from the same white fat tissue. When PRDM16 was expressed in stromal-vascular cells prior to differentiation, this factor efficiently activated the brown fat gene program in differentiated cultures, including an induction of UCP1 mRNA by more than 200-fold (FIG. 19A). However, expression of PRDM16 using adenovirus in mature white fat cells failed to elicit a significant induction of brown fat marker genes, despite robust expression of PRDM16 (FIG. 19B). Importantly, PRDM16 protein expressed by adenovirus was able to induce BAT-related genes when introduced into cells before their differentiation. Altogether, the strong induction of brown fat genes in adipocytes from PRDM16-expressing primary stromal vascular cells, and lack of any effect in mature cells from the same tissue strongly suggests that PRDM16 function is required before and/or during adipogenic differentiation to promote brown fat cell character.

Figure 20:
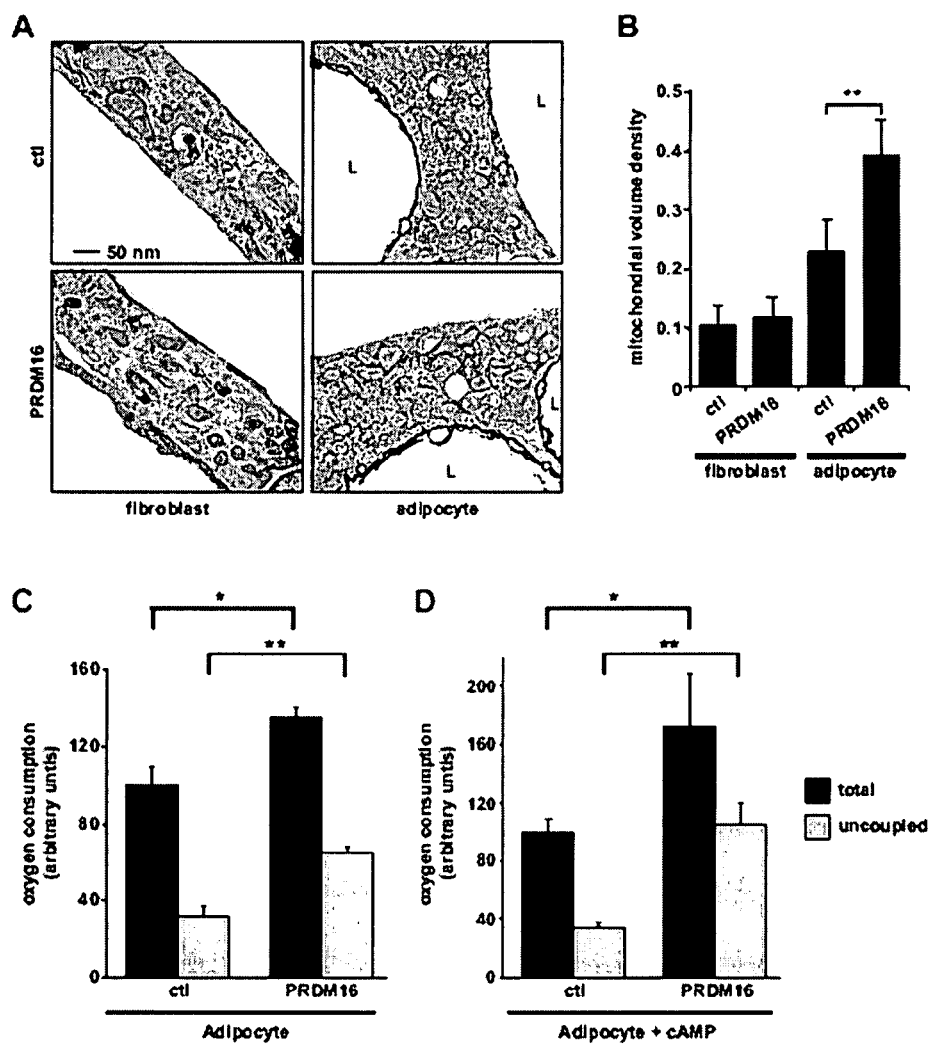
FIG. 20 shows that PRDM16 stimulates mitochondrial biogenesis and uncoupled respiration. (A) shows representative transmission electron micrographs of fibroblasts and mature adipocytes (day 6) from PPARγ-deficient cells expressing retroviral PPARγ2 and either retroviral-PRDM16 or vector control (ctl). (B) shows a comparison of mitochondrial volume densities from cells depicted in Figure (A) (n=>20 micrographs per group, mean±SD). Figure (C) and (D) show total mitochondrial oxygen consumption and uncoupled respiration in mature adipocytes expressing either PRDM16 or control vector under basal conditions (n=4, mean±SD) (C), or after stimulation with a cAMP analog for 12 hours (n=4, mean±SD) (D). (L: lipid droplet) (* $p<0.05$; ** $p<0.01$).

PRDM16 Stimulates Mitochondrial Biogenesis and Uncoupled Cellular Respiration A defining feature of brown fat cells is their very abundant mitochondria and associated high rates of cellular respiration, particularly uncoupled respiration. To assay the functional consequences of PRDM16 action in fat cells, PPARγ$^{-/-}$ cells transduced with PRDM16 or vector control, together with PPARγ2, were induced to differentiate into adipocytes. Representative electron micrographs of control and PRDM16 expressing cells before and after adipogenic differentiation showed a very significant elevation of mitochondrial density by PRDM16 only in differentiated fat cells (FIG. 20A). Quantitative analysis of this data revealed a 2-fold increased mitochondrial volume in PRDM16-expressing adipocytes compared to control cultures ($p<0.001$) (FIG. 20B). Oxygen consumption was measured in adipocytes using an oxygen sensitive electrode to calculate relative rates of respiration. These experiments revealed a remarkable effect of PRDM16 on the levels of both total and uncoupled cellular respiration. Specifically, adipocytes from PRDM16-expressing cells displayed a 40% increase in total respiration and 2-fold increase in uncoupled respiration relative to control cultures ($n=4$) (FIG. 20C). After 12 hour treatment with cAMP, PRDM16-expressing adipocytes displayed a 70% increase in total respiration relative to control cells and >60% of their respiration was uncoupled from ATP production (FIG. 20D). PRDM16 expression, therefore, induced mitochondrial biogenesis and uncoupled respiration to levels that are characteristic of brown fat cells (Uldry et al., 2006) but not other mammalian cell types. These results demonstrate that PRDM16 expression enables fat cells to develop the respiratory activity characteristic of brown adipocytes.

In Vivo Differentiation of PRDM16-Expressing Fibroblasts into "Brown" Fat

Figure 21:
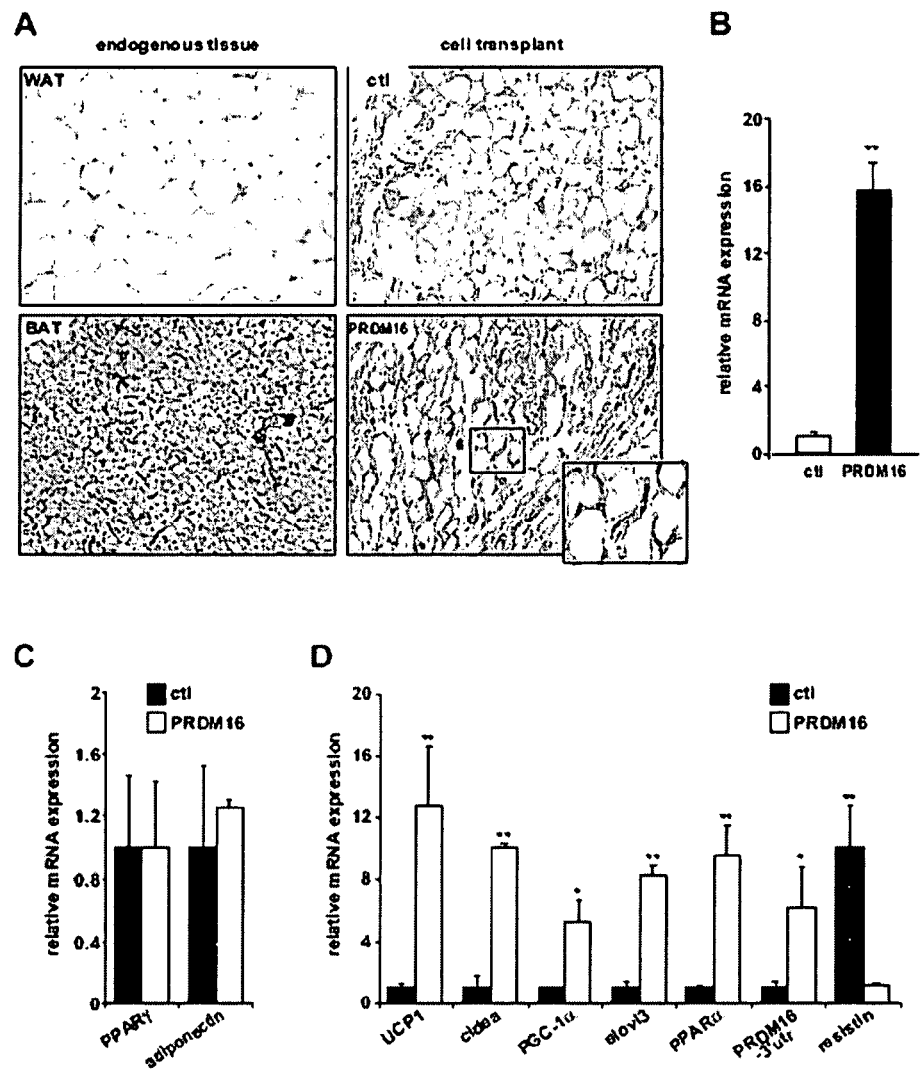
FIG. 21 shows the differentiation of PRDM16-expressing cells into brown fat in vivo. (A) shows immunohistochemistry for cidea protein expression in endogenous WAT and BAT, and in ectopic subcutaneous fat pads formed from fibroblasts expressing PPARγ2 and either vector control (ctl) or PRDM16. (B)-(D) show the results of ectopic fat pads 8-weeks after transplantation that were analyzed by real-time PCR for expression of: PRDM16 (B); differentiation markers common to white and brown fat (PPARγ and adiponectin) (C); brown fat-selective genes (UCP1, cidea, PGC-1α, elovl3, PPAR-α, endogenous PRDM16 (-3'UTR) and the white fat selective marker, resistin (D). (n=10 mice per cell line, mean±SE) (* $p<0.05$; ** $p<0.01$).

Since the environmental cues that stimulate adipocyte differentiation in cell culture and in vivo are presumably different, a more physiological setting was sought to study PRDM16 action. To this end, transplantation studies in mice were utilized. Specifically, $10^7$ PPARγ$^{-/-}$ fibroblasts, expressing PPARγ2 and PRDM16 or PPARγ2 alone, were implanted subcutaneously into nude mice. As shown originally by Howard Green and colleagues (Green and Kehinde, 1979), implanted fibroblasts were able to differentiate into fat tissue. PRDM16 and vector-expressing cells formed equivalent sized ectopic fat pads after 6-8 weeks. Histological analysis showed no obvious differences in the morphology and appearance of the tissues derived from control or PRDM16 expressing cells with both fat pads containing largely unilocular adipocytes (FIG. 21A). Importantly, fat pads from PRDM16-expressing cells displayed an average 16-fold increase in PRDM16 mRNA compared to control fat pads (FIG. 21B), well matched to the ~14 fold enrichment in brown relative to white fat tissue (FIG. 16A). Immunohistochemical analysis showed that only fat tissue from PRDM16-expressing cells and endogenous BAT contained easily detectable levels of the brown fat-specific cidea protein (FIG. 21A). PRDM16 did not influence the tissue expression of general adipogenic markers PPARγ, or adiponectin (FIG. 21C). However, the brown-selective genes UCP1, cidea, PGC-1α, elovl3 and PPARα were all induced by at least 5-fold in fat pads from PRDM16 transduced cells relative to control fat pads (FIG. 21D). PRDM16 also induced the expression of the endogenous PRDM16 gene (PRDM16-3'UTR) suggesting that PRDM16 regulates itself in a positive feed-back loop (FIG. 21D). The mRNA levels of resistin, a white fat selective gene, were reduced by 90% in PRDM16 relative to control-expressing tissue (FIG. 21D). These data demonstrate that a physiological level of PRDM16 expression induces the gene expression program but not the multilocular appearance of BAT. This is as expected, since the morphology of BAT is not cell autonomous and depends on a high degree of sympathetic innervation (Minokoshi et al., 1986; Rothwell and Stock, 1984), which presumably could not take place during the time frame of these experiments.

PRDM16 Functions as a Coregulator to Activate PGC-1α and PGC-1β

Figure 22:
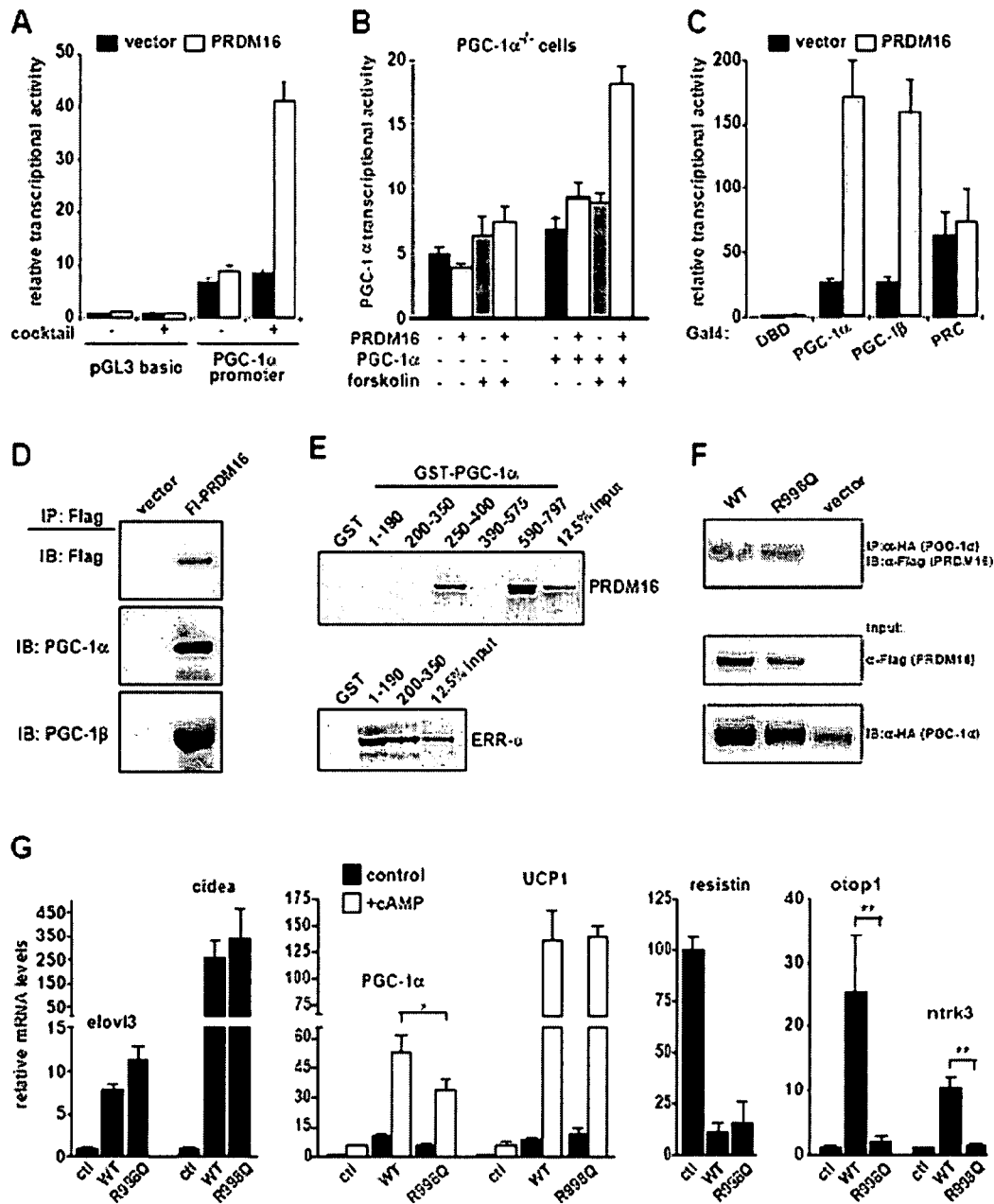
FIG. 22 shows that PRDM16 activates PGC-1α and PGC-1β via direct binding. (A) shows the transcriptional activity of the −2 kb region of PGC-1α in response to PRDM16 or vector control expression in brown fat preadipocytes (n=3, mean±SD). (B) shows PGC-1α promoter activity in response to PRDM16 or vector expression in PGC-1α-deficient cells (n=3, mean±SD). (C) shows the transcriptional activity of Gal4-DNA binding domain (DBD) fusion proteins containing PGC-1α, PGC-1β, or PRC in response to PRDM16 or vector expression (n=3, mean±SD). (D) shows Flag-PRDM16 and its associated proteins were immunoprecipitated from brown fat preadipocytes and analyzed by Western blot to detect PGC-1α and PGC-1β. (E) shows that GST fusion proteins containing different regions of PGC-1α were incubated with $^{35}$S-labeled PRDM16 protein. ERR-α was used to demonstrate binding to the 1-190 and 200-350 regions of PGC-1α. (F) shows that PGC-1α and PRDM16 were co-precipitated from cos7 cells that had been transfected with HA-PGC-1α and either wildtype (WT) or R998Q mutant PRDM16. The input was 2% of the cell lysate used for immunoprecipitation. (G) shows that WT or R998Q mutant PRDM16 were expressed with PPARγ2 in PPARγ$^{-/-}$ fibroblasts. After differentiation into adipocytes (day 6), real-time PCR was used to measure the mRNA expression of: brown fat-selective genes; and resistin, a white fat selective gene (n=3, mean±SD) (* $p<0.05$; ** $p<0.01$).

Since PGC-1α has a prominent role as a regulator of brown fat thermogenic function and its mRNA is induced by the action of PRDM16, PRDM16 function on this gene promoter was studied. The expression of PRDM16 enhanced the activity of the −2 kb PGC-1α promoter, but only in the presence of differentiation-inducing cocktail (FIG. 22A). Additional experiments showed that activation of the PGC-1α promoter by PRDM16 required a cAMP stimulus, either by adding IBMX or forskolin. PRDM16 similarly activated the −4 kb upstream region of the UCP1 gene in forskolin-treated cells. Since PGC-1α is known to potently regulate its own expression in a feed-back loop (Handschin et al., 2003), it was asked if PGC-1α is required for the action of PRDM16 on the PGC-1α promoter. In PGC-1α-deficient brown preadipocytes, the PGC-1α reporter gene was only activated by PRDM16 after re-expression of PGC-1α (FIG. 22B). These data thus reveal a requirement for PGC-1α protein in the activation of the −2 kb PGC-1α promoter by PRDM16.

Previous studies showed that cells lacking PGC-1α and PGC-1β lose brown fat character (Uldry et al., 2006), so it was investigated whether PRDM16 could enhance the transcriptional activity of PGC-1α and PGC-1β. To do this, PGC-1α, PGC-1β, PRC, SRC1 and VP16 were expressed as fusion proteins covalently bound to the Gal4-DNA binding domain (DBD), together with either PRDM16 or control vector. The transcriptional activity of Gal4-fusions was assayed using a reporter gene driven by the Gal1-UAS sequence. In these assays, PRDM16 robustly activated both PGC-1α and PGC-1α but did not activate the related coactivator protein PRC (FIG. 22C), or the unrelated coactivators SRC1 and VP16.

It was then assessed whether the enhancement of PGC-1α and PGC-1α activity by PRDM16 was linked to a physical interaction between these proteins. Using co-immunoprecipitation assays in brown adipocytes, endogenous PGC-1α and PGC-1β proteins were detected in a complex with PRDM16 protein (FIG. 22D). The PRDM16-PGC-1α interaction appeared to be direct since purified GST-PGC-1α fusion protein but not GST alone binds to in vitro translated PRDM16 (FIG. 22E). Domain mapping experiments identified two regions in PGC-1α (250-400 and 590-797) that interact with PRDM16. Correct folding of PGC-1α fragments 1-190 and 200-350 was verified by their binding to another PGC-1α interacting protein, ERR-α. Taken together, these data strongly suggest that PRDM16 directs at least some aspects of brown fat determination and function through a direct interaction with the PGC-1α and PGC-1β transcriptional coactivator proteins.

Figure 23:
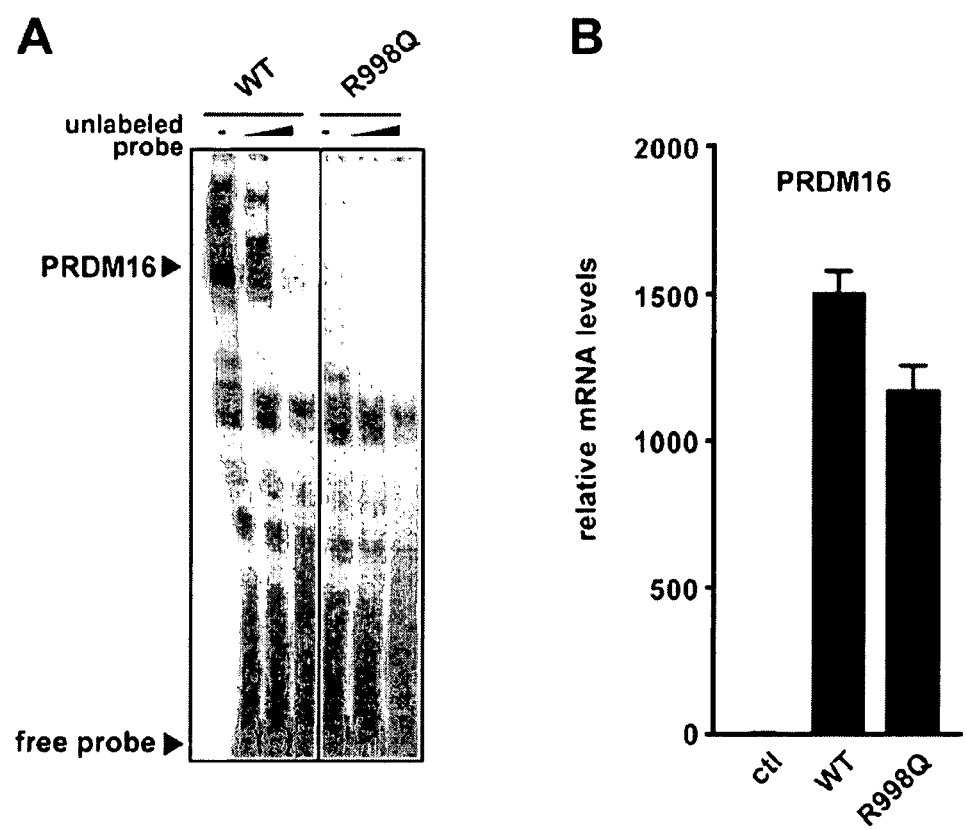
FIG. 23 shows that an R998Q mutant allele of PRDM16 does not bind DNA. Figure (A) shows electrophoretic mobility shift assays (EMSA) performed using in vitro translated wildtype PRDM16 and R998Q mutant proteins to investigate their ability to bind DNA containing a consensus binding site for PRDM16. (B) shows real-time PCR analysis of wildtype and R998Q mutant PRDM16 mRNA levels in adipocytes at day 6 of differentiation (n=3, mean±SD).

PRDM16 contains two distinct DNA binding domains that consist of 7 C2H2 repeats at the N-terminus and 3 repeats at C-terminus. Since previous work has shown that PRDM16 binds directly to DNA (Nishikata et al., 2003), it was asked whether PRDM16 requires direct sequence-specific DNA-binding to induce the brown fat gene program. Based on the structural characteristics of zinc finger motifs (Pavletich and Pabo, 1991), a series of mutants was created with point mutations in the conserved amino acids typically required for DNA binding. Among them, it was found that an R998Q mutant allele completely loses DNA binding to the known consensus sequences of PRDM16 (FIG. 23A). Importantly, the R998Q mutant allele retains the ability to interact with PGC-1α (FIG. 22F). It was next examined whether the R998Q mutant protein was able to activate the brown fat gene program when expressed in PPARγ−/− cells together with PPARγ2. Importantly, adipocytes from these cultures expressed equivalent levels of PRDM16 mRNA (FIG. 23B). Strikingly, a large number of brown fat-selective genes including elovl3, cidea, PGC-1α and UCP1 were induced to similar extents by R998Q mutant and wildtype PRDM16 (FIG. 22G). Moreover, resistin, a WAT-selective gene was markedly repressed by both wildtype PRDM16 and the R998Q allele (FIG. 22G). By contrast, wildtype PRDM16 but not the R998Q allele induced the expression of otop1 and ntrk3 (FIG. 22G). Taken together, these results indicate that PRDM16 does not require sequence-specific DNA binding to activate many, but not all, brown fat genes, and suggest that it functions in BAT determination, at least in part, through direct interaction with the PGC-1s and other proteins.

Knockdown of PRDM16 Ablates the Genetic Program of Brown Fat

Figure 24:
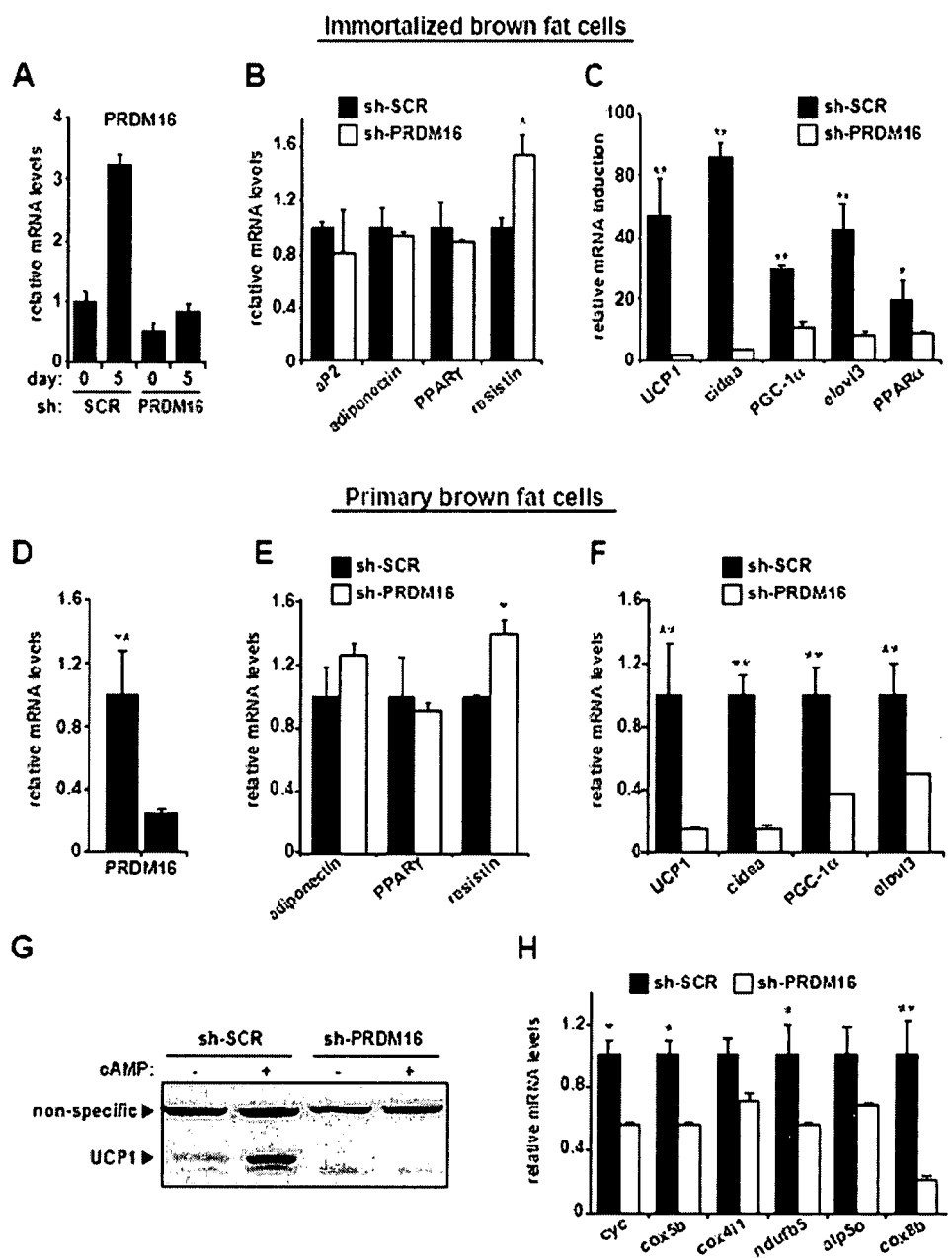
FIG. 24 shows that knockdown of PRDM16 in brown fat cells ablates their brown fat characteristics. (A) shows PRDM16 mRNA levels in immortalized brown fat cells expressing shRNA targeted to PRDM16 or a scrambled (SCR) control-shRNA before (day 0) and after their differentiation (day 5) into adipocytes. (B) shows gene expression in brown fat cells (day 5) expressing sh-PRDM16 or sh-SCR including: markers common to white and brown fat cells (aP2, PPARγ, adiponectin) and resistin, a white fat cell selective gene. (C) shows the differentiation-linked mRNA induction (day 0 to day 5) of brown fat-selective genes in sh-PRDM16 and sh-SCR expressing cells. (D)-(F) show gene expression in adipocytes (day 6) from sh-PRDM16 and sh-SCR expressing primary brown preadipocytes including mRNA levels of: PRDM16 (D); adiponectin, PPARγ and resistin (E); brown fat-selective genes (F).

The requirement for PRDM16 in determining the brown fat phenotype was investigated using siRNA technology to specifically knockdown PRDM16 in the brown fat cell lineage. To this end, a siRNA sequence was identified that efficiently depleted PRDM16 mRNA and protein levels in murine cells. Expression of the corresponding shRNA (short-hairpin) by retrovirus efficiently reduced PRDM16 expression in brown fat preadipocytes and completely blocked the differentiation-linked induction of PRDM16 mRNA in these cells (FIG. 24A). Depletion of PRDM16 in immortalized brown fat cells did not suppress morphological differentiation, nor did it impact the expression of adipocyte markers that are not specific for brown fat, such as aP2, adiponectin or PPARγ (FIG. 24B). However, PRDM16-depletion resulted in a broad loss of brown fat gene expression including severely reduced levels of UCP1, cidea, PGC-1α elovl3 and PPARα relative to cells infected with a sh-scramble (SCR) control (FIG. 24C). Notably, UCP1 and cidea, whose expression defines the identity of "brown fat", were both decreased by 95% in PRDM16-depleted cells (FIG. 24C). Furthermore, some white fat selective mRNAs, such as resistin were increased in PRDM16-depleted cells (FIG. 24B).

Loss of function experiments were also performed in primary brown preadipocytes immediately after their isolation. Transduction of primary brown preadipocytes with sh-PRDM16 caused a ~70% reduction of PRDM16 mRNA at day 6 of differentiation (FIG. 24D). Once again, this caused no visible decrease in morphological differentiation and no difference in the expression of mRNAs common to white and brown fat cells, such as adiponectin and PPARγ (FIG. 24E). As in the immortalized cells, the expression of most, if not all, brown fat selective genes, including UCP1, cidea, elovl3 and PGC-1α were significantly decreased in PRDM16-depleted primary brown fat cells (FIG. 24F). Specifically, loss of PRDM16 caused an 85% reduction in UCP1 and cidea mRNAs and a 60% decrease in the expression of PGC-1α. Furthermore, PRDM16-depleted brown fat cells exhibited close to a complete loss of UCP1 protein expression that was readily apparent in control cultures after cAMP stimulation (FIG. 24G). Expression of a broad set of mitochondrial genes, that are vital to brown fat function, was significantly reduced by knockdown of PRDM16 in immortalized and primary brown fat cells (FIG. 24H). This included a 70% reduction in the mRNA levels of cox8b, a highly brown fat selective mitochondrial gene (FIG. 24H). The effect of PRDM16-depletion on the expression of the brown-white fat selective gene set in both cellular models is summarized in Table 1. These data establish a near absolute requirement for PRDM16 in determining the identity of brown fat cells. PRDM16, however, is not required for aspects of adipogenesis that are common to brown and white fat cells.

Transgenic PRDM16 Expression in WAT Stimulates the Formation of Brown Fat Cells

Figure 25:
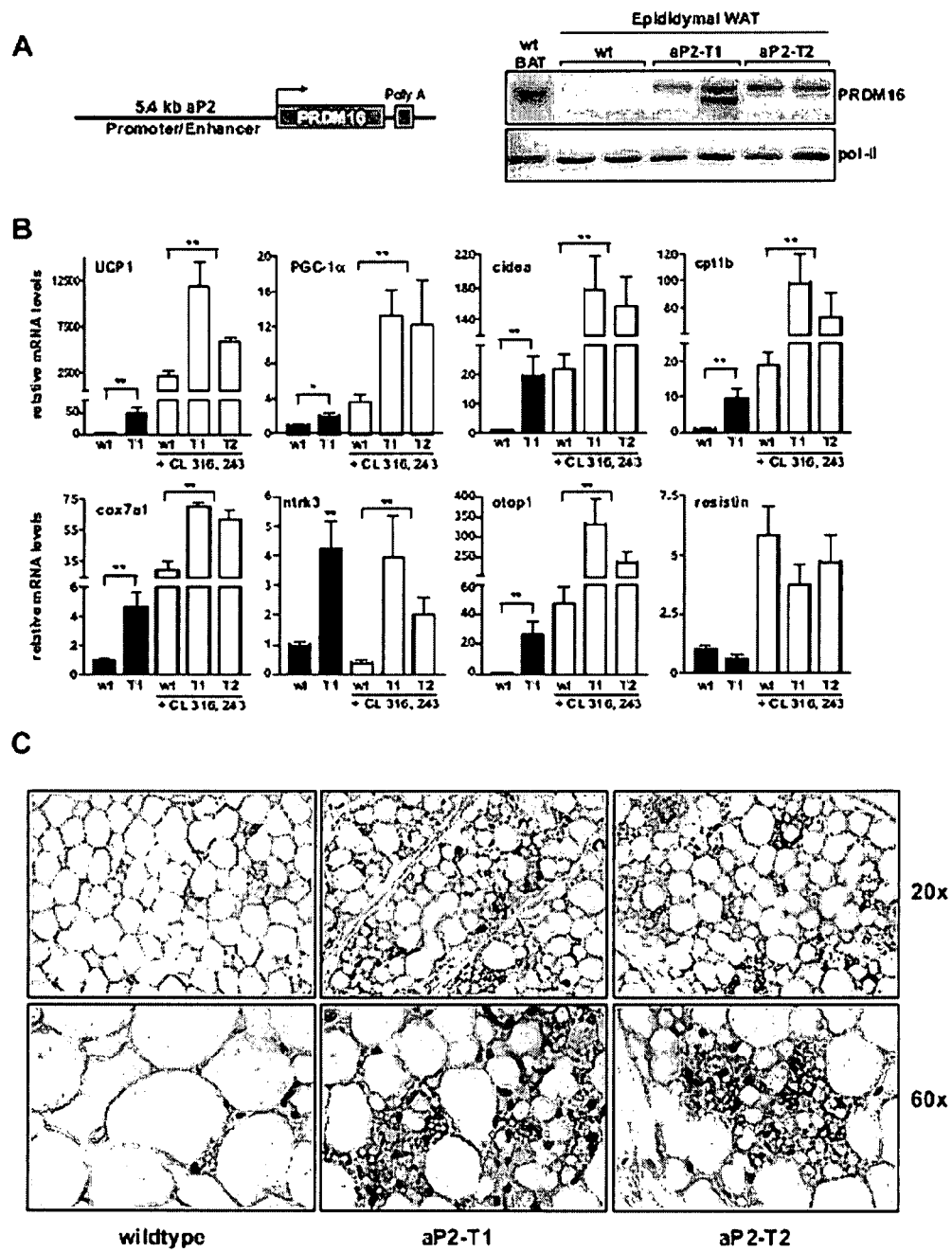
FIG. 25 shows that the transgenic expression of PRDM16 in WAT depots induces the formation of BAT cells. (A) shows that the fat-specific aP2 promoter/enhancer was used to express PRDM16 in WAT depots. Western blot analysis for PRDM16 protein expression is shown in: non-transgenic, wildtype (wt) BAT; wt WAT; and WAT from two strains of aP2-PRDM16 transgenic mice (aP2-T1 and aP2-T2). POL-II protein expression was used to control for loading. (B) shows expression of BAT-selective genes and resistin in WAT from wildtype (wt) and aP2-T1 transgenic mice. This gene set was also measured in WAT from wt, aP2-T1 and aP2-T2 mice that had been treated with CL 316, 243 (n=7-10 mice per group, mean±SE). (C) shows immunohistochemistry for UCP1 protein (brown stain) in sections of WAT from wt and transgenic mice (T1 and T2) after treatment with CL 316, 243 (* $p<0.05$; ** $p<0.01$).

PRDM16 can drive the transcriptional program of BAT when expressed in white fat progenitors before differentiation; however its ability to stimulate BAT cell determination in a purely in vivo context remained unclear. To address this question, PRDM16 was expressed in WAT by transgenesis. Since there are no known fat-selective promoters that express well in preadipose cells, the aP2 promoter/enhancer was utilized, which is active during fat cell differentiation (Graves et al., 1992; Ross et al., 1990). Several transgenic mouse strains were developed and the two highest expressing strains (aP2-T1 and aP2-T2) had levels of PRDM16 protein in epididymal WAT that were equivalent to or somewhat less than its expression in wildtype interscapular BAT (FIG. 25A). PRDM16 is expressed in wildtype BAT and in one transgenic WAT sample as a closely spaced doublet of 150-170 kD; the molecular basis for this doublet is not known. Transgenic PRDM16 expression induced a broad set of BAT-selective genes in epididymal white fat depots from 3-4 month old aP2-PRDM16 (T1) (n=7), as compared to non-transgenic littermates (n=10) (FIG. 25B). For example, the mRNA levels of UCP1, cidea, cpt1b, and otop1 were increased by 50-, 20-, 10-, and 20-fold respectively in WAT from aP2-PRDM16 relative to non-transgenic mice. PGC-1α, cox7a1 and ntrk3 were also significantly elevated by transgenic expression of PRDM16. Furthermore, expression of resistin, a white fat cell selective gene, was slightly decreased in aP2-PRDM16 transgenic fat. These data demonstrate a robust induction of the genetic program of brown fat by PRDM16 in a classic white fat depot.

WAT is poorly innervated, at least compared to BAT, and the action of PRDM16 as a determinant of BAT in cellular models was enhanced by cAMP treatment, which mimics sympathetic (adrenergic) input. Wildtype and aP2-PRDM16 mice (aP2-T1 and aP2-T2) were therefore treated with CL 316, 243, a selective β3-adrenergic agonist, for 6 days. In wildtype WAT, this treatment increased PRDM16 mRNA expression by 4-fold coincident with the emergence of small clusters of brown fat cells and increased expression of many brown fat-selective genes (FIG. 25B). Notably, the induction of these BAT-related genes in WAT was greatly enhanced in both strains of aP2-PRDM16 mice (FIG. 25B). In particular, UCP1, PGC-1α and cidea were expressed to 5-fold, 4-fold and 9-fold higher levels respectively in the WAT of CL316, 243 treated aP2-PRDM16 relative to non-transgenic mice (n=8 (T1), n=6 (T2)) (FIG. 25B). BAT-selective genes were expressed in WAT of aP2-PRDM16 animals at a significant fraction of their levels in similarly treated bona fide interscapular BAT. For example, PGC-1α, UCP1 and cidea were expressed in transgenic WAT at about 80%, 15% and 30% of wildtype BAT levels.

The transgenic mice were also investigated for the morphological emergence of brown fat cells. As shown in FIG. 25C and as demonstrated before (Ghorbani and Himms-Hagen, 1997; Himms-Hagen et al., 1994), WAT from CL 316, 243 treated control animals showed few cells with a multilocular appearance that also stained positively for UCP1. In striking contrast, WAT depots from aP2-PRDM16 mice had a genuine chimeric appearance with very abundant clusters of multilocular BAT-type cells that stained intensely for UCP1 protein (FIG. 25C). All the multilocular cells in the WAT of aP2-PRDM16 transgenic mice expressed UCP1 protein and all UCP1-expressing cells had a multilocular appearance, suggesting that these cells were bona fide brown fat cells. Approximately 10-20% of all cells in epididymal WAT depots of aP2-PRDM16 transgenic mice were BAT-type fat cells, while equivalent depots of the control animals had less than 1% of BAT-type cells. These data show that PRDM16, when expressed at or below authentic BAT levels, can control the determination of brown adipose cells in a classic white fat depot.

A detailed understanding of the brown fat cell and its unique ability to dissipate chemical energy may offer new treatment avenues for obesity and associated diseases. In small mammals that retain distinct brown fat pads as adults, the heat produced by brown fat is an important contributor to overall energy balance (Cannon and Nedergaard, 2004; Cederberg et al., 2001; Ghorbani et al., 1997; Ghorbani and Himms-Hagen, 1997; Guerra et al., 1998; Kopecky et al., 1995; Kopecky et al., 1996; Lowell et al., 1993; Rothwell and Stock, 1979; Tsukiyama-Kohara et al., 2001). Although adult humans do not have distinct brown fat depots, they do appear to have small numbers of brown adipocytes in their white fat depots, and these brown cells proliferate under certain circumstances, such as chronic cold exposure (Garruti and Ricquier, 1992; Huttunen et al., 1981; Lean et al., 1986; Oberkofler et al., 1997). Thus, the molecular mechanisms that regulate brown fat cell determination are of significant and escalating biomedical interest.

A great deal is known about the metabolism and function of mature white and brown adipocytes; however, the developmental origins of these cell lineages have remained elusive. The majority of brown fat develops prenatally and is mature and fully functional at birth, when thermogenic requirements are particularly high (Nedergaard et al., 1986). Most WAT, on the other hand, develops postnatally in response to relative nutritional excess. It has been presumed that white and brown fat cells are closely related to each other developmentally because they express many common enzymes, and both require PPARγ for their differentiation. Recent fate-mapping experiments in mice show that interscapular brown fat but not white fat arises from a population of Engrailed-1 expressing cells in the dermomyotome, a structure that also gives rise to muscle and skin (Atit et al., 2006). These data suggests that the two types of fat cells may have quite different origins.

Figure 26:
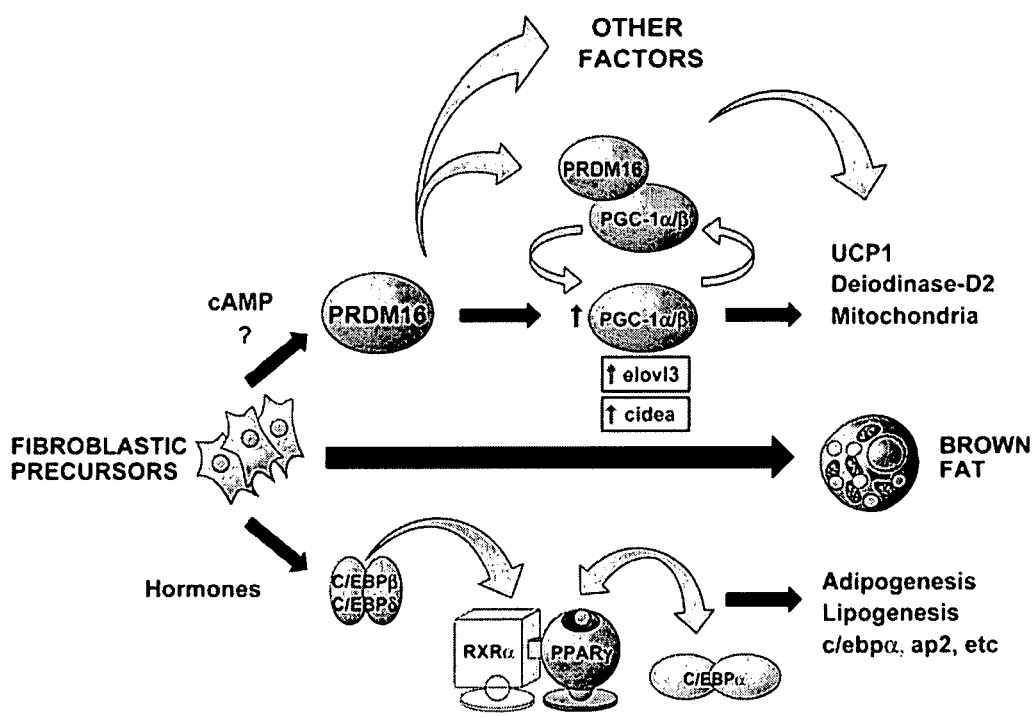
FIG. 26 shows a model of PRDM16 function in brown fat determination. PRDM16 expression is induced in fat cell precursors during brown fat adipogenesis. PRDM16 activates a broad program of brown fat determination including expression of PGC-1α, elovl3, cidea and PRDM16 itself. PRDM16 action renders fat cells responsive to adrenergic signals, such that expression of UCP1 and other thermogenic genes can be further increased by cAMP. The function of PRDM16 is mediated, at least in part, via its physical interaction with PGC-1α and PGC-1β. PRDM16 regulates brown fat character without influencing the general program of adipocyte differentiation (common to BAT and WAT) that is controlled by PPARγ and C/EBP family members.

PRDM16 is expressed very selectively in brown fat cells versus white fat cells and stimulates nearly all the key characteristics of authentic brown fat cells when expressed at or near physiological levels. This includes enhanced mitochondrial gene expression and mitochondrial density, increased expression of PGC-1α, UCP1 and a very large increase in the uncoupled fraction of respiration. The expression of UCP1 and PGC-1α induced by PRDM16 is further enhanced by cAMP, as it is in authentic brown fat cells. At a global scale, a large majority of genes that are selectively expressed in brown adipocytes are positively regulated by PRDM16 (Table 1). Conversely, PRDM16 expression suppressed the mRNA levels of several genes that are selectively enriched in white fat such as resistin and serpin3ak. PRDM16 expression does not influence the expression of those genes that are common to both brown and white fat cells. Several BAT genes including UCP1 and PGC-1α were induced by PRDM16 in the genetic absence of PPARγ (and therefore fat cell differentiation). PRDM16 is shown here to activate a brown fat gene program in many different kinds of adipocytes as long as it is introduced before cell differentiation. These results suggest that the mechanism by which PRDM16 determines brown fat fate is, at least partly, separable from the adipogenic differentiation pathway common to white and brown fat cells (FIG. 26).

A very effective shRNA directed against PRDM16 permitted investigation of the requirement for this factor in the expression of brown fat-selective genes in established brown fat cell lines, and in primary brown fat cells. The reduction of PRDM16 levels has no effect on morphological differentiation of these cells, but causes an almost complete suppression of brown fat-selective genes, including UCP1 mRNA and protein, while leaving intact the expression of genes common to both white and brown fat cells such as PPARγ and aP2. Clearly, PRDM16 is required for the expression of the brown fat phenotype in isolated cells. Examination of this feature will be important in mice ablated for PRDM16 in vivo.

A key question is how does PRDM16 stimulate the development of a brown fat gene program? This protein is annotated in databases as a potential transcription factor because it possesses two zinc-fingers. However, while zinc finger proteins are often DNA binding factors, it is also clear that zinc finger domains can mediate protein-protein interactions (Leon and Roth, 2000). It has been confirmed herein that PRDM16 does indeed bind to DNA in a sequence-specific manner, but this is not required for its regulation of many BAT-selective genes. On the other hand, it is clear that PRDM16 activates the expression as well as the transcriptional function of both PGC-1α and PGC-1β, apparently through direct physical binding. While functions of PRDM16 in other aspects of brown fat regulation are by no means ruled out, the PRDM16-stimulated activity of PGC-1α and PGC-1β may explain many actions of PRDM16 in brown fat determination (FIG. 26).

As shown previously, PGC-1α can activate many of the genes that comprise the thermogenic program of brown fat, such as UCP1 and Deiodinase d2 (Puigserver et al., 1998). On the other hand, PRDM16 is shown to have certain actions here that are not consistent with a function solely through modulation of PGC-1α expression and/or function. In fact, genetic studies have shown conclusively that mice lacking PGC-1α retain identifiable, though abnormal, brown fat tissue (Lin et al., 2004). Similarly, isolated brown fat cells lacking PGC-1α still express several genes characteristic of brown fat (Uldry et al., 2006). However, it is notable that shRNA-mediated suppression of PGC-1β in the cells lacking PGC-1α caused a further loss of the brown fat phenotype (Uldry et al., 2006). Thus, it is possible that PRDM16 functions as a brown fat determination factor, at least in part, by robustly stimulating PGC-1α and PGC-1β simultaneously. PRDM16 may also increase PGC-1 coactivator function in other tissues where it is expressed, such as heart, brain and kidney, with important physiological consequences.

How PRDM16 achieves this activation of the PGC-1s remains to be determined. The PRDI-BF1 and RIZ homology (PR) domain present in a subclass of zinc finger proteins, including PRDM16, is highly homologous to the SET domain that is noted for its histone lysine methyltransferase activity and diverse functions in regulating chromatin structure (Huang et al., 1998; Rea et al., 2000). Other PR-domain containing factors such as RIZ1 (Retinoblastoma interacting zinc finger-1) and Meisitz have intrinsic histone methyltransferase activity, while PRISM (PR-domain in smooth muscle) binds and recruits a histone methyltransferase (Davis et al., 2006; Hayashi et al., 2005; Kim et al., 2003). Another methyltransferase protein, PRMT1, has been shown to bind to PGC-1α and activate it via arginine methylation (Teyssier et al., 2005). Whether the PR-domain of PRDM16 has enzymatic function and whether this activity is required for stimulating brown fat gene expression remains to be established.

Components that can influence the brown fat phenotype, in addition to the PGC-1s, have been identified, such as FOXC2, Rb, p107 and RIP140 (Cederberg et al., 2001; Christian et al., 2005; Hansen et al., 2004; Leonardsson et al., 2004; Powelka et al., 2006; Scime et al., 2005). It will be important to investigate their genetic interactions with PRDM16. The absolute requirement for PRDM16 in the formation of brown adipocytes suggests that the mechanism of action of these other factors may involve PRDM16. Whether they act upstream or downstream of PRDM16 in the differentiation program of brown fat remains to be elucidated.

The replacement of BAT with WAT in humans, and in obese mice and rats, has shown that these tissues can interconvert to some extent in vivo. Similarly, prolonged exposure to cold or β-adrenergic agonists induces the appearance of many brown fat cells within classic white fat depots (Himms-Hagen et al., 2000). This so-called "transdifferentiation" of fat by cold-exposure or β-adrenergic agonists could be due to the acquisition of brown fat cell features in preformed white fat cells and/or by the differentiation of resident committed brown preadipocytes into mature brown fat cells. While this important issue is not entirely closed, the latter scenario is supported by the observation that preadipocytes contained in fat tissues are committed to the brown or white fate (Klaus, 1997; Klaus et al., 1994; Klaus et al., 1995; Kozak and Kozak, 1994). In light of these data, it is very intriguing that PRDM16 expression did not convert white mature adipocytes into brown type cells. However, the white fat cell precursors present in whole fat tissues could be converted to a brown fat-like phenotype very efficiently when PRDM16 was introduced before differentiation. Furthermore, the emergence of UCP1-positive brown fat cells in the white fat depots of transgenic mice suggests strongly that PRDM16 directs the differentiation of resident white fat progenitors into the BAT fate. The small clusters of BAT cells in wildtype WAT most likely arise from BAT progenitors that are present in small numbers within white depots. The stimulation of PRDM16 action by β-adrenergic signaling is not surprising, given the known importance of this cascade in BAT development (Cannon and Nedergaard, 2004). The mechanism by which cAMP signaling modulates the activity of PRDM16 is an important outstanding question from this study.

Taken together, inducing PRDM16 expression in preadipocytes could constitute a strategy to raise whole body energy expenditure and prevent excess fat accumulation. Without being limited by theory, this can be done by using drugs that raise PRDM16 levels in fat cell precursors, or by engineering preadipocytes ex vivo, and then reinjecting them, analogous to the transplantation experiments done here.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

TABLE 1

|  | bat/wat fold change | prdm16/ctl adipocytes | p value | 9eb2 bat fold scr/ si-prdm16 | p value | primary bat fold scr/ si-prdm16 | p value |
|---|---|---|---|---|---|---|---|
| Brown fat cell selective genes | | | | | | | |
| otopetrin1 | 221.10 | 15.4 +/- 3.4 | 0.0019 | 3.60 | 0.0005 | 0.49 | 0.1585 |
| *cpt1b | 157.33 | 2.6 +/- 0.85 | 0.0348 | 0.19 | 0.0002 | 0.33 | 0.0511 |
| *cidea | 150.98 | 436 +/- 110 | 0.0003 | 0.19 | 0.0000 | 0.16 | 0.0004 |
| *UCP1 | 138.62 | 7.4 +/- 2.3 | 0.0085 | 0.03 | 0.0030 | 0.20 | 0.0126 |
| *cox7a1 | 112.22 | 3.1 +/- 0.9 | 0.0320 | 0.21 | 0.0006 | 0.57 | 0.0043 |
| *cox8b | 83.07 | 137 +/- 23 | 0.0005 | 0.12 | 0.0004 | 0.27 | 0.0032 |
| ntrk3 | 47.44 | 16.6 +/- 2.5 | 0.0004 | 0.38 | 0.0056 | 0.67 | 0.1913 |
| cpn2 | 47.26 | 3 +/- 1.4 | 0.0865 | 1.70 | 0.0696 | 0.30 | 0.0430 |
| deiodinase d2 | 38.76 | 3.7 +/- 1.1 | 0.0122 | 2.40 | 0.0090 | 0.30 | 0.0030 |
| elovl6 | 30.39 | 1.8 +/- 0.3 | 0.0296 | 1.26 | 0.0064 | 1.02 | 0.9147 |
| S100b | 27.89 | 5.4 +/- 1.3 | 0.0005 | 0.34 | 0.0010 | 0.75 | 0.4706 |
| *gpd2 | 26.84 | 1.8 +/- .4 | 0.0003 | 0.37 | 0.0002 | 0.26 | 0.0110 |
| *PGC-1α | 24.22 | 10.2 +/- 2.2 | 0.0002 | 0.35 | 0.0001 | 0.39 | 0.0070 |
| err-γ | 23.75 | 1.60 +/- 0.2 | 0.3490 | 0.25 | 0.0010 | 0.40 | 0.0324 |
| *eva1 | 23.10 | 32.2 +/- 6.7 | 0.0008 | 0.29 | 0.0011 | 0.28 | 0.0503 |
| *elovl3 | 21.06 | 5.9 +/- 1.4 | 0.0040 | 0.19 | 0.0018 | 0.54 | 0.0047 |
| acaa2 | 18.87 | 2.8 +/- .6 | 0.0010 | 0.79 | 0.0950 | 0.47 | 0.0564 |
| *ppar-α | 18.21 | 5.8 +/- 1.9 | 0.0019 | 0.45 | 0.0039 | 0.58 | 0.1300 |
| *acss1 | 13.78 | 3.03 +/- 1.6 | 0.0013 | 0.22 | 0.0002 | 0.15 | 0.0336 |
| PRDM16 | 10.80 | 255 +/- 31 | 0.0001 | 0.29 | 0.0002 | 0.28 | 0.0259 |
| White fat cell selective genes | | | | | | | |
| *serpina3k | 0.02 | 0.4 +/- 0.13 | 0.00004 | 3.90 | 0.0010 | 1.40 | 0.0403 |
| *resistin | 0.02 | 0.38 +/- 0.11 | 0.0105 | 1.73 | 0.0274 | 1.34 | 0.0073 |
| resistin like-a | 0.03 | 10.5 +/- 2.2 | 0.0013 | 1.29 | 0.5900 | 1.18 | 0.8700 |
| psat1 | 0.03 | 0.43 +/- 0.11 | 0.0034 | 0.78 | 0.0014 | 1.30 | 0.1390 |
| ccl6 | 0.04 | 2.8 +/- 0.8 | 0.0521 | 1.26 | 0.3821 | 1.75 | 0.0912 |
| fads3 | 0.06 | 0.64 +/- 0.14 | 0.0003 | 0.62 | 0.0021 | 1.12 | 0.6455 |
| aldh1a1 | 0.07 | 3.5 +/- 0.8 | 0.0002 | 0.92 | 0.3565 | 0.62 | 0.1367 |
| hmgn3 | 0.13 | 1.3 +/- 0.29 | 0.2040 | 2.10 | 0.0007 | 1.41 | 0.0114 |
| app | 0.16 | 0.87 +/- 0.2 | 0.3046 | 1.07 | 0.4809 | 0.86 | 0.4652 |

*genes regulated by PRDM16 that show perfect correlation across all experiments.
Shaded entries represent genes that were regulated by ectopic PRDM16 and reciprocally regulated in either PRDM16-depleted brown fat cell lines or in PRDM16-depleted primary brown fat cells.

TABLE 2

Primers used for real-time PCR analysis

| Gene | Forward primer (5' - 3') | Reverse primer (5' - 3') |
|---|---|---|
| acaa2 | GCC TCC ACT CAC ATT GGT TT | ATT GAA GAA AGC TGG GCT GA |
| acss1 | TCC TCC AGG GTA GTG GTG TC | ACC AGA TCC TGG TGG TGA AG |
| adiponectin | GCACTGGCAAGTTCTACTGCAA | GTAGGTGAAGAGAACGGCCTTGT |
| aldh1a1 | TTT GGC CAC ACA CTC CAA TA | GGG CTG ACA AGA TTC ATG GT |
| ap2 | ACA CCG AGA TTT CCT TCA AAC TG | CCA TCT AGG GTT ATG ATG CTC TTC A |
| ccl6 | GTG GCA TAA GAG AAG CAG CAG TC | TAT CCT TGT GGC TGT CCT TGG |
| cidea | TGC TCT TCT GTA TCG CCC AGT | GCC GTG TTA AGG AAT CTG CTG |
| cox4i1 | ACCAAGCGAATGCTGGACAT | GGCGGAGAAGCCCTGAA |
| cox5b | GCTGCATCTGTGAAGAGGACAAC | CAGCTTGTAATGGGTTCCACAGT |
| cox7a1 | CAG CGT CAT GGT CAG TCT GT | AGA AAA CCG TGT GGC AGA GA |
| cox8b | GAA CCA TGA AGC CAA CGA CT | GCG AAG TTC ACA GTG GTT CC |
| coxIII | GCAGGATTCTTCTGAGCGTTCT | GTCAGCAGCCTCCTAGATCATGT |
| cpn2 | GCG TTG TCC TTC AGG CTT AG | TCC CCA CAT CTG TTC TCA CA |
| cpt1b | CGA GGA TTC TCT GGA ACT GC | GGT CGC TTC TTC AAG GTC TG |
| cyt-c | GCAAGCATAAGACTGGACCAAA | TTGTTGGCATCTGTGTAAGAGAATC |
| Dio2 | CAGTGTGGTGCACGTCTCCAATC | TGAACCAAAGTTGACCACCAG |
| elovl3 | TCC GCG TTC TCA TGT AGG TCT | GGA CCT GAT GCA ACC CTA TGA |
| elovl6 | TGC TGC ATC AGT TGA AGA C | TGC CAT GTT CAT CAC CTT GT |
| err-γ | TTC TGC ACA GCT TCC ACA TC | GGA AGA ATT CGT CAC CCT CA |
| eva1 | GTC CCA ACC AGA CCA TCA AC | CTC CAT CTT GCT CTG GAA GC |
| fads3 | GTG ATC CAC ACG AAC CAG TG | TCC CGC TTT TTC TTG TCC TA |
| glut4 | GTG ACT GGA ACA CTG GTC CTA | CCA GCC AGT TGC ATT GTA G |
| GyK | CCGCGAAGAAAGCAGTTCTG | CAAAAAACGTGTCGAGCTGGTA |
| hmgn3 | AGA CTC CGG TTT TGG TGG AAC | CAC AGA GGG CAA AGA TGG AAC |
| lhx8 | ACA CGA GCT GCT ACA TTA AGG A | CCC AGT CAG TCG AGT GGA TG |
| ntrk3 | TGG CTC ACA CTG ATC TCT GG | GCC AGA GCC TTT ACT GCA TC |
| otopetrin1 | ACT AGG ACC CCG TCG AAT CT | ACC ATG CTC TAC GTG CTG TG |
| pgc1α | CCC TGC CAT TGT TAA GAC C | TGC TGC TGT TCC TGT TTT C |
| ppar-α | GCGTACGGCAATGGCTTTAT | GAACGGCTTCCTCAGGTTCTT |
| ppar-γ | GTGCCAGTTTCGATCCGTAGA | GGCCAGCATCGTGTAGATGA |
| prdm16 | CAG CAC GGT GAA GCC ATT C | GCG TGC ATC CGC TTG TG |
| prdm16-utr | TGG CCT TCA TCA CCT CTC TGA A | TTT CTG ATC CAC GGC TCC TGT GA |
| psat1 | TAC CGC CTT GTC AAG AAA CC | AGT GGA GCG CCA GAA TAG AA |
| resistin | CTG TCC AGT CTA TCC TTG CAC AC | CAG AAG GCA CAG CAG TCT TGA |
| retn-like-α | TCC ACT CTG GAT CTC CCA AGA | TCC CTC CAC TGT AAC GAA GAC TC |
| s100b | GTC CAG CGT CTC CAT CAC TT | GGT GAC AAG CAC AAG CTG AA |
| serpina3k | GGC TGA AGG CAA AGT CAG TGT | TGG AAT CTG TCC TGC TGT CCT |
| tbp | GAA GCT GCG GTA CAA TTC CAG | CCC CTT GTA CCC TTC ACC AAT |

TABLE 2-continued

Primers used for real-time PCR analysis

| Gene | Forward primer (5' - 3') | Reverse primer (5' - 3') |
|------|--------------------------|--------------------------|
| ucp1 | ACT GCC ACA CCT CCA GTC ATT | CTT TGC CTC ACT CAG GAT TGG |
| zic1 | CTG TTG TGG GAG ACA CGA TG | CCT CTT CTC AGG GCT CAC AG |

What is claimed:

1. A method for increasing energy expenditure in a mammal comprising inducing PR-domain containing protein-16 (Prdm16) expression in fibroblast, preadipocyte, or white adipose tissue (WAT) stromal-vascular cells sufficient to activate differentiation of said cells into brown fact cells in the mammal, wherein Prdm16 expression is induced using a) a Prdm16 nucleic acid encoding a PRDM16 polypeptide comprising an amino acid sequence which is at least 90 percent identical over its full length to the amino acid sequence of SEQ ID NOs: 2, 4, or 6 or b) a PRDM16 polypeptide comprising an amino acid sequence which is at least 90 percent identical over its full length to the amino acid sequence of SEQ ID NOs: 2, 4, or 6 and wherein the differentiated brown fat cells promote energy expenditure thereby increasing energy expenditure in the mammal.

2. The method of claim 1, wherein the mammal is a human.

3. The method of claim 1, wherein Prdm16 expression increases respiration.

4. The method of claim 3, wherein the respiration is total respiration.

5. The method of claim 3, wherein the respiration is uncoupled respiration.

6. The method of any one of claims 1-5, wherein the PRDM16 polypeptide comprises the amino acid sequence of SEQ ID NOs: 2, 4, or 6.

7. The method of any one of claims 1-5, wherein the PRDM16 polypeptide consists of the amino acid sequence of SEQ ID NOs: 2, 4, or 6.

8. The method of any one of claims 1-5, wherein the PRDM16 polypeptide further comprises a heterologous polypeptide.

* * * * *